(12) United States Patent
Zhang et al.

(10) Patent No.: US 7,803,793 B2
(45) Date of Patent: Sep. 28, 2010

(54) HETEROCYCLIC DERIVED METALLOPROTEASE INHIBITORS

(75) Inventors: Yue-Mei Zhang, Belle Mead, NJ (US); Bangping Xiang, Bridgewater, NJ (US); Shyh-Ming Yang, High Bridge, NJ (US); Kenneth Rhodes, Hopkinton, MA (US); Robert Scannevin, Hopkinton, MA (US); Paul Jackson, Whitehouse Station, NJ (US); Davraj Chakravarty, Hillsborough, NJ (US); Xiaodong Fan, Center Valley, PA (US); Lawrence J. Wilson, Atlanta, GA (US); Prabha Karnachi, Hillsborough, NJ (US)

(73) Assignee: Janssen Pharmaceutica NV (BE)

( * ) Notice: Subject to any disclaimer, the term of this patent is extended or adjusted under 35 U.S.C. 154(b) by 317 days.

(21) Appl. No.: 11/858,972

(22) Filed: Sep. 21, 2007

(65) Prior Publication Data

US 2008/0103129 A1    May 1, 2008

Related U.S. Application Data

(60) Provisional application No. 60/828,226, filed on Oct. 5, 2006.

(51) Int. Cl.
| | |
|---|---|
| C07D 225/02 | (2006.01) |
| C07D 401/06 | (2006.01) |
| C07D 401/12 | (2006.01) |
| C07D 409/12 | (2006.01) |
| A61K 31/55 | (2006.01) |

(52) U.S. Cl. .................. 514/212.03; 514/212.06; 540/524; 540/526; 540/527

(58) Field of Classification Search ............ 540/524, 540/526, 527; 514/212.03, 212.08
See application file for complete search history.

(56) References Cited

FOREIGN PATENT DOCUMENTS

| | | |
|---|---|---|
| EP | 1191024 A1 | 3/2002 |
| WO | WO 96/00214 A | 1/1996 |
| WO | WO 98/38163 A | 9/1998 |
| WO | WO 03/040098 A | 5/2003 |
| WO | WO 2004/024718 A1 | 3/2004 |
| WO | WO 2005/009362 A1 | 10/2005 |

OTHER PUBLICATIONS

Cunningham, L., et al. "Multiple Roles for MMPs and TIMPs in Cerebral Ischemia", GLIA 50: 329-39 (2005).
Gursoy-Ozdemir, Y., et al. "Cortical Spreading Depression Activates and Upregulates MM-9", J. Clinical Investigation 113: 1447-55 (2004).
Handsley, M., et al. "Metalloproteinases and Their Inhibitors in Tumor Angiogenesis", Inter. J. Cancer 115: 849-60 (2005).
Lorenzel, S., et al. "Increased Plasma Levels of Matrix Metalloproteinase-9 in Patients with Alzheimer's Disease", Neurochemistry International 43: 191-6 (2003).
Lorenzl, S., et al. "Matrix Metallooproteinase-9 is Elevanted in 1-Methyl-4-Phenyl-1,2,3,6-Teetrahydropyridine-Induced Parkinsonism in Mice", NeuroMolecular Medicine, 5, 119 (2004).
Tayebjee, M., et al. "Matrix Metalloproteinases in Coronary Artery Disease: Clinical and therapeutic Implications and Pathological Significance", Current Medicinal Chemistry 12: 917-25 (2005).
Vihinen, P., et al. "Matrix Metalloproteinases as Therapeutic Targets in Cancer", Current Cancer Drug Targets 5: 203-20 (2005).
Weimar, C., et al. "Age and National Institutes of Health Stroke Scale Score Within 6 Hours After Onset Are Accurate Predictors of Outcome After Cerebral Ischemia", Stroke 35: 159-62 (2004).
Adam W., et al. "Kimethyldioxirane Epoxidation of α,β-Unsaturated Ketones, Acids and Esters", Tetrahedron Letters, vol. 31, pp. 331-334 (1990).
Cristau, H-J., et al. "A General and Mild Ullmann-Type Synthesis of Diaryl Ether", Organic Letters vol. 6, No. 6, pp. 913-916 (2004).
Doherty, T. et al. "Therapeutic Developments in Matrix Metalloproteinase Inhibition", Expert Opinion, p. 665 (2002).
Flatt, A. et al. "Synthesis and Testing of New End-Functionalized Oligomers for Molecular Electronics", Tetrahedron Letters, vol. 59, pp. 855 (2003).
George, S. "Therapeutic Potential of Matrix Metalloproteinase Inhibitors in Atherosclerosis", Expert Opinion of Investigational Drugs, vol. 9(5), pp. 993-1007 (2000).
Gholap, A. et al. "Copper- and Ligand-Free Sonogashira Reaction Catalyzed by Pd(0) Nanoparticles at Ambient Conditions under Ultrasound Irradiation", JOC Note, No. 70, pp. 4869-4872 (2005).
Greenfield, A., et al. "Synthesis and Biological Activities of Aryl-Ether-, Biaryl- and Fluorene Aspartic Acid and Diaminoproionic Acid Analogs as Potent Inhibitors of the High-Affinity Glutamate Transporter EAAT-2", Bioorganic & Medicinal Chemistry Letters, vol. 15, pp. 4985-4988 (2005).

(Continued)

Primary Examiner—Bruck Kifle

(57) ABSTRACT

This invention provides novel heterocyclic derived matrix metalloprotease inhibitors of the formula:

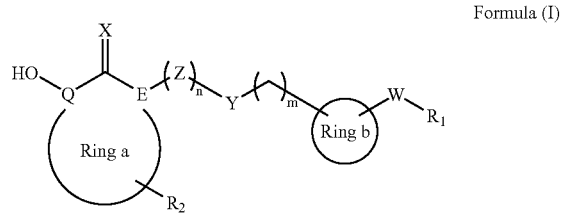

Formula (I)

and pharmaceutical compositions comprising same, useful for treating disorders ameliorated by antagonizing matrix metalloproteases. This invention also provides therapeutic and prophylactic methods using the instant pharmaceutical compositions.

32 Claims, No Drawings

OTHER PUBLICATIONS

Jung, S., et al. "Pathogenic αβ Induces the Expression and Activation of Matrix Metalloproteinase-2 in Human Cerebrovascular Smooth Muscle Cells", Journal of Neurochemistry, vol. 85, p. 1208-1215 (2003).

Kakei, H., et al. "Catalytic Asymmetric Epoxidation of α,β-Unsaturated Esters Using an Yttrium-Biphenyldiol Complex", J. Am. Chem. Soc. vol. 127, p. 8962-8963, (2005).

Khlobystov, A., et al. "Steroselective Association of Binuclear Metallacycles in Coordinating Polymers", JACS, vol. 124, pp. 6753-6761 (2003).

Kogan, T. et al. "A Regio- and Stereocontrolled Total Synthesis of (-)-Indolactam-V", Tetrahedron Letters, vol. 46, No. 19, pp. 6623-6632 (1990).

Lamothe, M., et al. "Differentiation Between Partial Agonists and Neutral 5-HT$_{1B}$ Antagonists by Chemical Modulation of 3-{3-(N,N-Dimethylamino)propyl]-4-hydroxy-N-4-(pyridine-4-yl)phenyl]benzamide (GR-55562), (1997).

Lanier, M. et al. "Steroselective Synthesis of F-Alkyl α,β-Unsaturated Esters and Their Epoxidation", Tetrahedron Letters, vol. 34, No. 15, pp. 2469-2472 (1994).

Lapchak, P.A., et al. "Metalloproteinase Inhibition Reduces thrombolytic (Tissue Plasminogen Activator)-Induced Hemorrhage After Thromboembolic Stroke", Stroke, pp. 3034 (2000).

Li, J., et al. "An Efficient Stile Cross-Coupling Reaction Catalyzed by Pd(Oac)$_c$AB-Cy Catalytic System", Tetrahedron Letters, No. 61, pp. 7289-7293, (2005).

Li, J., et al. "Efficient Palladium-Catalyzed Homocoupling Reaction and Sonogashira Cross-Coupling Reaction of Terminal Alkynes Under Aerobic Conditions", JOC, No. 70, pp. 4393-43956 (2005).

Li, J., et al "Efficient and Copper-Free pd(Oac)$_2$/DABCO-Catalyzed Sonogashira Cross-Coupling Reaction", Synthesis, No. 5, pp. 0804-0808, (2005).

MA, D., et al. "N,N-Dimethyl Glycine-Promoted Ullmann Coupling Reaction of phenols and Aryl Halides", American Chemical Society, (2003).

Miyabe, H., et al "Hydroxylamines as Oxygen Atom Nucleohles in Transitio-Metal-Catalyzed Allylic Substitution", J. Org. Chem. No. 70, pp. 2148-2153 (2005).

Miyabe, H., et al. "O-Allyic Substitution of Hydroxylamine Derivatives Having an N-Electron-Withdrawing Substituent", Synlett No. 4, p. 567 (2003).

Miyaura, N., et al, "Palladium-Catalyzed Cross-Coupling Reactions of Organoboron Compounds", Chem. Rev. No. 95, pp. 2457-2483 (19950.

Opdenakker, G. et al. "Functional Roles and Therapeutic Targeting of Gelatinase HB and Chemokines in Multiple Sclerosis", The Lancet vol. 2. p. 747, (2003).

Pfefferkorn, T., et al. "Closure of the Blood-Brain Barrier by Matrix Metalloproteinase Inhibition Reduces rtPA-Mediated Mortality in Cerebral Ischemia With Delayed Reperfusion", Stroke, p. 2025 (2002).

Puerta, D., et al. "Potent, Selective Pyrone-Based Inhibitors of Stromelsi-1", JACS, No. 127, pp. 14148-14149 (2005).

Puerta, D., et al. "New Beginnings for Matrix Metalloproteinase Inhibitors: Identification of High-Affinity Zinc-Binding Groups", J. Am. Chem. Soc. No. 126, pp. 8388-8389 (2004).

Rodriguez, S., et al. "Distereoselectivity in the Epoxidation of Y-Hydroxy α,β-Unsaturated Ester: Temperature and Solvent Effect", Tetrahedron Letters, No. 45 pp. 5359-5361 (2004).

Romanic, A. et al. "Matrix Metalloproteinase Expression Increases After Cerebral Focal Ischemia in Rats", American Heart Association (1998).

Wang, L., et al. "The Sonogashira Coupling Reaction Catalyzed by Ultrafine Nickel Powder", Royal Society of Chemistry, pp. 514 (2004).

Whittaker, M., et al. "Design and Therapeutic Application of Matrix Metalloproteinase Inhibitors", American Chemical Society 99, pp. 2735-2776 (1999).

Wolin, R. et al. "Novel Glycine Transporter Type-2 Reuptake Inhibitors, Part I: α-amino acid Derivative", Bioorganic & Medicinal Chemistry No. 12 pp. 447-4492 (2004).

Wu, X., et al "Highly Enantioselective Epoxidation of α-β-Unsaturated Esters by Choral Dioxirane", JACS, No. 124 8792-8793 (2002).

Yong, V. et al "The Potential Use of MMP Inhibitors to Treat CNS Diseases", Expert Opinion on Investigational Drugs, p. 255 (1999).

Yang, D. et al. "Epoxidation of Olefins Using Methyl(trifluormethly)dioxirane Generated In Situ", J. Org. Chem. No. 60, pp. 3887-3889 (1995).

HETEROCYCLIC DERIVED METALLOPROTEASE INHIBITORS

This application claims the benefit under 35 U.S.C. 119(e) of U.S. Provisional Application Ser. No. 60/828,226 filed Oct. 5, 2006. The complete disclosure of the aforementioned related U.S. patent application is hereby incorporated herein by reference for all purposes.

FIELD OF THE INVENTION

This invention relates generally to the field of matrix metalloproteinase (MMP) inhibitors and their therapeutic and prophylactic uses. In particular, the present invention relates to the use of novel zinc binding groups attached to an appropriate metalloprotease recognition unit, which groups function in MMP inhibition. The heterocyclic derived compounds of this invention have potential for the treatment of diseases triggered by the breakdown of connective tissue or extracellular matrix. Examples of relevant therapeutic areas include inflammation, oncology, cardiovascular diseases, and neurological disorders. More specifically, they have utility in the treatment and prevention of strokes.

BACKGROUND OF THE INVENTION

Matrix metalloproteinases (MMPs) are a family of structurally related zinc-dependent proteolytic enzymes that digest extracellular matrix proteins such as collagen, elastin, laminin and fibronectin. Currently, at least 28 different mammalian MMP proteins have been identified, and are grouped based on substrate specificity and domain structure. The wide variety of MMPs normally participate in many different homeostatic tissue remodeling events. Given this broad functional diversity it is not surprising that MMP dysfunction would give rise to a host of different pathologies. A role for MMPs in oncology has been the most extensively explored, as up-regulation of any number of MMPs are one mechanism by which malignant cells can overcome connective tissue barriers and metastasize (Curr Cancer Drug Targets 5: 203-20 (2005)). MMPs also appear to have a direct role in angiogenesis, also making them an important target for oncology indications (Int J Cancer 115: 849-60 (2005) and J Cell Mol Med 9: 267-85 (2005)). Several different classes of MMPs are involved in these processes, but MMP-2, -9 and MT1-MMP have been most often implicated. The cartilage and bone degeneration that results in osteoarthritis and rheumatoid arthritis is due primarily to MMP digestion of the ECM in bone and joints (Aging Clin Exp Res 15: 364-72 (2003). MMP-1, -2, -9, and -13 have been found to be elevated in the tissues and body fluids surrounding damaged tissues. MMPs also have a role in cardiovascular diseases in that they are believed to be involved in atherosclerotic plaque rupture, aneurysm and vascular and myocardial tissue morphogenesis (Expert Opin Investig Drugs 9: 993-1007 (2000) and Curr Med Chem 12: 917-25 (2005)). Elevated levels of MMP-1, -2, -9, and -13 have often been associated with these conditions. Several other pathologies such as gastric ulcers, pulmonary hypertension, chronic obstructive pulmonary disease, inflammatory bowel disease, periodontal disease, skin ulcers, liver fibrosis, emphysema, and Marfan's syndrome appear to involve MMP as well (Expert Opin Ther Patents 12: 665-707 (2002)).

Two enzymes, MMP-2 and MMP-9, appear to have the most significant impact in propagating the brain tissue damage that occurs following an ischemic or hemorrhagic insult. Studies in stroke patients and in animal stroke models have demonstrated that both MMP-2 and -9 expression levels and activity increase sharply over a 24 hour period following an ischemic event. Within the brain, the microvascular endothelial cell tight-junctions are broken down by activated MMP-2 and -9, which results in increased permeability of the blood-brain barrier (BBB). This breakdown in the integrity of the BBB then leads to edema and infiltration of inflammatory agents, both of which cause increased cell death around the infarct core (the penumbra) and increase the possibility of hemorrhagic transformation. Administration of MMP inhibitors has shown to be protective in animal models of stroke (Stroke 29: 1020-30 (1998); Expert Opin Investig Drugs 8: 255-68 (1999); Stroke 31: 3034-40 (2000); Stroke 34: 2025-30 (2003); and J Neurosci 25: 6401-8 (2005)). MMP-9 knockout animals also demonstrate significant neuroprotection in similar stroke models (J Cereb Blood Flow Metab 20: 1681-9 (2000)). In the U.S., stroke is the leading cause of disability, and the third leading cause of mortality. Currently, thrombolitics (e.g. t-PA) are the only approved therapy for stroke; however its use is severely limited due to a narrow dosing window of time and potential hemorrhagic risk. This area has a large unmet medical need for acute interventional therapy.

MMP-9 has also been suggested to play a role in the progression of multiple sclerosis (MS). Studies have indicated that serum levels of MMP-9 are elevated in active patients, and are concentrated around MS lesions (Lancet Neurol 2: 747-56 (2003)). Increased serum MMP-9 activity would promote infiltration of leukocytes into the CNS, a causal factor and one of the hallmarks of the disease. MMPs may also contribute to the severity and prolongation of migraines. In animal models of migraine (cortical spreading depression), MMP-9 is rapidly upregulated and activated leading to a breakdown in the BBB, which results in mild to moderate edema (J Clin Invest 113: 1447-55 (2004)). It is this brain swelling and subsequent vasoconstriction that causes the debilitating headaches and other symptoms associated with migraine. In the cortical spreading depression model, MMP inhibitors have been shown to prevent the opening of the BBB (J Clin Invest 113: 1447-55 (2004)). Related research has shown that MMP-9 is specifically upregulated in damaged brain tissues following traumatic brain injury (J Neurotrauma 19: 615-25 (2002)), which would be predicted to lead to further brain damage due to edema and immune cell infiltration.

Within the central nervous system, altered MMP expression has been linked to several neurodegenerative and neurovascular disease states (Expert Opin Investig Drugs 8: 255-68 (1999)), most notably in stroke (Glia 50: 329-39 (2005)). MMPs may also have additional roles in other chronic CNS disorders. In an animal model of Parkinson's disease, MMP-9 was found to be rapidly upregulated after striatal injection of a dopaminergic neuron poison (MPTP) (Neuromolecular Med 5: 119-32 (2004)), and MMP-3 has been shown to process α-synuclein to an aggregation-prone form (J Biol Chem 280: 25216-24 (2005)). This implicates MMPs in both the neuronal remodeling that occurs upon cell loss and one of the potential causative factors of the disease. In patients with Alzheimer's disease, MMP-9 was found to be upregulated in postmortem plasma samples compared to normal controls (Expert Opin Investig Drugs 8: 255-68 (1999) and Neurochem Int 43: 191-6 (2003)). Furthermore, pathologic expression of Aβ peptides induces expression and activation of MMP-2, which may contribute to cerebral amyloid angiopathy, a major pathological feature of Alzheimer's disease (J Neurochem 85: 1208-15 (2003)). MMPs may also have a role in vascular dementia, as MMP-9 levels have been found to be elevated in the cerebrospinal fluid from demented patients (Stroke 35: e159-62 (2004)). Clearly, the pathologic expression of various MMPs can contribute to many different neurodegenerative disorders.

A wide range of MMP inhibitors (MMPIs) have been discussed comprehensively in several review articles (Whittaker, M. et al *Chem. Rev.* 1999, 99, 2735-2776; Skiles, J W. et al *Curr. Med. Chem.* 2001, 8, 425-474; Skiles, J W. et al *Curr. Med. Chem.* 2004, 11, 2911-2977; Matter, H. et al *Curr. Opin. In Drug Discov. & Dev.* 2004, 7, 513-535). A classical approach to the MMPI design is the combination of a zinc-binding group (ZBG) and a side chain binding to enzymes. The most common ZBGs used in MMPI design are hydroxamates, N-hydroxy-formamides, thiols, carboxylates and phosphonic acids. Some of MMPIs incorporating these "classical" ZBGs have been developed for pharmaceutical uses but failed in clinical trials.

A considerable effort was put on discovery of non-classical ZBG based MMPIs and several MMPIs with heterocyclic ZBGs have been disclosed: barbiturates (WO 2005/0107414); thiadiazole derivatives (*Protein Sci.* 1998, 7, 2281-2286; *Bioorg. Med. Chem. Lett.* 2002, 12, 2667-2672); thiadiazine compounds (*J. Med. Chem.* 2001, 44, 3231-3243; EP-01191024 (2001)); imidazolidinedione derivatives (WO 2004/024718 A1; WO 2002/07475148-WO2002/07475152); triazolones (WO 2005/095362 A1).

In JP-02105073 (2002), Shionogi & Co discloses a class of hydroxyl- and alkoxy-succimide with sulfonamide scaffolds as MMP inhibitors stated to have the generic structure

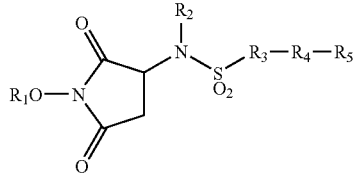

wherein the substituents are as described in the reference.

Eriksson et al. disclose in WO 03/040098 certain metalloproteinase inhibitors stated to have the structure

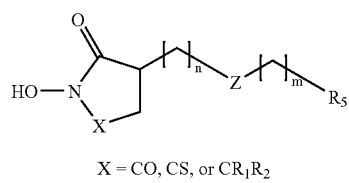

wherein the substituents are as described in the reference.

A galardin (GM 6001) analog with a six-membered ring as ZBG is reported to show weak MMP inhibitory activity on all MMPs tested with IC$_{50}$'s ranging from 20.1 to 104 µM (*Chinese J. Chem.*, 2001, 19, 286), which compound is shown below:

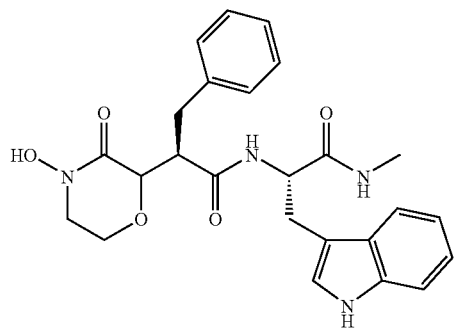

Cohen et al report a bioinorganic approach to MMP inhibition (*Curr. Top. In Med Chem.* 2004, 4, 1551; *J. Am. Chem. Soc.* 2004, 126, 8388-8389). A tris-His active site model of MMP suggests a group of hydroxyl-pyridones (HOPO) and hydroxyl-pyranones, structures of which are shown below, may serve as cyclic six-membered zinc binding functionality. Some of these heterocyclic compounds have been used in siderophore synthesis as Fe(III) chelators and in the synthesis of Pu(IV) sequestering agents.

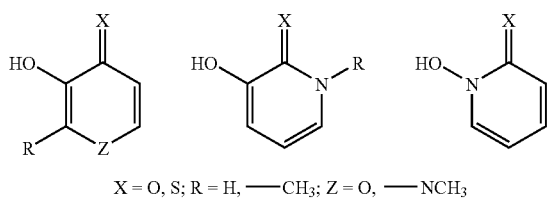

The HOPOs exhibit activity ranging from several hundred to several thousand micromolar for inhibiting MMP3. It is stated that hydroxy-thiopyridones and -thiopyranones are several tens fold more potent than their oxygen-analogs due to zinc thiophilicity.

A series of MMP inhibitors incorporating a pyrone moiety as ZBG has been reported (*J. Am. Chem. Soc.* 2005, 127, 14148-14149). The best compound shows around 10 nM of IC$_{50}$ against MMP-3 and 0.61 µM against MMP-2. The general structure is shown below, wherein P1' group was assembled next to the hydroxyl group on the pyrone ring.

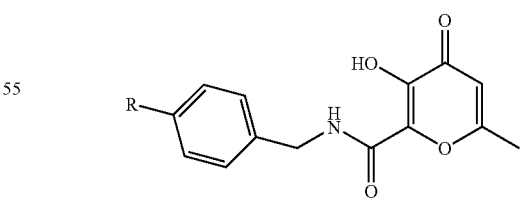

We have now discovered a series of novel compounds incorporating a variety of from six- to nine-membered heterocycle ZBGs useful as MMP inhibitors. The compounds of this invention are potent MMP-2, -9 and -13 inhibitors, while exhibiting less activity against MMP-1. In addition, the compounds of this invention may selectively inhibit other MMPs.

SUMMARY OF THE INVENTION

This invention relates, in part, to methods and compositions useful for the treatment of matrix metalloproteinase-mediated conditions. Specifically, in part, the invention relates to compounds of Formula (I):

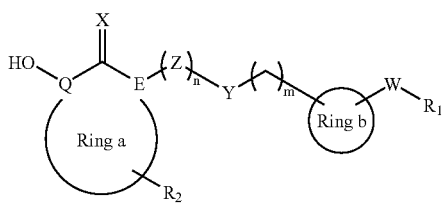

wherein
Ring a is a 6, 7, 8, or 9-membered ring selected from heteroaryl and heterocyclyl, wherein
X is O or S,
E is selected from an sp² carbon,

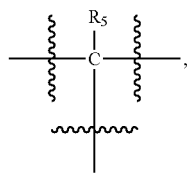

and N, wherein $R_5$ is selected from H, hydroxy, amino, alkoxy, alkylthio, sulfonyl, $C_{1-10}$alkyl, $C_{2-6}$alkenyl, $C_{2-6}$alkynyl, aryl, heteroaryl, and heterocyclyl, and
Q is N or an sp² carbon, provided that when E is an sp² carbon, Q is N;
Ring b is selected from
aryl;
heteroaryl; and
heterocyclyl of the formula

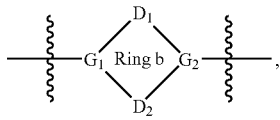

wherein
$G_1$ and $G_2$ are independently selected from N, C, and CH; and
$D_1$ and $D_2$ are each 1-3 independent members selected from CH, $CH_2$, N, S, and O, provided that when $G_1$ or $G_2$ is N, $D_1$ and $D_2$ are independently selected from CH and $CH_2$.
$R_1$ is selected from halo, nitrile, hydroxyl, thiol, amino, alkoxy, alkylthio, sulfonyl, $C_{1-10}$alkyl, $C_{2-6}$alkenyl, $C_{2-6}$alkynyl, cycloalkyl, aryl, heteroaryl, heterocyclyl, carbonyl, and —CHO;
$R_2$ is 0-2 independent members selected from halo, nitrile, hydroxyl, amino, $C_{1-10}$alkyl, $C_{2-6}$alkenyl, $C_{2-6}$alkynyl, alkoxy, alkylthio, sulfonyl, aryl, heteroaryl, heterocyclyl, —C(O)$R_3$, —C(O)O$R_3$, and —C(O)N$R_3R_4$, wherein $R_3$ and $R_4$ are independently selected from H, $C_{1-10}$alkyl, aryl, heteroaryl, and heterocyclyl, or
$R_3$ and $R_4$ together with the N they are attached to form a 3-, 4-, 5-, 6-, or 7-membered heterocyclyl;
W is selected from a covalent bond, —(CH$_2$)$_p$—O—, —O—(CH$_2$)$_p$—, —S(O)$_p$—, —C(O)—, $C_{1-3}$alkylene, $C_{2-3}$alkenylene, $C_{2-3}$alkynylene, and 5-7 membered aliphatic ring containing one or two nitrogens, wherein
p is 0, 1, or 2;
Y is selected from O, S, S(O), S(O)$_2$, —SO$_2$N(R$_6$)—, —N(R$_6$)SO$_2$—, —N(R$_6$)SO$_2$N(R$_7$)—, —N(R$_6$)CO—, —N(R$_6$)PO(OR$_8$)—, —N(SO$_2$R$_8$)—, —N(COR$_8$)—, —N(POOR$_8$R$_9$)—, —CH(OH)—,

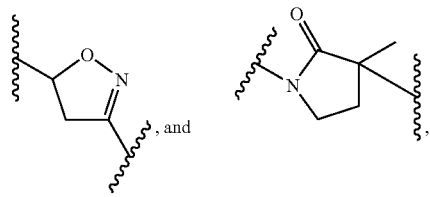

wherein
$R_6$ and $R_7$ are independently selected from H, $C_{1-10}$alkyl, alkylsulfonyl, arylsulfonyl, alkylcarbonyl, and arylcarbonyl, and
$R_8$ and $R_9$ are independently selected from $C_{1-6}$alkyl, aryl, heteroaryl, and heterocyclyl;
Z is —CH(R$_{10}$)— or —CH(R$_{10}$)CH(R$_{11}$)—, wherein
$R_{10}$ and $R_{11}$ are independently selected from H, $C_{1-6}$alkyl, $C_{2-6}$alkenyl, $C_{2-6}$alkynyl, aryl, heteroaryl, and heterocyclyl;
m is 0, 1, or 2; and
n is 0 or 1 with the proviso that when n is 0, E is not N and Y is not O;

or an optical isomer, enantiomer, diastereomer, racemate, prodrug or pharmaceutically acceptable salt thereof.

In addition, this invention relates, in part, to methods of treating a condition that can be ameliorated by antagonizing matrix metalloproteinase, which condition includes, but is not limited to, vascular and myocardial tissue morphogenesis, cancer, cardiovascular diseases, inflammatory diseases, acute and chronic CNS disorders such as neurovascular disorders, neurodegenerative diseases, demylinating diseases, movement disorders, and associated symptoms or complications thereof.

In one aspect, this invention provides a method of therapeutic and prophylactic uses of compounds of Formula (I) for one or more conditions selected from ischemic or hemorrhagic stroke, Parkinson's disease, Alzheimer's disease, cerebral amyloid angiopathy, vascular dementia, headaches such as migraine, traumatic brain injury, multiple sclerosis, edema, atherosclerotic plaque rupture, aneurysm, osteoarthritis, rheumatoid arthritis, gastric ulcers, pulmonary hypertension, chronic obstructive pulmonary disease, inflammatory bowel disease, periodontal disease, skin ulcers, liver fibrosis, emphysema, Marfan's syndrome, and associated symptoms or complications thereof.

In various embodiments of the present invention, before prophylactic or therapeutic administration of the composition to the subject, a determination will be made as to whether or not the subject suffers from one or more MMP-mediated conditions, or is considered to be at a high risk for the development of such conditions.

In certain embodiments of the present invention, a therapeutically effective amount of a compound of Formula (I) is in a range of from about 0.001 mg/kg of body weight to about 200 mg/kg of body weight of the subject. The dosages, however, may be varied depending the individual characteristics and tolerances of the subject and the on the precise nature of the condition being treated.

In certain embodiments, a subject or patient in need of treatment may be a subject who has already shown the symptoms of an MMP-mediated condition prior to the time of administration.

In another aspect, the subject or patient will be determined to be at risk for developing an MMP-mediated condition.

Additional embodiments and advantages of the invention will become apparent from the detailed discussion, examples, and claims below.

DETAILED DESCRIPTION OF THE INVENTION

One aspect of the present invention features certain matrix metalloproteinase (MMP) inhibitors. Specifically, the present invention provides compounds of Formula (I)

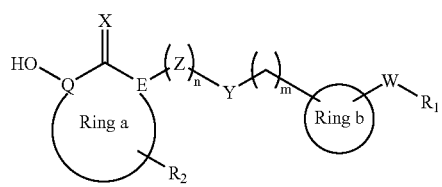

wherein

Ring a is a 6, 7, 8, or 9-membered ring selected from heteroaryl and heterocyclyl, wherein
X is O or S,
E is selected from an sp² carbon,

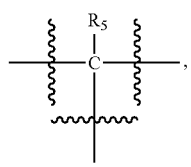

and N, wherein
$R_5$ is selected from H, hydroxy, amino, alkoxy, alkylthio, sulfonyl, $C_{1-10}$alkyl, $C_{2-6}$alkenyl, $C_{2-6}$alkynyl, aryl, heteroaryl, and heterocyclyl, and
Q is N or an sp² carbon, provided that when E is an sp² carbon, Q is N;

Ring b is selected from
aryl;
heteroaryl; and
heterocyclyl of the formula

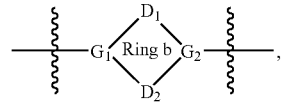

wherein
$G_1$ and $G_2$ are independently selected from N, C, and CH; and
$D_1$ and $D_2$ are each 1-3 independent members selected from CH, $CH_2$, N, S, and O, provided that when $G_1$ or $G_2$ is N, $D_1$ and $D_2$ are independently selected from CH and $CH_2$.

$R_1$ is selected from halo, nitrile, hydroxyl, thiol, amino, alkoxy, alkylthio, sulfonyl, $C_{1-10}$alkyl, $C_{2-6}$alkenyl, $C_{2-6}$alkynyl, cycloalkyl, aryl, heteroaryl, heterocyclyl, carbonyl, and —CHO;

$R_2$ is 0-2 independent members selected from halo, nitrile, hydroxyl, amino, $C_{1-10}$alkyl, $C_{2-6}$alkenyl, $C_{2-6}$alkynyl, alkoxy, alkylthio, sulfonyl, aryl, heteroaryl, heterocyclyl, —C(O)$R_3$, —C(O)O$R_3$, and —C(O)N$R_3R_4$, wherein
$R_3$ and $R_4$ are independently selected from H, $C_{1-10}$alkyl, aryl, heteroaryl, and heterocyclyl, or
$R_3$ and $R_4$ together with the N they are attached to form a 3-, 4-, 5-, 6-, or 7-membered heterocyclyl;

W is selected from a covalent bond, —(CH$_2$)$_p$—O—, —O—(CH$_2$)$_p$—, —S(O)$_p$—, —C(O)—, $C_{1-3}$alkylene, $C_{2-3}$alkenylene, $C_{2-3}$alkynylene, and 5-7 membered aliphatic ring containing one or two nitrogens, wherein p is 0, 1, or 2;

Y is selected from O, S, S(O), S(O)$_2$, —SO$_2$N(R$_6$)—, —N(R$_6$)SO$_2$—, —N(R$_6$)SO$_2$N(R$_7$)—, —N(R$_6$)CO—, —N(R$_6$)PO(OR$_8$)—, —N(SO$_2$R$_8$)—, —N(COR$_8$)—, —N(POOR$_8$R$_9$)—, —CH(OH)—,

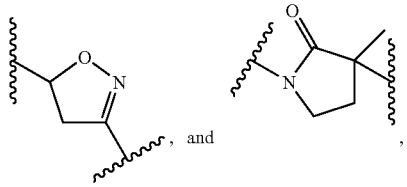

wherein
$R_6$ and $R_7$ are independently selected from H, $C_{1-10}$alkyl, alkylsulfonyl, arylsulfonyl, alkylcarbonyl, and arylcarbonyl, and
$R_8$ and $R_9$ are independently selected from $C_{1-6}$alkyl, aryl, heteroaryl, and heterocyclyl;

Z is —CH(R$_{10}$)— or —CH(R$_{10}$)CH(R$_{11}$)—, wherein
$R_{10}$ and $R_{11}$ are independently selected from H, $C_{1-6}$alkyl, $C_{2-6}$alkenyl, $C_{2-6}$alkynyl, aryl, heteroaryl, and heterocyclyl;

m is 0, 1, or 2; and n is 0 or 1 with the proviso that when n is 0, E is not N and Y is not O;

or an optical isomer, enantiomer, diastereomer, racemate, prodrug or pharmaceutically acceptable salt thereof.

In particular, ring a is selected from

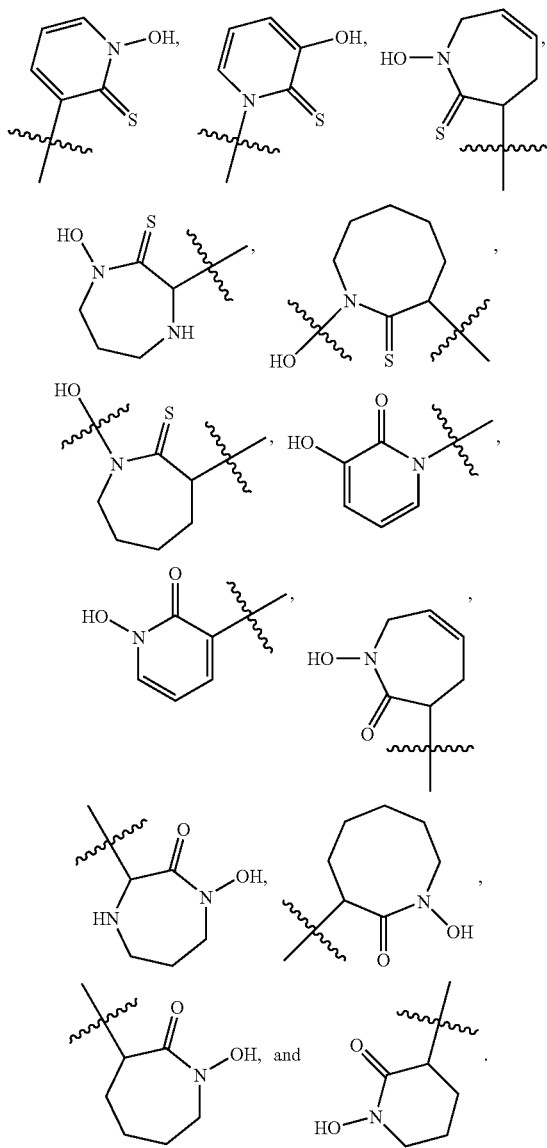

In particular, ring b is 5 or 6-membered aryl or 5 or 6-membered heteroaryl. More particularly, ring b is phenyl or

Ring b can also be fused ring aryl or fused ring heteroaryl wherein the two points of attachment are on two rings.

In particular, $R_1$ is selected from halo, alkoxy, $C_{1-10}$alkyl, aryl, heteroaryl, and heterocyclyl.

In particular, $R_2$ is 0-1 member selected from halo, $C_{1-10}$alkyl, and aryl.

In particular, Q is N.

In particular, X is O.

In particular, E is selected from an sp² carbon,

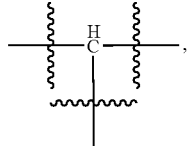

and N.

In particular, Z is —CH($R_{10}$)— wherein $R_{10}$ is H or $C_{1-6}$alkyl.

In particular, Y is selected from O, S(O)$_2$, —N($R_6$)SO$_2$—, —N(SO$_2R_8$)—, wherein $R_6$ is H or $C_{1-10}$alkyl, and $R_8$ is $C_{1-10}$alkyl.

In particular, W is selected from a covalent bond, O, —O—(CH$_2$)—, $C_{1-3}$alkylene, and $C_{2-3}$alkynylene.

In particular, m is 0 or 1.

In particular, n is 0.

In particular, n is 1.

Particularly, the present invention is directed to compounds of Formula (I), wherein Ring a is selected from

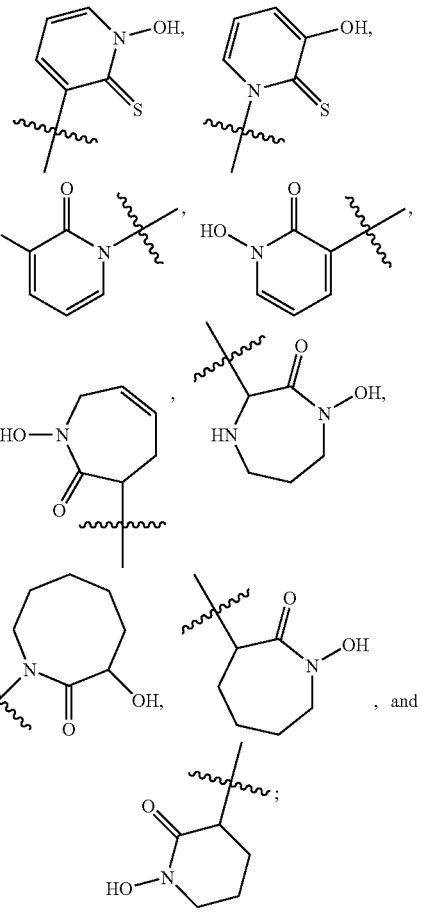

Ring b is 5 or 6-membered aryl or 5 or 6-membered heteroaryl;

$R_1$ is selected from halo, alkoxy, $C_{1-10}$alkyl, aryl, heteroaryl, and heterocyclyl.

$R_2$ is 0-1 member selected from halo, $C_{1-10}$alkyl, and aryl;

Z is —CH(R$_{10}$)— wherein R$_{10}$ is H or C$_{1-6}$alkyl;
Y is selected from O, S(O)$_2$, —N(R$_6$)SO$_2$—, and —N(SO$_2$R$_8$)—, wherein R$_6$ is H or C$_{1-10}$alkyl, and R$_8$ is C$_{1-10}$alkyl
W is selected from a covalent bond, O, —O—(CH$_2$)—, C$_{1-3}$alkylene, and C$_{2-3}$alkynylene; and
m is 0 or 1.

More particularly, the present invention is directed to compounds of Formula (I), wherein
Ring a is selected from

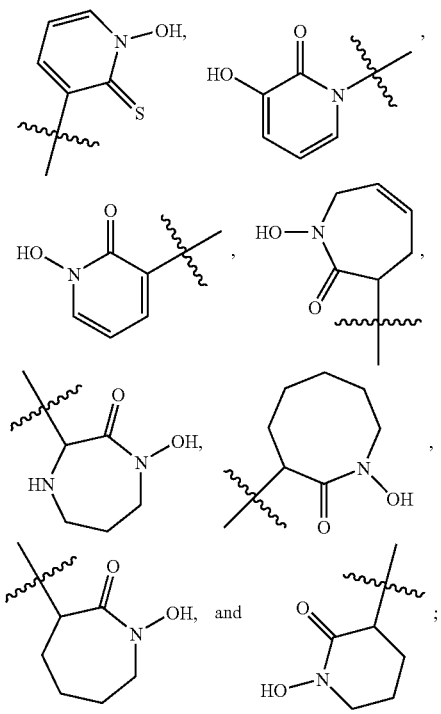

Ring b is phenyl or

R$_1$ is selected from Br, Cl, F, C$_{1-4}$alkoxy, C$_{1-4}$alkyl, phenyl,

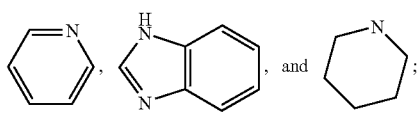

R$_2$ is selected from 0-1 member selected from Br, C$_{1-4}$alkyl, and phenyl;
Z is —CH(R$_{10}$)— wherein R$_{10}$ is H or C$_{1-4}$alkyl;
Y is selected from O, S(O)$_2$, —N(R$_6$)SO$_2$—, and —N(SO$_2$R$_8$)—, wherein R$_6$ is H or C$_{1-4}$alkyl, and R$_8$ is C$_{1-4}$alkyl;
W is selected from a covalent bond, O, —O—(CH$_2$)—, C$_{1-3}$alkylene, and —C≡C—; and
m is 0 or 1.

Specifically, W is O or a covalent bond, or ring b is phenyl, or R$_1$ is phenyl. Specifically, m is 0, or n is 0, or n is 1. More specifically, n is 1 and Z is —CH$_2$—. Specifically, Y is S(O)$_2$, —N(S(O)$_2$CH$_3$)— or —N(R$_6$)SO$_2$—, wherein R$_6$ is H or C$_{1-4}$alkyl. More specifically, n is 0. And more specifically,
Ring a is selected from

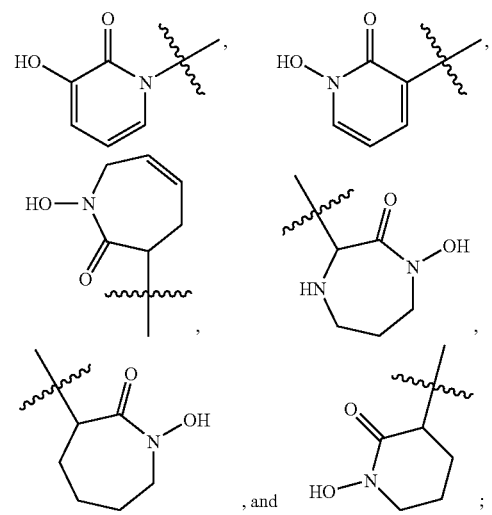

R$_1$ is selected from Ph, -Ph-Br, -Ph-Cl, -Ph-CH$_3$, -Ph-OCH$_3$, -Ph-OCF$_3$, -Ph-CF$_3$, and

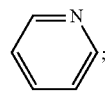

R$_2$ is selected from 0-1 member selected from C$_{1-4}$alkyl optionally substituted with

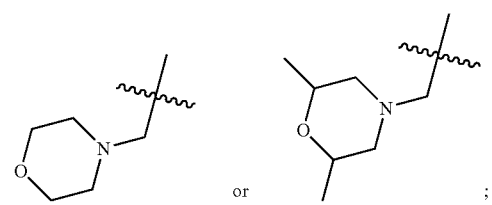

Z is —CH$_2$—;
Y is selected from S(O)$_2$, —N(R$_6$)SO$_2$—, and —N(SO$_2$R$_8$)—, wherein R$_6$ is H or C$_{1-4}$alkyl optionally substituted with oxo,

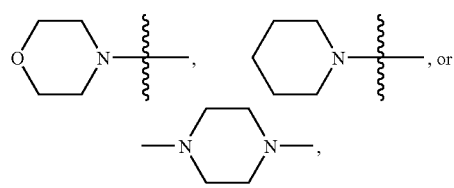

and R$_8$ is C$_{1-4}$alkyl;
W is selected from a covalent bond, O, and —C≡C—; and
m is 0.

Further, specifically, Y is selected from S(O)$_2$, —N(CH$_3$)SO$_2$—, —NH—SO$_2$—, and
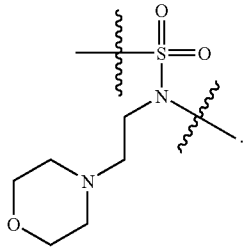
Also an embodiment of the present invention is a compound selected from:
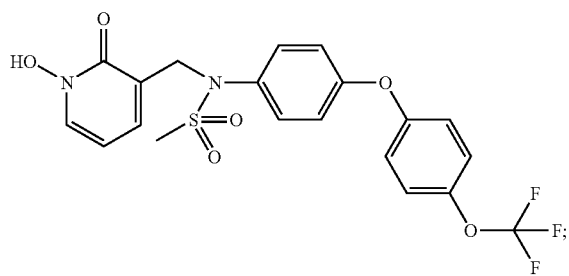
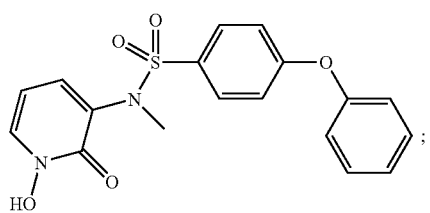
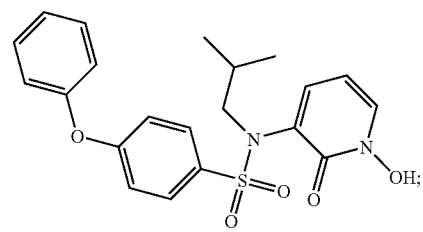
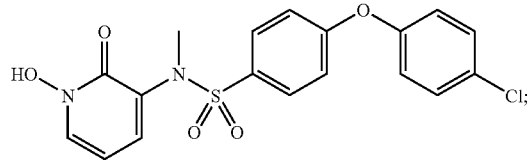
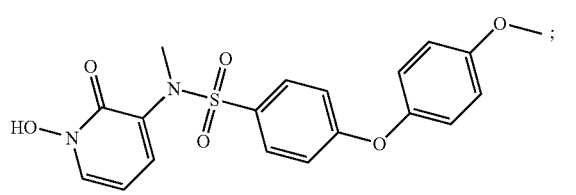
-continued
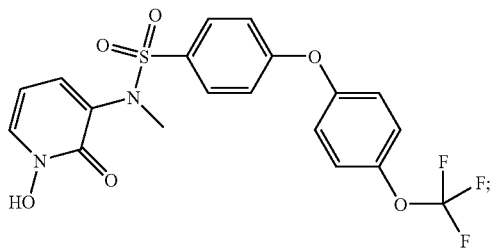
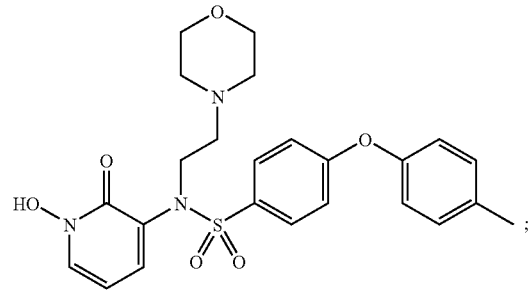
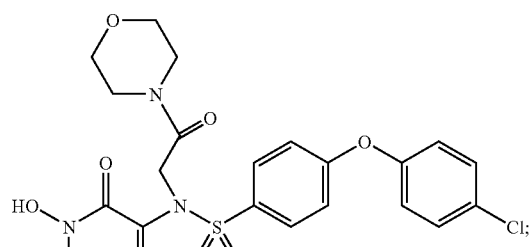
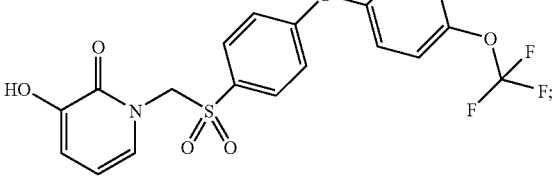
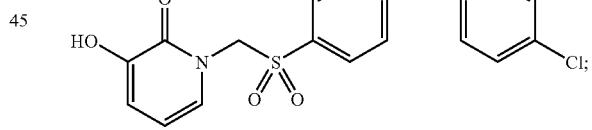
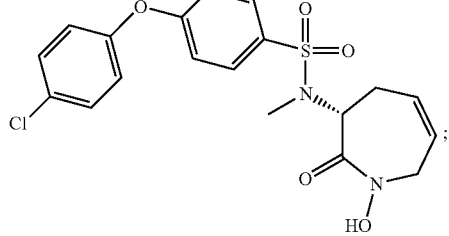

-continued
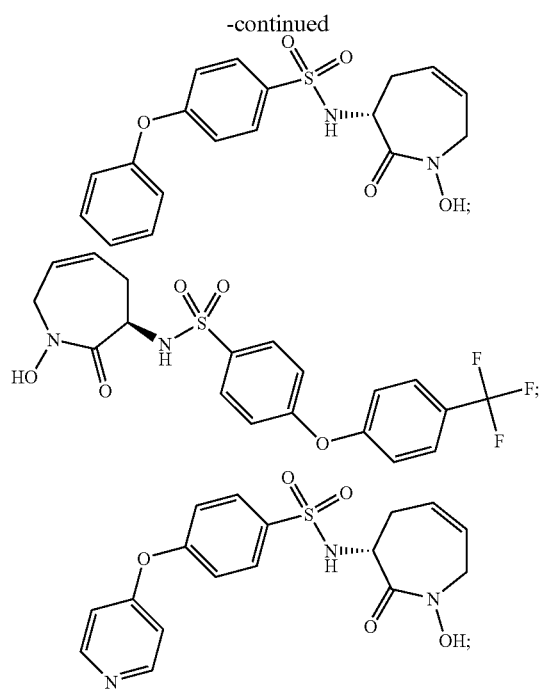
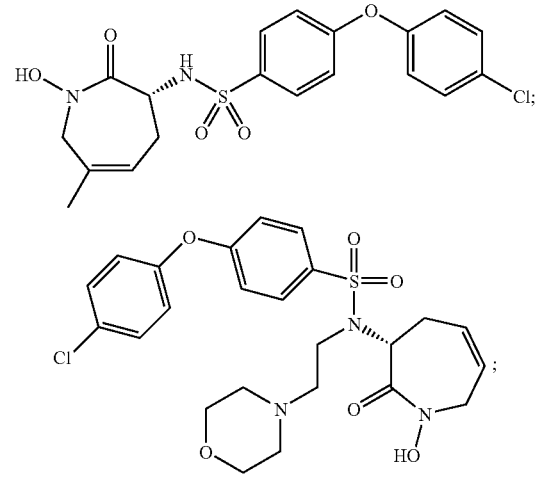
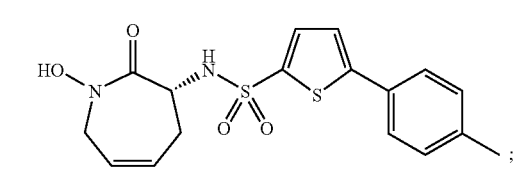
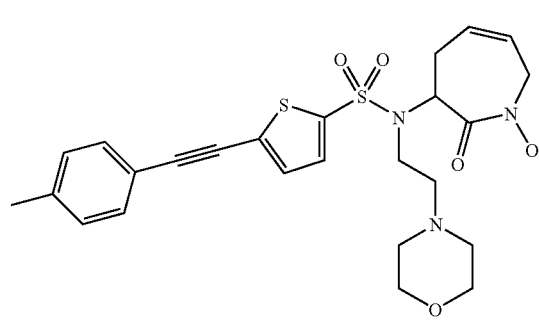
-continued
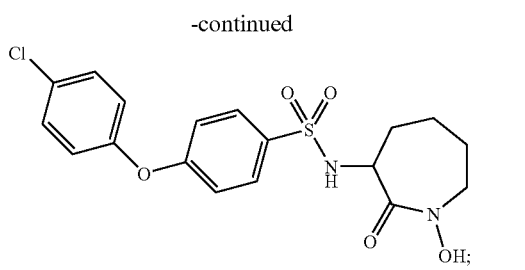
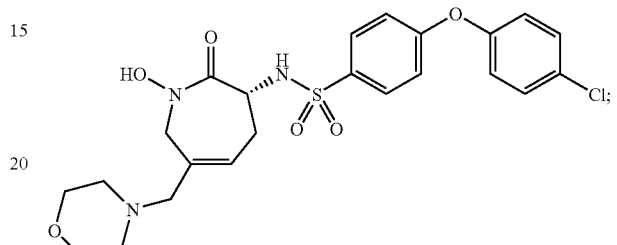
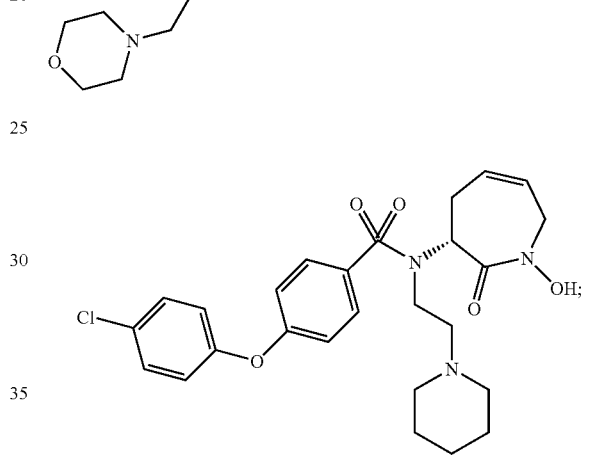
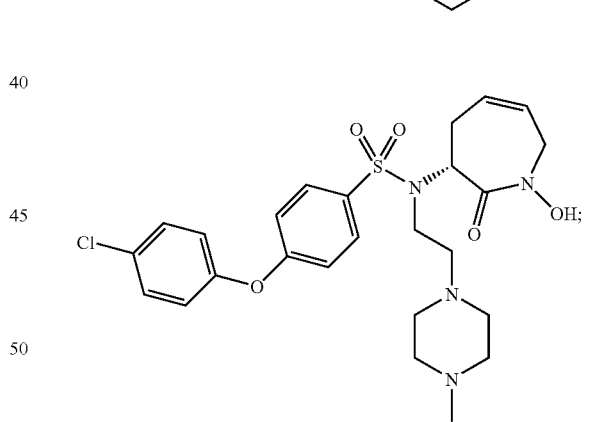
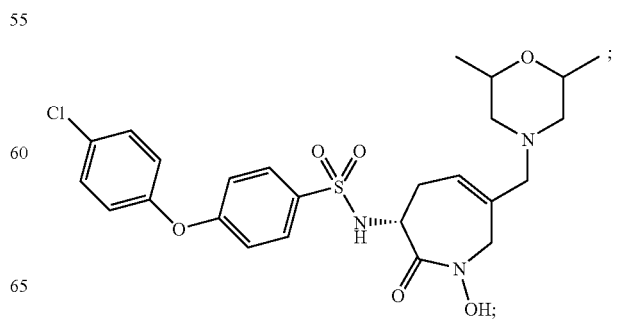

-continued

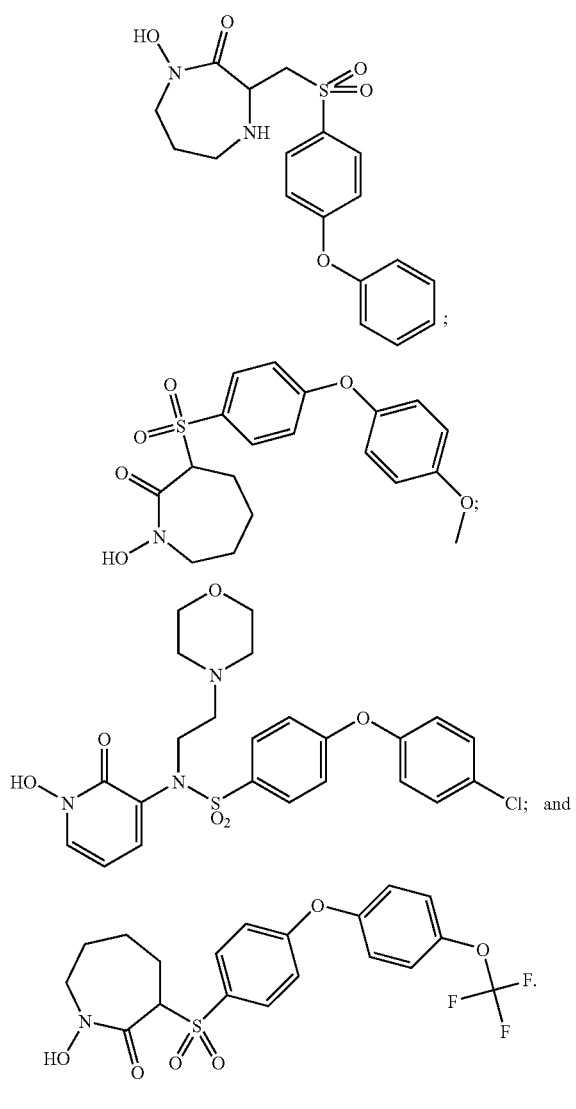

More particularly, compounds of Formula (I) of this invention are selected from:

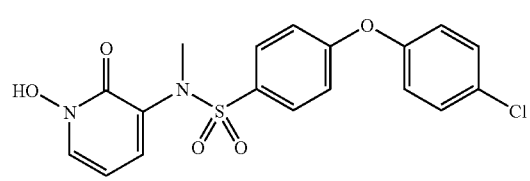

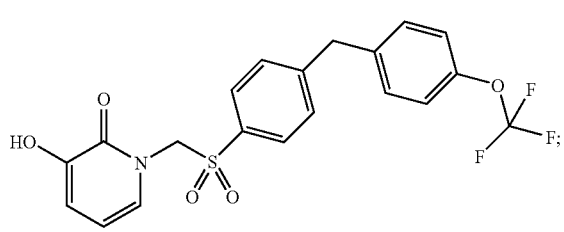

-continued

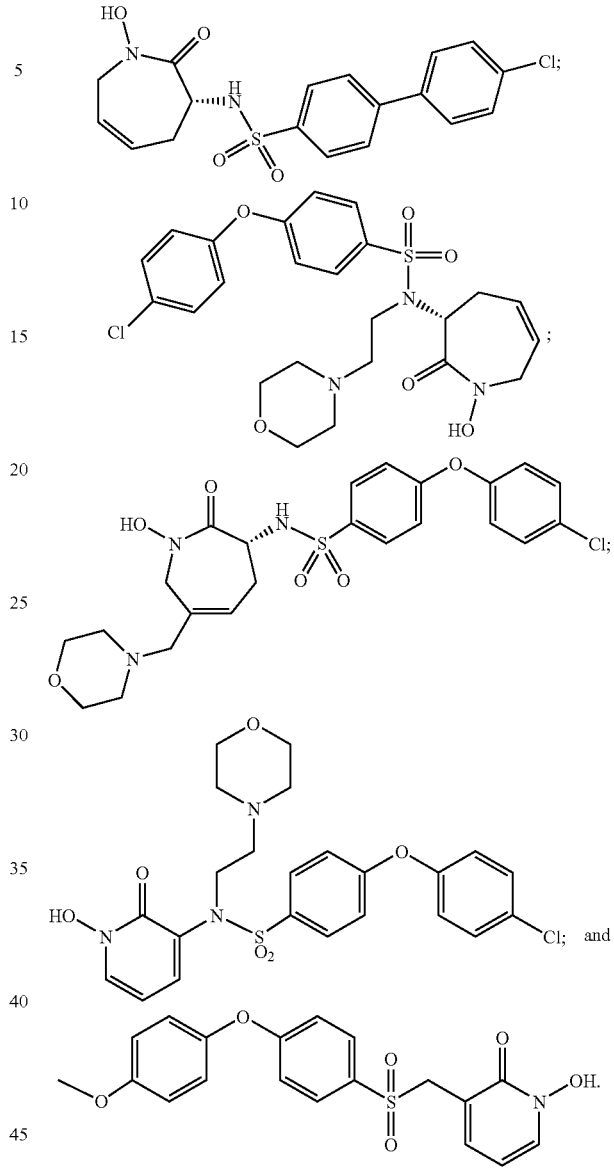

The present invention is also directed to a pharmaceutical composition comprising a compound of Formula (I) and a pharmaceutically acceptable carrier.

In another aspect, the present invention provides a method of treating a subject having a condition ameliorated by antagonizing matrix metalloproteinase in appropriate cells in the subject, which method comprises administering to the subject a therapeutically effective dose of the compound of Formula (I). More particularly, the present invention provides a method of preventing a subject having a condition ameliorated by antagonizing matrix metalloproteinase in appropriate cells in the subject, which method comprises administering to the subject a prophylactically effective dose of the compound of claim 1 either preceding or subsequent to an event anticipated to cause a condition ameliorated by antagonizing matrix metalloproteinase in appropriate cells in the subject. Particularly, the condition is selected from vascular and myocardial tissue morphogenesis, cancer, cardiovascular diseases, inflammatory diseases, acute and chronic CNS disorders, neurovascular disorders, neurodegenerative diseases, demylinating diseases, movement disorders, and associated symptoms or complications thereof. More particularly, the condition is selected from ischemic or hemorrhagic stroke, Parkinson's disease, Alzheimer's disease, cerebral amyloid angiopathy, vascular dementia, headaches, migraine, traumatic brain injury, multiple sclerosis, edema, atherosclerotic plaque rupture, aneurysm, osteoarthritis, rheumatoid arthritis, gastric ulcers, pulmonary hypertension, chronic obstructive pulmonary disease, inflammatory bowel disease, periodontal disease, skin ulcers, liver fibrosis, emphysema, Marfan's syndrome, and associated symptoms or complications thereof. Further, the compound of Formula (I), or an optical isomer, enantiomer, diastereomer, racemate, prodrug or pharmaceutically acceptable salt thereof, is administered in combination administration with one or more other compounds or therapeutic agents. Furthermore, the subject is a human.

In one embodiment of the present invention, the therapeutically effective amount of a compound of Formula (I) in the above methods is in a range of from about 0.001 mg/kg of body weight to about 200 mg/kg of body weight of the subject.

The present invention also includes a kit comprising one or more therapeutically effective dosage forms of the pharmaceutical composition comprising a compound of Formula (I) and a pharmaceutically acceptable carrier.

In yet another aspect, the present invention provides an intermediate in preparing a compound of Formula (I), said intermediate having the formula

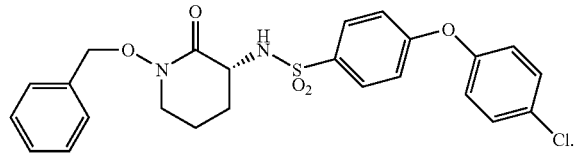

DEFINITIONS

Unless otherwise noted, under standard nomenclature used throughout this disclosure the terminal portion of the designated side chain is described first, followed by the adjacent functionality toward the point of attachment.

As used herein, the following terms shall have the meanings as set forth in the following paragraphs:

The term "independently," when in reference to chemical substituents, shall mean that when more than one substituent exists, the substituents may be the same or different.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Designated numbers of carbon atoms (e.g., $C_{1-8}$) shall refer independently to the number of carbon atoms in an alkyl or cycloalkyl moiety or to the alkyl portion of a larger substituent in which alkyl appears as its prefix root.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized with materials and by techniques known in the art as well as those methods set forth herein.

Unless otherwise noted, when a particular group is "substituted" (e.g., alkyl, phenyl, aryl, heteroalkyl, heteroaryl), that group may have one or more substituents, preferably from one to five substituents, more preferably from one to three substituents, most preferably from one to two substituents, independently selected from the list of substituents.

As used herein, the term "alkyl," whether used alone or as part of a substituent group, include straight and branched chains. For example, alkyl radicals include methyl, ethyl, propyl, isopropyl, butyl, isobutyl, sec-butyl, t-butyl, pentyl and the like. Unless otherwise noted, "$C_{1-4}$alkyl" means a carbon chain composition of 1-4 carbon atoms. Unless otherwise stated, the alkyl group will contain 1-20 carbon atoms. Unless otherwise stated, the alkyl group may be optionally substituted with one or more groups such as halogen, OH, CN, mercapto, nitro, amino, $C_1$-$C_8$-alkyl, $C_1$-$C_8$-alkoxyl, $C_1$-$C_8$-alkylthio, $C_1$-$C_8$-alkyl-amino, di($C_1$-$C_8$-alkyl)amino, (mono-, di-, tri-, and per-) halo-alkyl, formyl, carboxy, alkoxycarbonyl, $C_1$-$C_8$-alkyl-CO—O—, $C_1$-$C_8$-alkyl-CO—NH—, carboxamide, hydroxamic acid, sulfonamide, sulfonyl, thiol, aryl, aryl($c_1$-$c_8$)alkyl, heterocyclyl, and heteroaryl.

"Alkenyl" means a partially unsaturated alkyl radical or linking group substituent having at least at least two carbon atoms and one double bond derived by the removal of one hydrogen atom from each of two adjacent carbon atoms in the chain. Atoms may be oriented about the double bond in either the cis (E) or trans (Z) conformation. The term includes, without limitation, methylidene, vinyl, vinylidene, allyl, allylidene, propylidene, isopropenyl, iso-propylidene, prenyl, prenylene (3-methyl-2-butenylene), methallyl, methallylene, allylidene (2-propenylidene), crotylene (2-butenylene), and the like. An alkenyl substituent may be attached to a core molecule via a terminal carbon atom or via a carbon atom within the chain. Similarly, any number of substituent variables may be attached to an alkenyl substituent when allowed by available valences. The term "lower alkenyl" means an alkenyl substituent having from 2-4 carbon atoms.

"Alkynyl" means a partially unsaturated alkyl radical or linking group substituent having at least two carbon atoms and one triple bond derived by the removal of two hydrogen atom from each of two adjacent carbon atoms in the chain. The term includes, without limitation, ethinyl, ethinylidene, propargyl, propargylidene and the like. An alkynyl substituent may be attached to a core molecule via a terminal carbon atom or via a carbon atom within the chain. Similarly, any number of substituent variables may be attached to an alkynyl substituent when allowed by available valences. The term "lower alkynyl" means an alkynyl substituent having from 2-4 carbon atoms.

"Alkoxy" or "alkoxyl" means —O-alkyl, —O-alkenyl, or —O-alkynyl; unless otherwise stated, it will have 1-8 carbon atoms.

"Alkylene" means straight, branched, or cyclic alkyl diradical, optionally substituted with one to five, preferably one to three groups including, but not limited to, optionally substituted $C_{1-3}$alkyl and F.

"Alkenylene" means straight or branched alkenyl diradical, optionally substituted with one to five, preferably one to three groups including, but not limited to, optionally substituted $C_{1-3}$alkyl and F.

"Alkynylene" means straight or branched alkynyl diradical, optionally substituted with one to five, preferably one to three groups including, but not limited to, optionally substituted $C_{1-3}$alkyl and F.

"Halogen" or "halo" means fluorine, chlorine, bromine or iodine.

"Aryl" or "Ar," whether used alone or as part of a substituent group, is a carbocyclic aromatic radical including, but not limited to, phenyl, 1- or 2-naphthyl and the like. The carbocyclic aromatic radical may be substituted by independent replacement of 1 to 5 of the hydrogen atoms thereon with halogen, OH, CN, mercapto, nitro, amino, $C_1$-$C_8$-alkyl, $C_1$-$C_8$-alkoxyl, $C_1$-$C_8$-alkylthio, $C_1$-$C_8$-alkyl-amino, di($C_1$-$C_8$-alkyl)amino, (mono-, di-, tri-, and per-) halo-alkyl, formyl, carboxy, alkoxycarbonyl, $C_1$-$C_8$-alkyl-CO—O—, $C_1$-$C_8$-alkyl-CO—NH—, or carboxamide. Illustrative aryl radicals include, for example, phenyl, naphthyl, biphenyl, fluorophenyl, difluorophenyl, benzyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, tolyl, xylyl, dimethylcarbamylphenyl and the like. "Ph" or "PH" denotes phenyl. "Bn" means benzyl.

The term "heteroaryl" refers to a monovalent heteroaromatic radical derived by the removal of one hydrogen atom from a single atom of a parent heteroaromatic ring system. Typical heteroaryl groups include monocyclic and bicyclic systems where one or both rings is heteroaromatic Heteroaromatic rings may contain 1-4 heteroatoms selected from O, N, and S. Examples include but are not limited to, radicals derived from carbazole, imidazole, indazole, indole, indolizine, isoindole, isoquinoline, isothiazole, isoxazole, naphthyridine, oxadiazole, oxazole, purine, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, "heteroaryl" is substituted. For instance, "heteroaryl" can be substituted with, e.g., optionally substituted $C_{1-6}$alkyl, $C_{2-6}$alkenyl, $C_{2-6}$alkynyl, halo, nitro, hydroxyl, ethynyl, —CN, aryl, heteroaryl, heterocyclyl, —$SO_3H$, —C(O)OH, —C(O)O—$C_{1-4}$alkyl, —C(O)NR'R"—OR', —SR'—C(O)R', —N(R')(R"), —S(O)$_2$—R', and —S(O)$_2$—N(R')(R"), wherein R' and R" are independently selected from H, $C_{1-6}$-alkyl, aryl, heteroaryl, and/or heterocyclyl.

The term "heterocyclyl" or "heterocycle" is a 3- to 8-member saturated, or partially saturated single or fused ring system which consists of carbon atoms and from 1 to 6 heteroatoms selected from N, O and S. The heterocyclyl group may be attached at any heteroatom or carbon atom which results in the creation of a stable structure. Example of heterocyclyl groups include, but are not limited to, 2-imidazoline, imidazolidine; morpholine, oxazoline, 2-pyrroline, 3-pyrroline, pyrrolidine, pyridone, pyrimidone, piperazine, piperidine, indoline, tetrahydrofuran, 2-pyrroline, 3-pyrroline, 2-imidazoline, 2-pyrazoline, indolinone. A "heterocyclyl" can be a partially unsaturated ring such as 2-pyrroline, 3-pyrroline, 2-imidazoline, 2-pyrazoline, indolinone, or. "Heterocyclyl" being connected to N(1), as shown in Formula (I), through a ring carbon atom that is double-bonded to a ring nitrogen can include, but is not limited to 4,5-dihydrothiazole, 3-psuedoindolone, and pyrimidone. In some embodiments, "heterocyclyl" or "heterocycle" are independently substituted. For instance, "heterocyclyl" or "heterocycle" can be substituted with, e.g., optionally substituted $C_{1-6}$alkyl, $C_{2-6}$alkenyl, $C_{2-6}$alkynyl, halo, nitro, hydroxyl, ethynyl, —CN, aryl, heteroaryl, heterocyclyl, —$SO_3H$, —C(O)OH, —C(O)O—$C_{1-4}$alkyl, C(O)NR'R", —OR', —SR', —C(O)R', —N(R')(R"), —S(O)$_2$—R', and —S(O)$_2$—N(R')(R"), wherein R' and R" are independently selected from H, $C_{1-6}$-alkyl, aryl, heteroaryl, and/or heterocyclyl.

The term "base" means a chemical species or molecular entity having an available pair of electrons capable of forming a covalent bond with a hydron (proton) or with the vacant orbital of some other species.

Where the compounds according to this invention have at least one stereogenic center, they may accordingly exist as enantiomers. Where the compounds possess two or more stereogenic centers, they may additionally exist as diastereomers. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their components enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compositions specifically disclosed or with a composition which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid.

Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following; acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases which may be used in the preparation of pharmaceutically acceptable salts include the following: acids; including acetic acid, 2,2-dichlorolacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hipuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinc acid, nitric acid, oleic acid, orotic acid, oxalic acid, palmitric acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases; including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

As used herein, the term "composition" is intended to encompass a product comprising the specified ingredients in the specified amounts, as well as any product which results, directly or indirectly, from combinations of the specified ingredients in the specified amounts.

The terms "subject" or "patient" are used herein interchangeably and as used herein, refer to any animal or artificially modified animal having a disorder that can be ameliorated by antagonizing matrix metalloproteinases. In a preferred embodiment, the subject is a human. More particularly, the subject is a human being who is the object of treatment, observation or experiment.

The term "treating" or "treatment" as used herein, refers to actions that cause any indicia of success in the prevention or amelioration of an injury, pathology, symptoms or condition, including any objective or subjective parameters such as abatement; remission; diminishing of symptoms or making the injury, pathology, or condition more tolerable to the patient; slowing in the rate of degeneration or decline; making the final point of degeneration less debilitating; or improving a subject's physical or mental well-being. Thus the term "treatment" or "to treat" is intended to include any action that improves, prevents, reverses, arrests, abates, or inhibits the pathological process of a condition that can be ameliorated by antagonizing matrix metalloproteinases as defined and used herein. The treatment or amelioration of symptoms can be based on objective or subjective parameters; including the results of a physical examination, neurological examination, and/or psychiatric evaluations.

As used herein, the term "concomitant administration" or "combination administration" of a compound, therapeutic agent or known drug with a compound of the present invention means administration of the drug and the one or more compounds at such time that both the known drug and the compound will have a therapeutic effect. In some cases this therapeutic effect will be synergistic. Such concomitant administration can involve concurrent (i.e. at the same time), prior, or subsequent administration of the drug with respect to the administration of a compound of the present invention. A person of ordinary skill in the art would have no difficulty determining the appropriate timing, sequence and dosages of administration for particular drugs and compositions of the present invention.

Accordingly, the term "treating" or "treatment" includes the administration of the compounds or agents of the present invention to treat, prevent, reverse, arrest, abate, or inhibit a condition that can be ameliorated by antagonizing matrix metalloproteinases. In some instances, treatment with the compounds of the present invention will prevent, inhibit, or arrest the progression of a neurodegenerative or movement disorder. Examples of conditions treatable by the instant pharmaceutical composition include, without limitation, ischemic or hemorrhagic stroke, Parkinson's disease, Alzheimer's disease, cerebral amyloid angiopathy, vascular dementia, headaches, migraine, traumatic brain injury, multiple sclerosis, edema, atherosclerotic plaque rupture, aneurysm, osteoarthritis, rheumatoid arthritis, gastric ulcers, pulmonary hypertension, chronic obstructive pulmonary disease, inflammatory bowel disease, periodontal disease, skin ulcers, liver fibrosis, emphysema, Marfan's syndrome, and associated symptoms or complications thereof.

The term "therapeutic effect" as used herein, refers to the treatment, inhibition, abatement, reversal, or prevention of a condition that can be ameliorated by antagonizing matrix metalloproteinases, the effects or symptoms of such condition, or side effects or complications of such condition in a subject.

The terms "a therapeutically effective amount" or "a therapeutically effective dose" are used interchangeably and, as used herein, mean a sufficient amount or dose of one or more of the compounds or compositions of the invention to produce a therapeutic effect, as defined above, in a subject or patient in need of such; treatment, inhibition, abatement, reversal, or prevention of that can be ameliorated by antagonizing matrix metalloproteinases, the effects or symptoms of such condition, or side effects of such condition in a subject. The range of doses required for these different therapeutic effects will differ according to the characteristics of the subject or patient and the precise nature of the condition being treated.

In one embodiment, the therapeutically and/or prophylactically effective dose is a dose sufficient to deliver from about 0.001 mg/kg of body weight to about 200 mg/kg of body weight of the instant pharmaceutical composition. In another embodiment, the therapeutically and/or prophylactically effective dose is a dose sufficient to deliver from about 0.05 mg/kg of body weight to about 50 mg/kg of body weight. More specifically, in one embodiment, oral doses range from about 0.05 mg/kg to about 100 mg/kg daily. In another embodiment, oral doses range from about 0.05 mg/kg to about 50 mg/kg daily, and in a further embodiment, from about 0.05 mg/kg to about 20 mg/kg daily. In yet another embodiment, infusion doses range from about 1.0 mg/kg/min to about 10 mg/kg/min of inhibitor, admixed with a pharmaceutical carrier over a period ranging from about several minutes to about several days. In a further embodiment, for topical administration, the instant compound can be combined with a pharmaceutical carrier at a drug/carrier ratio of from about 0.001 to about 0.1.

The term "pharmaceutical dosage form" as that term is used herein, shall refer to a form of one or more of the compounds or compositions of this invention along with pharmaceutically acceptable excipients to produce a formulation suitable for administration to a subject. The form may be adapted for administration by any appropriate route including, but not limited to; oral, both immediate and delayed release, intravenous (I.V.), transdermal, intramuscular, intraventricular or nasal and may comprise; tablets, pills, capsules, semisolids, powders, sustained release formulations, solutions, suspensions, emulsions, syrups, elixirs, aerosols, or any other appropriate compositions.

This invention will be better understood by reference to the Experimental Details which follow, but those skilled in the art will readily appreciate that these are only illustrative of the invention as described more fully in the claims which follow thereafter. Additionally, throughout this application, various publications are cited. The disclosure of these publications is hereby incorporated by reference into this application to describe more fully the state of the art to which this invention pertains.

Dosage Regimens

The present invention provides methods of treating a condition that can be ameliorated by antagonizing matrix metalloproteinases in a human subject or patient using the arylindenopyrimidine compounds or compositions of the invention. The dosage schedule and amounts effective for this use, i.e., the dosing or dosage regimen, will depend on a variety of factors including the precise nature of the condition, disease or injury, the patient's physical status, weight, age and the like. In calculating the dosage regimen for a patient, the mode of administration is also taken into account.

The pharmaceutical compounds and compositions of the invention may be administered, for example, at a dosage of from about 400-3000 mg/day in a 70 kg human, preferably from 450-2500 mg/day in a 70 kg human, more preferably from about 500-2000 mg/day in a 70 kg human, or even more preferably from about 550-1500 mg/day in a 70 kg human, or most preferably from about 600-1200 mg/day in a 70 kg human. These dosages, however, may be varied depending the individual characteristics and tolerances of the subject and the on the precise nature of the condition being treated.

Based on this disclosure, a person of ordinary skill in the art will be able, without undue experimentation, having regard to that skill, to determine a therapeutically effective dose or amount of a particular substituted carbamate compound of the invention for treating epilepsy and for producing a clinically significant anti epileptogenic effect. (see, e.g., Lieberman, Pharmaceutical Dosage Forms (Vols. 1-3, 1992); Lloyd, 1999, The art, Science and Technology of Pharmaceutical Compounding; and Pickar, 1999, Dosage Calculations).

A therapeutically effective dose is also one in which any toxic or detrimental side effects of the active agent is outweighed in clinical terms by therapeutically beneficial effects. It is to be further noted that for each particular subject, specific dosage regimens should be evaluated and adjusted over time according to the individual need and professional judgment of the person administering or supervising the administration of the compounds. It is also expected that the compositions of this invention could be initiated at a low or moderate dose and then increased to a fully therapeutically effective dose and blood level over a period of time.

For treatment purposes, the compositions or compounds disclosed herein can be administered to the subject, for example, in a single bolus delivery, via continuous delivery over an extended time period, or in a repeated administration protocol (e.g., by an hourly, daily or weekly, repeated administration protocol). The pharmaceutical formulations of the present invention can be administered, for example, one or more times daily, 3 times per week, or weekly. In one embodiment of the present invention, the pharmaceutical formulations of the present invention are orally administered once or twice daily.

In this context, a therapeutically effective dosage of the biologically active agent(s) can include repeated doses within a prolonged treatment regimen that will yield clinically significant results to prevent, reverse, arrest, or inhibit the epileptogenesis. Determination of effective dosages in this context is typically based on animal model studies followed up by human clinical trials and is guided by determining effective dosages and administration protocols that significantly reduce the occurrence or severity of targeted exposure symptoms or conditions in the subject. Suitable models in this regard include, for example, murine, rat, porcine, feline, non-human primate, and other accepted animal model subjects known in the art. Alternatively, effective dosages can be determined using in vitro models (e.g., immunologic and histopathologic assays). Using such models, only ordinary calculations and adjustments are typically required to determine an appropriate concentration and dose to administer a therapeutically effective amount of the biologically active agent(s) (e.g., amounts that are intranasally effective, transdermally effective, intravenously effective, or intramuscularly effective to elicit a desired response).

In an exemplary embodiment of the present invention, unit dosage forms of the compounds are prepared for standard administration regimens. In this way, the composition can be subdivided readily into smaller doses at the physician's direction. For example, unit dosages can be made up in packeted powders, vials or ampoules and preferably in capsule or tablet form.

The active compound present in these unit dosage forms of the composition can be present in an amount of, for example, from about 25 mg to about 800 mg or preferably in unit dosage amounts of about 50, 100, 200 250, 400, 450, 500, and 600 mg of one or more of the compounds of the invention, for single or multiple daily administration, according to the particular need of the patient.

Pharmaceutical Compositions

The present invention comprises pharmaceutical compositions containing one or more compounds of Formula (I) with a pharmaceutically acceptable carrier.

Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed.

If desired, tablets may be sugar coated or enteric coated by standard techniques. For parenteral use, the carrier will usually comprise sterile water, through other ingredients, for example, for purposes such as aiding solubility or for preservation, may be included. Injectable suspensions may also be prepared, in which case appropriate liquid carriers, suspending agents and the like may be employed.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 10 mg to about 1000 mg of one or more compounds of Formula 1 or Formula 2 and preferably unit doses of from about 25 mg to about 800 mg and more preferably in unit doses of about; 50 mg, 100 mg, 250 mg, 400 mg, 450 mg, 500 mg and 600 mg.

The pharmaceutical compositions may be administered at a dosage of from about 400-3000 mg/day in a 70 kg human, preferably from 450-2500 mg/day in a 70 kg human, more preferably from about 500-2000 mg/day in a 70 kg human, or even more preferably from about 550-1500 mg/day in a 70 kg human, or most preferably from about 600-1200 mg/day in a 70 kg human. The dosages, however, may be varied depending upon the requirements of the patient, the severity of the condition being treated and the compound being employed.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

Preferably these compositions are in unit dosage forms from such as tablets, pills, capsules, powders, granules, sterile parenteral solutions or suspensions, metered aerosol or liquid sprays, drops, ampoules, auto injector devices or suppositories; for oral, parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 25 mg to about 800 mg of the active ingredient of the present invention.

The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like.

For parenteral administration, sterile suspensions and solutions are desired. Isotonic preparations which generally contain suitable preservatives are employed when intravenous administration is desired.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a compound to treat or prevent a given condition.

One skilled in the art will further recognize that human clinical trails including first-in-human, dose ranging and efficacy trials, in healthy patients and/or those suffering from a given disorder, may be completed according to methods well known in the clinical and medical arts.

In general, the arylindenopyrimidine compounds of the present invention can be administered as pharmaceutical compositions by any method known in the art for administering therapeutic drugs including oral, buccal, topical, systemic (e.g., transdermal, intranasal, or by suppository), or parenteral (e.g., intramuscular, subcutaneous, or intravenous injection.) Administration of the compounds directly to the nervous system can include, for example, administration to intracerebral, intraventricular, intracerebroventricular, intrathecal, intracisternal, intraspinal or peri-spinal routes of administration by delivery via intracranial or intravertebral needles or catheters with or without pump devices.

Compositions can take the form of tablets, pills, capsules, semisolids, powders, sustained release formulations, solutions, suspensions, emulsions, syrups, elixirs, aerosols, or any other appropriate compositions; and comprise at least one compound of this invention in combination with at least one pharmaceutically acceptable excipient. Suitable excipients are well known to persons of ordinary skill in the art, and they, and the methods of formulating the compositions, can be found in such standard references as Alfonso A R: *Remington's Pharmaceutical Sciences,* 17th ed., Mack Publishing Company, Easton Pa., 1985, the disclosure of which is incorporated herein by reference in its entirety and for all purposes. Suitable liquid carriers, especially for injectable solutions, include water, aqueous saline solution, aqueous dextrose solution, and glycols.

The arylindenopyrimidine compounds can be provided as aqueous suspensions. Aqueous suspensions of the invention can contain an arylindenopyrimidine compound in admixture with excipients suitable for the manufacture of aqueous suspensions. Such excipients can include, for example, a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate).

The aqueous suspension can also contain one or more preservatives such as ethyl or n-propyl p-hydroxybenzoate, one or more coloring agents, one or more flavoring agents, and one or more sweetening agents, such as sucrose, aspartame or saccharin. Formulations can be adjusted for osmolarity.

Oil suspensions for use in the present methods can be formulated by suspending a carbamate compound in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these.

Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compound of choice, alone or in combination with other suitable components can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations of the present invention suitable for parenteral administration, such as, for example, by intraarticular (in the joints), intravenous, intramuscular, intradermal, intraperitoneal, intraventricular and subcutaneous routes, can include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter.

Where the compounds are sufficiently soluble they can be dissolved directly in normal saline with or without the use of suitable organic solvents, such as propylene glycol or polyethylene glycol. Dispersions of the finely divided compounds can be made-up in aqueous starch or sodium carboxymethyl cellulose solution, or in suitable oil, such as arachis oil. These formulations can be sterilized by conventional, well-known sterilization techniques. The formulations can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The concentration of a carbamate compound in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally acceptable diluents or solvent, such as a solution of 1,3-butanediol.

These formulations can be presented in unit-dose or multi-dose sealed containers, such as ampoules and vials. Injection solutions and suspensions can be prepared from sterile powders, granules, and tablets of the kind previously described.

An arylindenopyrimidine compound suitable for use in the practice of this invention can be and is preferably administered orally. The amount of a compound of the present invention in the composition can vary widely depending on the type of composition, size of a unit dosage, kind of excipients, and other factors well known to those of ordinary skill in the art. In general, the final composition can comprise, for example, from 1.0% percent by weight (% w) to 90% w of the carbamate compound, preferably 10% w to 75% w, with the remainder being the excipient or excipients.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, dragees, capsules, liquids, lozenges, gels, syrups, slurries, suspensions, etc. suitable for ingestion by the patient.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions.

Pharmaceutical preparations for oral use can be obtained through combination of the compounds of the present invention with a solid excipient, optionally grinding a resulting mixture, and processing the mixture of granules, after adding suitable additional compounds, if desired, to obtain tablets or dragee cores. Suitable solid excipients are carbohydrate or protein fillers and include, but are not limited to sugars, including lactose, sucrose, mannitol, or sorbitol; starch from corn, wheat, rice, potato, or other plants; cellulose such as methyl cellulose, hydroxymethyl cellulose, hydroxypropylmethyl-cellulose or sodium carboxymethylcellulose; and gums including arabic and tragacanth; as well as proteins such as gelatin and collagen.

If desired, disintegrating or solubilizing agents can be added, such as the cross-linked polyvinyl pyrrolidone, agar, alginic acid, or a salt thereof, such as sodium alginate. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers.

Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compounds of the present invention can also be administered in the form of suppositories for rectal administration of the drug. These formulations can be prepared by mixing the drug with a suitable non-irritating excipient that is solid at ordinary temperatures but liquid at the rectal temperatures and will therefore melt in the rectum to release the drug. Such materials are cocoa butter and polyethylene glycols.

The compounds of the present invention can also be administered by intranasal, intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

The compounds of the present invention can be delivered transdermally, by a topical route, formulated as applicator sticks, solutions, suspensions, emulsions, gels, creams, ointments, pastes, jellies, paints, powders, and aerosols.

Encapsulating materials can also be employed with the compounds of the present invention and the term "composition" can include the active ingredient in combination with an encapsulating material as a formulation, with or without other carriers. For example, the compounds of the present invention can also be delivered as microspheres for slow release in the body. In one embodiment, microspheres can be administered via intradermal injection of drug (e.g., mifepristone)-containing microspheres, which slowly release subcutaneously (see Rao, J. Biomater Sci. Polym. Ed. 7:623-645, 1995; as biodegradable and injectable gel formulations (see, e.g., Gao, Pharm. Res. 12:857-863, 1995); or, as microspheres for oral administration (see, e.g., Eyles, J. Pharm. Pharmacol. 49:669-674, 1997). Both transdermal and intradermal routes afford constant delivery for weeks or months. Cachets can also be used in the delivery of the compounds of the present invention.

The compositions of this invention can be administered in a variety of oral dosage form adapted for slow or controlled release. For example, the composition can be placed in an insoluble capsule with a hole at one end and a fluid absorbing distensible composition within the capsule opposite the perforated end. After administration, the fluid absorbing composition absorbs water from the patient's GI tract and swells and forces the active drug out through the perforation at a known and controllable rate. Many other delayed release or controlled release dosage forms known in the art can also be used in conjunction with the methods and compositions of this invention.

In another embodiment, the compounds of the present invention can be delivered by the use of liposomes which fuse with the cellular membrane or are endocytosed, i.e., by employing ligands attached to the liposome that bind to surface membrane protein receptors of the cell resulting in endocytosis. By using liposomes, particularly where the liposome surface carries ligands specific for target cells, or are otherwise preferentially directed to a specific organ, one can focus the delivery of the carbamate compound into target cells in vivo. (See, e.g., Al-Muhammed, J. Microencapsul. 13:293-306, 1996; Chonn, Curr. Opin. Biotechnol. 6:698-708, 1995; Ostro, Am. J. Hosp. Pharm. 46:1576-1587, 1989).

In other cases, the preferred preparation can be a lyophilized powder which can contain, for example, any or all of the following: 1 mM-50 mM histidine, 0.1%-2% sucrose, 2%-7% mannitol, at a pH range of 4.5 to 5.5, that is combined with buffer prior to use.

The pharmaceutical formulations of the invention can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms.

Pharmaceutically acceptable salts and esters refer to salts and esters that are pharmaceutically acceptable and have the desired pharmacological properties. Such salts include salts that may be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N methylglucamine, and the like.

Pharmaceutically acceptable salts can also include acid addition salts formed from the reaction of amine moieties in the parent compound with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds. When there are two acidic groups present, a pharmaceutically acceptable salt or ester may be a mono-acid-mono-salt or ester or a di-salt or ester; and similarly where there are more than two acidic groups present, some or all of such groups can be salified or esterified.

Compounds named in this invention can be present in unsalified or unesterified form, or in salified and/or esterified form, and the naming of such compounds is intended to include both the original (unsalified and unesterified) compound and its pharmaceutically acceptable salts and esters. The present invention includes pharmaceutically acceptable salt and ester forms of Formula (I). More than one crystal form of an enantiomer of Formula (I) can exist and as such are also included in the present invention.

A pharmaceutical composition of the invention can optionally contain, in addition to an arylindenopyrimidine compound, at least one other therapeutic agent useful in the treatment of a disease or condition that can be ameliorated by antagonizing matrix metalloproteinases.

Methods of formulating pharmaceutical compositions have been described in numerous publications such as *Pharmaceutical Dosage Forms: Tablets*. Second Edition. Revised and Expanded. Volumes 1-3, edited by Lieberman et al; *Pharmaceutical Dosage Forms*: Parenteral Medications. Volumes 1-2, edited by Avis et al; and *Pharmaceutical Dosage Forms: Disperse Systems*. Volumes 1-2, edited by Lieberman et al; published by Marcel Dekker, Inc, the disclosure of which are herein incorporated by reference in their entireties and for all purposes.

The pharmaceutical compositions are generally formulated as sterile, substantially isotonic and in full compliance with all Good Manufacturing Practice (GMP) regulations of the U.S. Food and Drug Administration.

Kits

After a pharmaceutical comprising an arylindenopyrimidine compound has been formulated in a suitable carrier, it can be placed in an appropriate container and labeled for treatment of one or more conditions that can be ameliorated by antagonizing matrix metalloproteinases. Additionally, another pharmaceutical comprising at least one other therapeutic agent useful in the treatment of such condition, or another disorder or condition associated thereof, can be placed in the container as well and labeled for treatment of the indicated disease(s). Such labeling can include, for example, instructions concerning the amount, frequency and method of administration of each pharmaceutical.

Although the foregoing invention has been described in detail by way of example for purposes of clarity of understanding, it will be apparent to the artisan that certain changes and modifications are comprehended by the disclosure and may be practiced without undue experimentation within the scope of the appended claims, which are presented by way of illustration, not limitation. The following Synthetic Schemes and Examples are set forth to aid in the understanding of the invention, and are not intended and should not be construed to limit in any way the invention set forth in the claims which follow thereafter.

General Synthetic Schemes

Representative compounds of the present invention can be synthesized in accordance with the general synthetic methods described below and illustrated in the following general schemes. The products of some schemes can be used as intermediates to produce more than one of the instant compounds. The choice of intermediates to be used to produce subsequent compounds of the present invention can be a matter of discretion that is well within the capabilities of those skilled in the art.

In particular, the compounds of the invention can be prepared according to the following synthetic Schemes 1-21, which are merely representative procedures and are not intended to limit the scope of the invention as defined in the claims that follow.

Bases used in the reaction schemes act as deprotonating agents, acid scavengers, salt forming reagents, solvents and the like. Such bases include, for example, metal hydroxides, metal carbonates, metal bicarbonates, primary, secondary or tertiaryl organic amines, heterocyclic amines or heteroaryl amines. Metal hydrides, amides or alcoholates and the like can also be suitable reagents.

The reagents for oxidation of vinyl, nitrogen or sulfur to epoxide, N-oxide derivatives or sulfoxides or sulfones can include, in a non-limiting example, meta-chloroperbenzoic acid, peroxymonosulfate (OXONE®), hydrogen peroxide (or urea complex), peracetic acid, ter-butyl peroxide, dioxirane, sodium hydpochlorite, sodium meta-periodate acid. The choice of oxidation state of the sulfur is made by one skilled in the art, but the sulfone can be preferred.

The preparation or hydrolysis of esters, amides, amide derivatives, hydroxamates and the like are synthetic methods very well known in the art.

Reductive alkylation of amines is a well known process in the art with using aldehydes or ketones and hydride transfer reagents such as sodium cyanoborohydride, sodium borohydride, di-isobutylaluminum hydride, aluminum hydride, lithium aluminumhydride and the like.

Organometallics chemistry is a useful method for preparing the compounds of the invention. Such methodologies can include, in a non-limiting example, palladium- or nickel-catalyzed carbon-carbon bond formation, carbon-nitrogen bond formation, carbon-hydrogen bond insertion and carbonylation, copper-catalyzed carbon-carbon bond formation, carbon-oxygen bond formation, and ruthenium-catalyzed ring closure metathesis. Such reactions can be performed successfully by modifications to those skilled in the art, e.g., by selecting appropriate catalysts and ligands, using appropriate solvents and changing proper reaction temperature.

For all the processes described below, it will be appreciated that relevant starting materials are commercially available, documented in the literature, or may be synthesized by known methods chosen by persons skilled in the art.

As used herein, the symbols and conventions used in examples and the schemes are consistent with those used in the contemporary scientific literature. Specifically, the following abbreviations used herein have the following meanings, respectively:

| The following abbreviations and formulas have the indicated meanings: | |
|---|---|
| Ac | acetyl |
| $Ac_2O$ | acetic anhydride |
| aq. | aqueous |
| Boc | tert-butoxy carbonyl or t-butoxy carbonyl |
| Cbz | benzyloxycarbonyl |
| $CDCl_3$ | deuterium chloroform |
| $CH_2Cl_2$ or DCM | methylene chloride or dichloromethane |
| $CHCl_3$ | chloroform |
| $CH_3CN$ or MeCN | acetonitrile |
| COPD | chronic obstructive pulmonary disease |
| Cpd or cmpd | compound |
| DABCO | 1,4-diazabicyclo[2.2.2]octane |
| DBU | 1,8-diazabicyclo[5.4.0]undec-7-ene |
| DEAD | diethyl azodicarboxylate |
| DIAD | diisopropyl azodicarboxylate |
| DIBAL | diisobutyl aluminum hydride |
| DIPEA | diisopropylethylamine |
| DMAP | 4-dimethylaminopyridine |
| DME | dimethoxyethane |
| DMF | N,N-dimethyl formamide |
| DMSO | dimethylsulfoxide |
| EDCl or EDC | 1-(3-dimethylaminopropyl)-3-ethylcarbodiimide hydrochloride |
| Et | ethyl |
| $Et_2O$ | Ethyl ether |
| EtOAc or $CH_3CO_2Et$ | Ethyl acetate |
| EtOH | ethynol |
| FLIPR | fluorometric imaging plate reader |
| Fmoc | 9-fluorenylmethoxycarbonyl |
| HOBT | 1-hydroxybenzotriazole |
| HPLC | high pressure liquid chromatography |
| LAH or $LiAlH_4$ | lithium aluminum hydride |
| LC-MS | liquid chromatography-mass spectrum |
| LHMDS | lithium bis(trimethylsilyl)amide |
| LiOH | lithium hydroxide |
| mCPBA | meta-chloroperbenzoic acid |
| Me | methyl |
| MeOH/$CH_3OH$ | methanol |
| MsCl | methanesulfonyl chloride |
| MTBE | methyl tert-butyl ether |
| min(s)/h(s), hr(s)/d(s) | minute(s)/hour(s)/day(s) |
| MS | mass spectrum, refers to data shown as m/z $(M + H)^+$ |
| $NH_4Cl$ | ammonium chloride |
| $N(i-Pr)_2Et$ | dissopropylethylamine |
| NaH | sodium hydride |
| $NaHCO_3$ | sodium bicarbonate |
| $NaN_3$ | sodium azide |
| NaOH | sodium hydroxide |

| The following abbreviations and formulas have the indicated meanings: | |
|---|---|
| $Na_2SO_4$ | sodium sulfate |
| NMP | 1-methyl-2-pyrrolidinone |
| NMR | nuclear magnetic resolution |
| psi | pounds per square inch |
| PTLC | preparative thin layer chromatography |
| RCM | Ring Closure Metathesis |
| RT/rt/r.t. | room temperature |
| s | solid |
| $SOCl_2$ | thionyl chloride |
| TEA or $Et_3N$ | triethylamine |
| TFA | trifluoroacetic acid |
| TFAA | trifluoroacetic anhydride |
| THF | tetrahydrofuran |
| TLC | thin layer chromatography |
| TMSCl | chlorotrimethylsilane or trimethylsilyl chloride |

As used in Schemes 1-21, $R_{14}$ and $R_{16}$ independently are optionally substituted alkyl or optionally substituted aryl.

As used in Schemes 1-21, T, $T_1$, $T_2$, $T_3$ reagents are independently an electrophile or a group convertible into an electrophile. Such groups include halides, sulfonate ester, epoxides, thioepoxides, hydroxyl groups and the like.

As used in Schemes 1-21, L represents a leaving group such as halogen or sulfonate esters (e.g. tosylate or mesylate).

As used in Schemes 1-21, P, $P_1$, $P_2$ and $P_3$ stand for protecting groups. Protecting groups are manipulated according to standard methods of organic synthesis (T. W. Greene and P. G. M. Wuts (1999) *Protective Groups in Organic Synthesis*, John wiley & Sons). Cleavage of protecting groups such as carbamates, benzyl or substituted benzyl groups, silyl groups, triphenylmethyl (trityl) can be carried out at different steps in the synthesis of the compounds of this invention as required by methods selected by one skilled in the art.

Scheme 1, wherein $R_{2a}$ and $R_{2b}$ are independent members of $R_2$, and m, W, ring b, $R_1$, $R_2$, $R_5$, $R_6$, $R_7$, $R_8$, $R_9$, P, $P_1$ T, $T_1$, $T_2$, and $T_3$ are as described above, illustrates the general methods for synthesis of a series of compounds of the invention. The representative ring a is selected from a group of 6- to 9-membered heteroaryl or heterocyclic structures listed in Scheme 1. The unmasked nitrogen in ring a of 1a can be functionalized to various alkylated amines, amides, sulfonamides, sulfonyl ureas, phosphonamides following procedures well known in the literature in two different orders to give compound 1d. Scheme 1 only shows several non-limiting procedures to execute such nitrogen functionalizations. Deprotection of 1d can yield compound (1a). Acylating reagents for amide formation are not limited to acid halides as shown in the Scheme 1. Anhydrides, mixed anhydrides, activated carbonyl under basic conditions or carboxylic acids through peptide coupling conditions are also suitable. An alternative route to make compound 1d, which is not shown in the Scheme 1, wherein $R_6$ is optionally substituted methylene or when m is not equal to 0, is the reductive amination of 1a with aldehydes or ketones followed by functionalization of the nitrogen in ring a.

Scheme 1
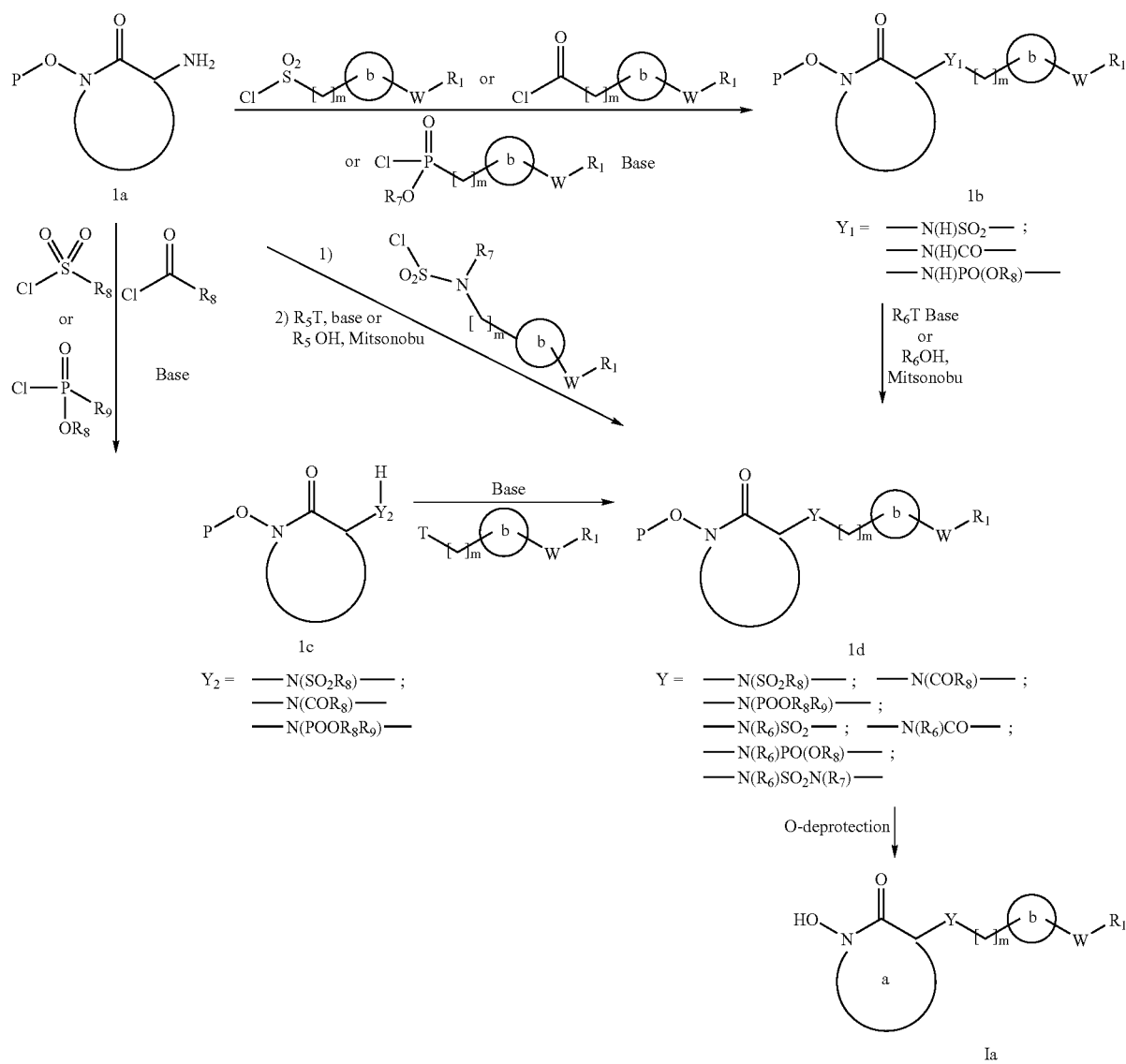
Ring a is selected from:
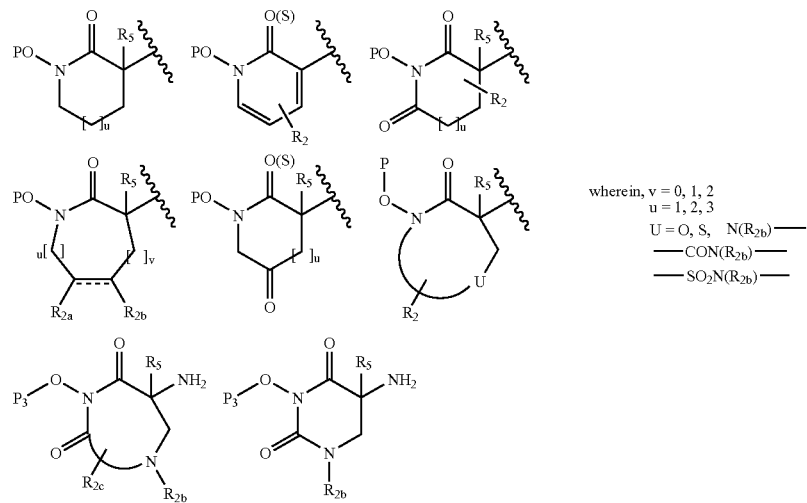
wherein, v = 0, 1, 2
u = 1, 2, 3
U = O, S, N($R_{2b}$)—
—CON($R_{2b}$)—
—$SO_2$N($R_{2b}$)—

Scheme 2, wherein $R_{2a}$ and $R_{2b}$ are independent members of $R_2$, and $R_2$, $R_5$, $R_{14}$, P, $P_1$, $P_2$, $P_3$, and T are as described above, illustrates the representative procedures for synthesis of α-amino-substituted 6- to 9-membered unsaturated N-hydroxyl lactams 2f via Ring Closure Metathesis (RCM) reaction catalyzed by ruthenium reagents such as Grubb's catalysts (relevant examples: *Tetrahedron,* 2003, 59, 4501-4513; *Tetrahedron Lett.* 2004, 45, 9607-9610; *Euro. J. Org. Chem.* 2001, 20, 3891-3897). Reduction (such as under hydrogenation conditions) of 2f can yield saturated lactams 2g. A nonlimiting example for preparation of vinyl glysine derivatives 2a is bromination of amino acetic ester followed by displacement of bromo with Grignard's reagents (*J. Chem. Soc. Perkin Trans,* 1998, 1, 2485-2499). Hydroxamate 2c can be prepared under peptide coupling conditions as shown in this scheme or via the direct conversion of ester 2a by treatment with O-protected hydroxylamine under basic conditions such as KOH, NaOMe or LiHMDS (*J. Org. Chem.* 2005, 70, 6925-6928) or using Weinreb's trimethyl aluminum conditions (*Syn. Commun.* 1982, 12, 989). Analogs of 2a, wherein $R_5$ is not a hydrogen atom, can be prepared following the literature procedures (relevant examples: *Tetrahedron,* 2003, 59, 4501-4513; *Tetrahedron,* 1988, 44, 4207-4219; *Helvetica Chimica Acta.* 1986, 696, 1365-77). Allylglycine and homoallylglycine derivatives 2b, wherein $R_5$ is a hydrogen atom, are commercially available. α-Branched 2b ($R_5$ is not hydrogen) can be prepared according to procedures in the literature (relevant examples: *Eur. J. Org. Chem.* 2003, 1244-1263; *Tetrahedron Lett.* 2003, 44, 2045-2048).

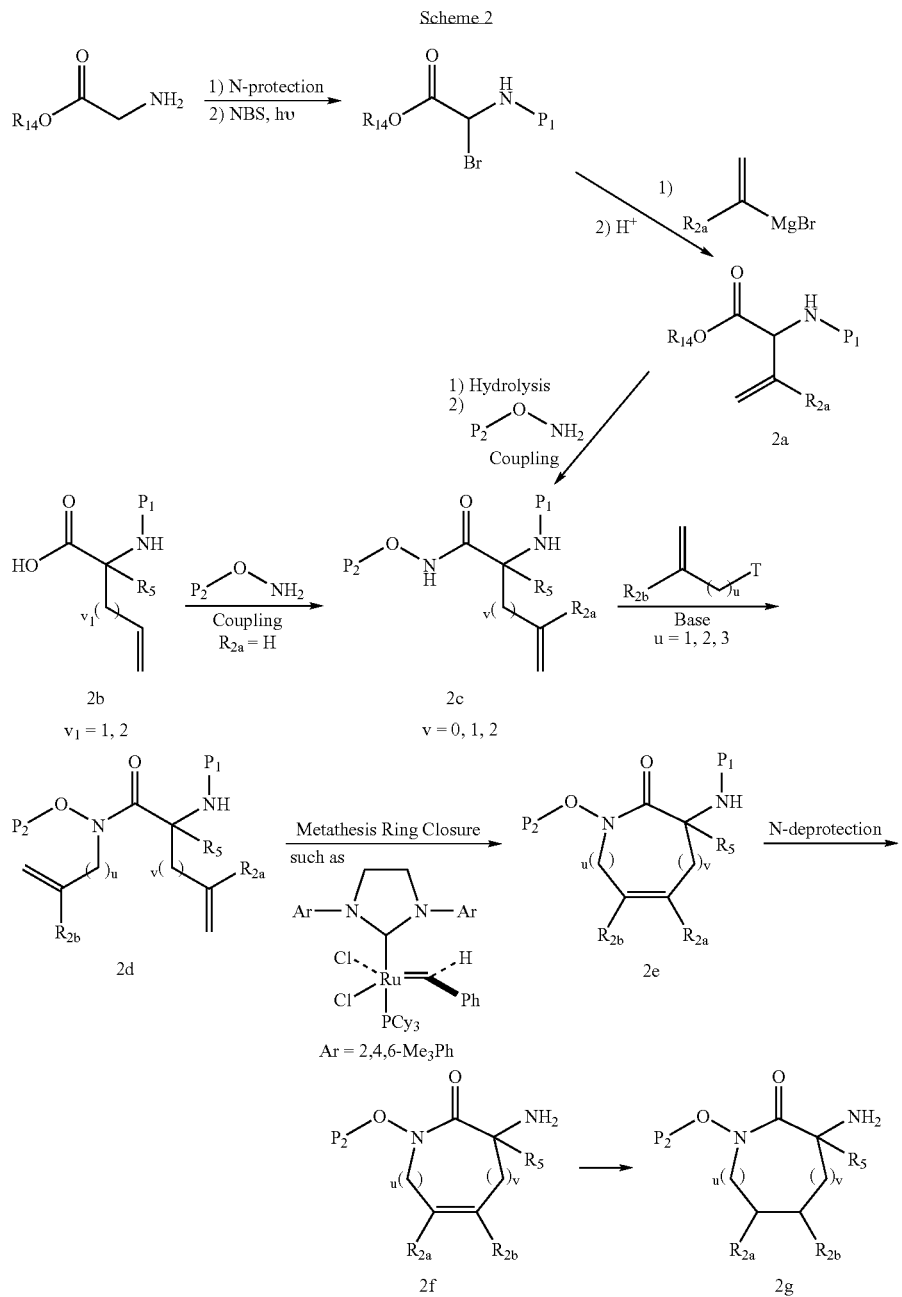

According to Scheme 3, wherein $R_5$ and P are as described above, Compound 3b can be prepared from commercially available N-protected glutamic acid or 2-aminoadipic acid 3a by one-step ring closure reaction under coupling conditions with O-protected hydroxylamine. Cleavage of Boc protecting group gives compound 3c. Quaternary glutamic acids, 2-substituted-2-aminoadipic acids, branched glutamic acid derivatives and branched 2-aminoadipic acids ($R_5$ is not hydrogen) can be synthesized by a variety of literature reported methods (several non-limiting examples: *Helvetica Chimica Acta.* 1985, 68, 1507-18; *ARKIVOC* [www.arkat-usa.org], 2000, 1(5), 820-831; *Tetrahedron Lett.* 2003, 44, 1235-1238; *Heterocycles,* 1990, 31, 191-5; *Tetrahedron Lett.,* 1995, 36, 3247-50; *Tetrahedron,* 1996, 52, 8365-8386; *Bull. Korean Chem. Soc.* 1999, 20, 106-108). Such 3a analogs can be converted into analogs of 3c which are substituted with $R_2$ on the ring and with $R_5$ at α-carbon position in a similar manner outlined in Scheme 3 or by routine modification of reaction conditions.

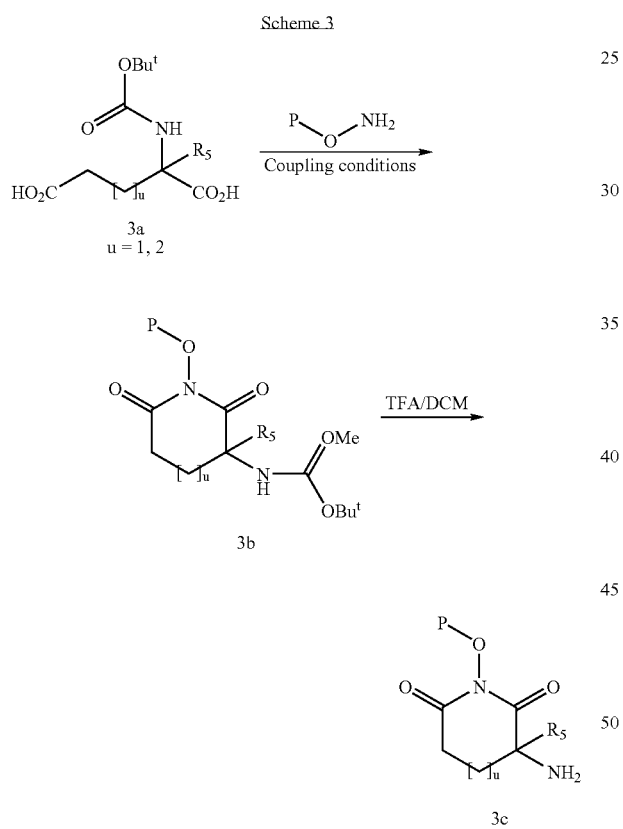

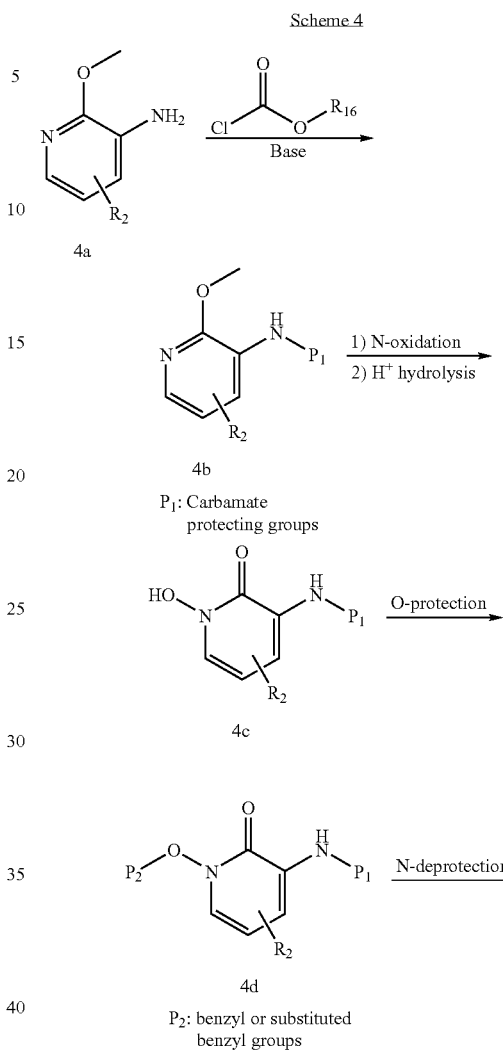

The preparation of 3-amino-N-hydroxy-2-pyridone derivatives is outlined in Scheme 4, wherein $R_2$ and $R_{16}$ are as described above. The amino may be protected by a carbamate group ($P_1$) such as Fmoc, and the N-hydroxyl group may be protected by a benzyl group ($P_2$). Hydroxypyridone 4c is prepared via oxidation of pyridine ring 4b with an oxidant such as urea hydrogen peroxide complex (UHP) (*Tetrahedron Lett.* 2000, 41, 2299-2302) or mCPBA followed by acidic hydrolysis (e.g. 2N HCl solution in MeOH reflux). The N-deprotection to removal Fmoc under basic conditions does not affect $P_2$.

Scheme 5, wherein $P_1$, $P_2$, and $P_3$ are as described above, illustrates a preparation process of 6- to 7-membered O-protected N-hydroxyl oxo-lactams. Epoxidation of the alkene of amino acid derivatives 2a (from Scheme 2) followed by treatment with LiBr affords a mixture of isomers bromohydrins 5b (*Tetrahedron: Asymmetry.* 1996, 7, 2585-2593). Oxidation of the hydroxyl group with an oxidant such as pyridinium chlorochromate gives α-bromoketone 5c (*Tetrahedron: Asymmetry,* 2002, 13, 1901-1910). Upon removal of $P_2$ by ester hydrolysis or acid treatment such as TFA (when $P_2$ is t-butyl), the resulting carboxylic acid intermediates can be converted into hydroxamates and subsequently treated with mild base to afford 5d.

Scheme 5

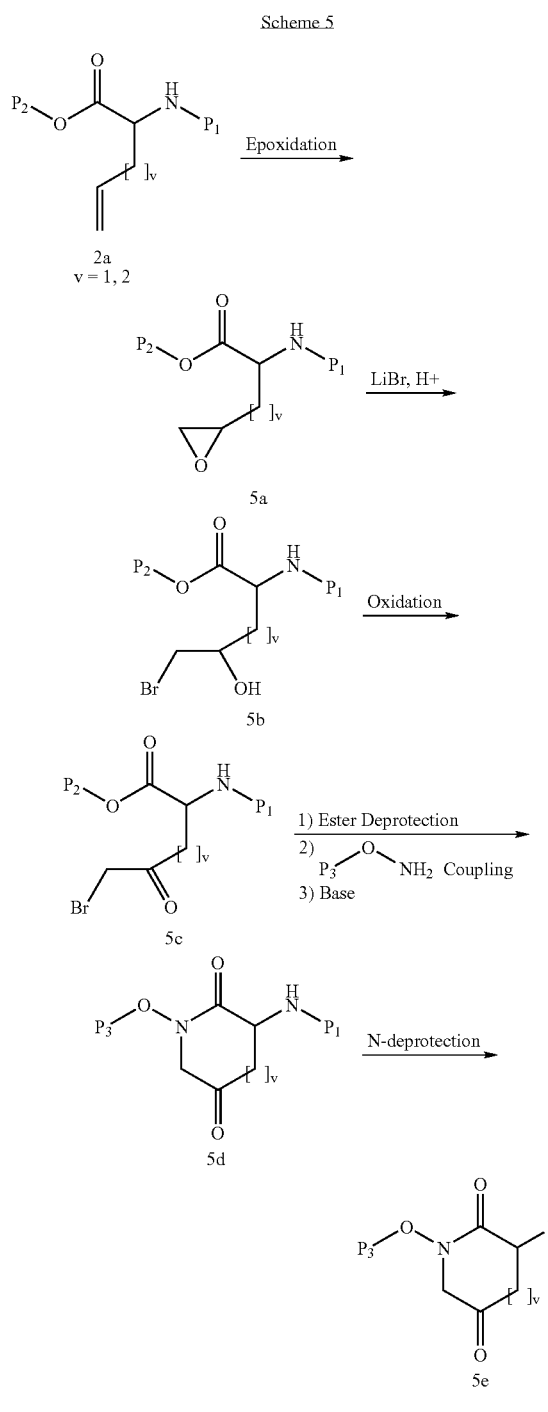

Scheme 6

The cyclization of 6f may also be achieved by conversion of the hydroxyl group of 6f to a leaving group L such as tosyl followed by base treatment. Reagents 6c are commercially available alcohols or may be prepared by protection of the hydroxyl group followed by reactions of the carboxylic acids or acid derivatives and amines by procedures well known in the literature.

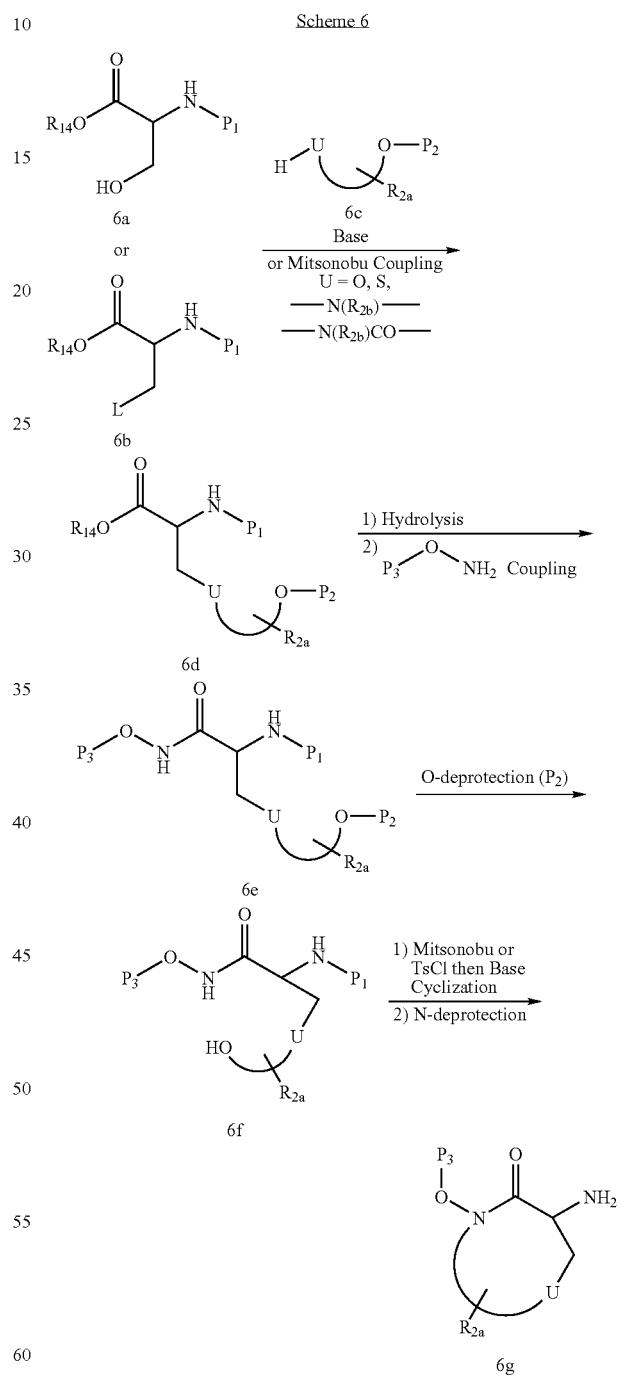

Scheme 6, wherein $R_{2a}$ and $R_{2b}$ are independent members of $R_2$, and $R_2$, $R_{14}$, $P_1$, $P_2$, and $P_3$ are as described above, illustrates a representative process for the preparation of 6- to 9-membered heteroatom-containing O-protected N-hydroxyl ring a of 6g. Mitsonobu reactions of serine derivatives 6a with 6c afford compounds 6d. An alternative method to obtain 6d is the conversion of the hydroxyl group of 6a to a leaving group L which is subsequently attacked by an anion of 6c. The selective deprotection of alcohols 6e (removal of $P_2$) afford hydroxamates 6f. Mitsonobu coupling reactions of 6f followed by N-deprotection give the cyclized compounds 6g.

An alternative synthesis of a series of compounds 6f is outlined in Scheme 7, wherein $R_{2a}$ and $R_{2c}$ are independent members of $R_2$, and $R_2$, $R_5$, $R_{14}$, L, $P_1$, $P_2$, and $P_3$ are as described above. Conversion of β-amino acids 7a with two differentiated protecting groups ($P_1$ and $P_2$) to the hydroxamate under peptide coupling conditions, subsequent β-amino deprotection and reductive amination with R$_{2a}$CHO afford 7b. Acylation or sulfonylation of 7b with acid chlorides or sulfonyl chlorides 7c under basic conditions give 7d. α-Amino deprotection of 7d can yield compounds 6f. Alternatively, treatment of 7b with reagent ClCOO(p-NO$_2$Ph) followed by N-deprotection results in 7e (relevant example: *Tetrahedron Lett.* 1996, 37, 5277-5280). β-Amino group of 7b may also displace L of reagent 7f and the resulting ester can be hydrolyzed to give 7g. The cyclic compounds 7h can be prepared by subjection of 7g to peptide coupling conditions or by treatment of 7g with SOCl$_2$ and base to convert the carboxylic acids to the acid chlorides and subsequent cyclization. Diamino propionic acids 7a wherein R$_5$ is not hydrogen may be prepared by literature known methods (relevant examples: *Helvetica Chimica Acta* 2004, 87, 1016-1024; *Tetrahedron Lett.* 1991, 32, 2277-2280).

Alternative syntheses of the compounds of formulae (Ib) and (Ic) wherein ring a is N-hydroxy-2-pyridone derivatives are outlined in schemes 8, 9 and 10, of which synthetic procedures have been discussed elsewhere.

Scheme 8

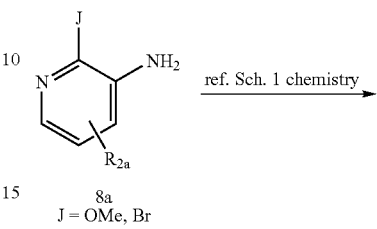

8a
J = OMe, Br

Scheme 7

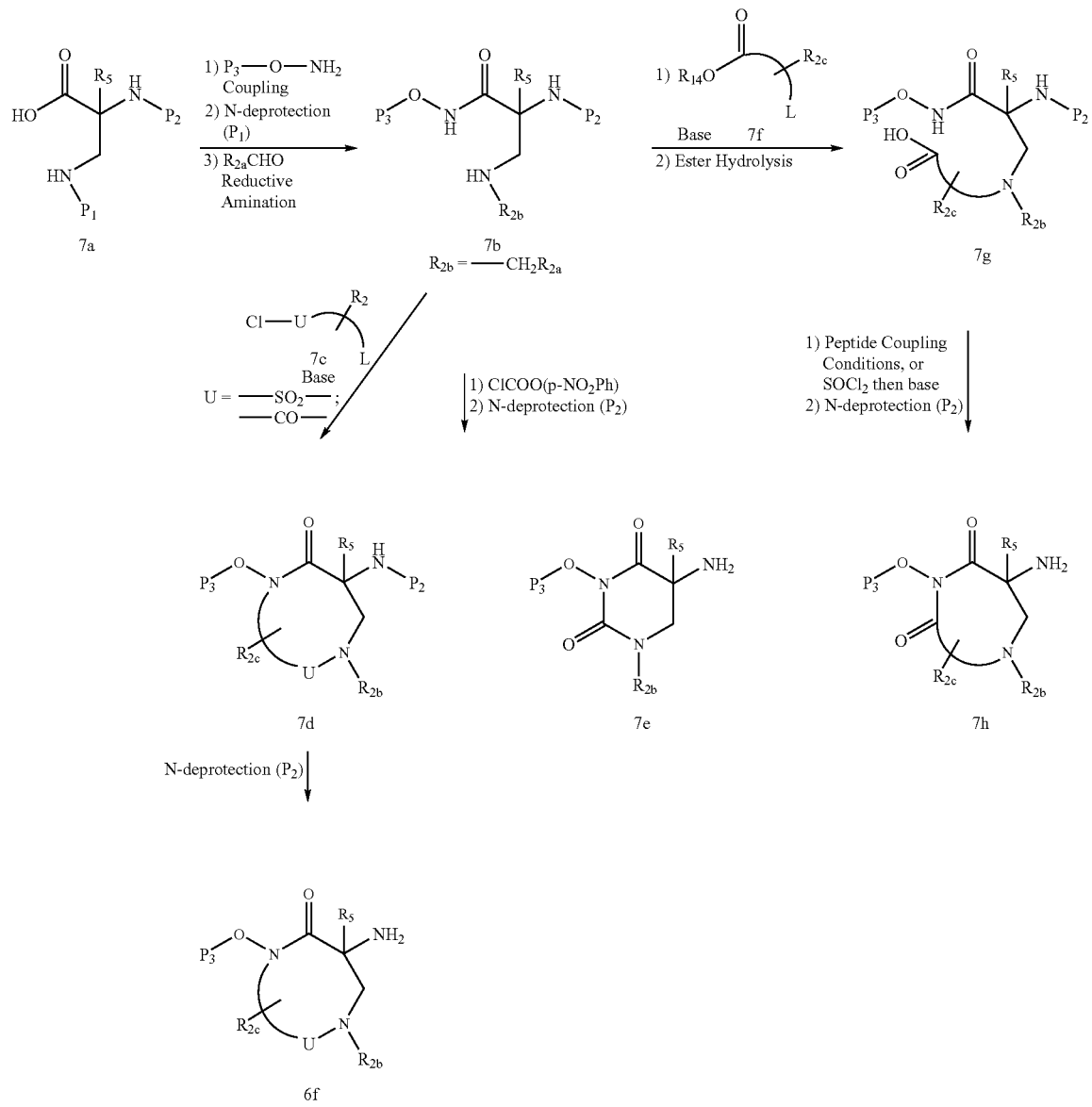

-continued
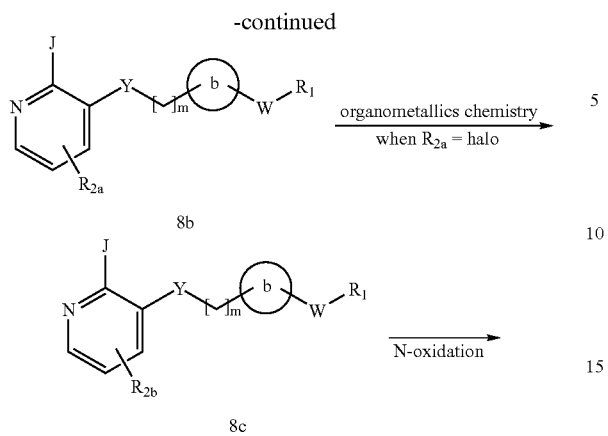
8b
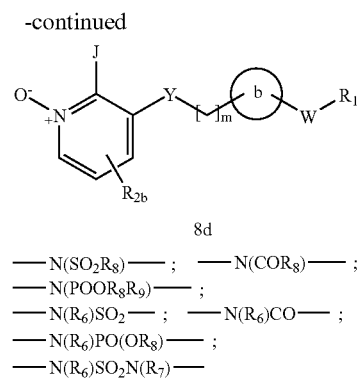
8d
Y = —N(SO$_2$R$_8$)—  ;  —N(COR$_8$)—  ;
—N(POOR$_8$R$_9$)—  ;
—N(R$_6$)SO$_2$—  ;  —N(R$_6$)CO—  ;
—N(R$_6$)PO(OR$_8$)—  ;
—N(R$_6$)SO$_2$N(R$_7$)—
8c
Scheme 9
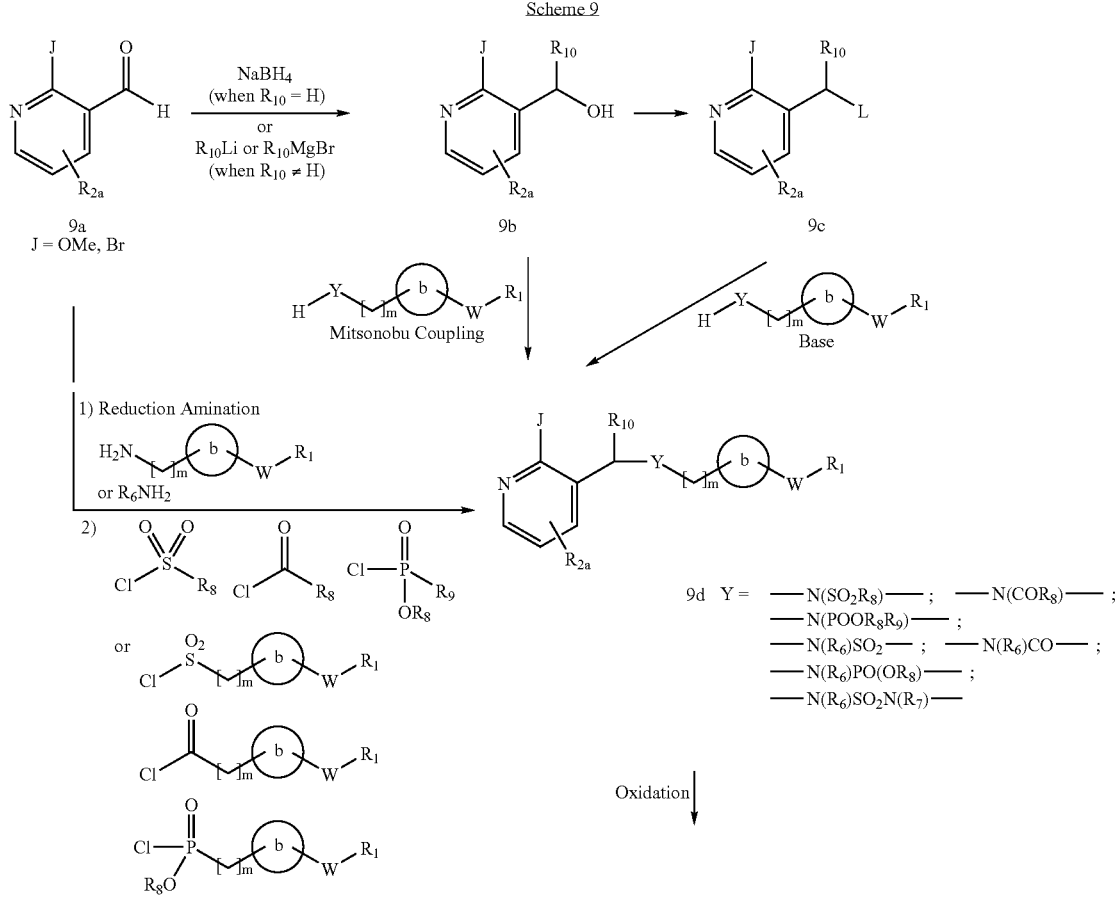
9d  Y = —N(SO$_2$R$_8$)—  ;  —N(COR$_8$)—  ;
—N(POOR$_8$R$_9$)—  ;
—N(R$_6$)SO$_2$—  ;  —N(R$_6$)CO—  ;
—N(R$_6$)PO(OR$_8$)—  ;
—N(R$_6$)SO$_2$N(R$_7$)—
9e Scheme 10

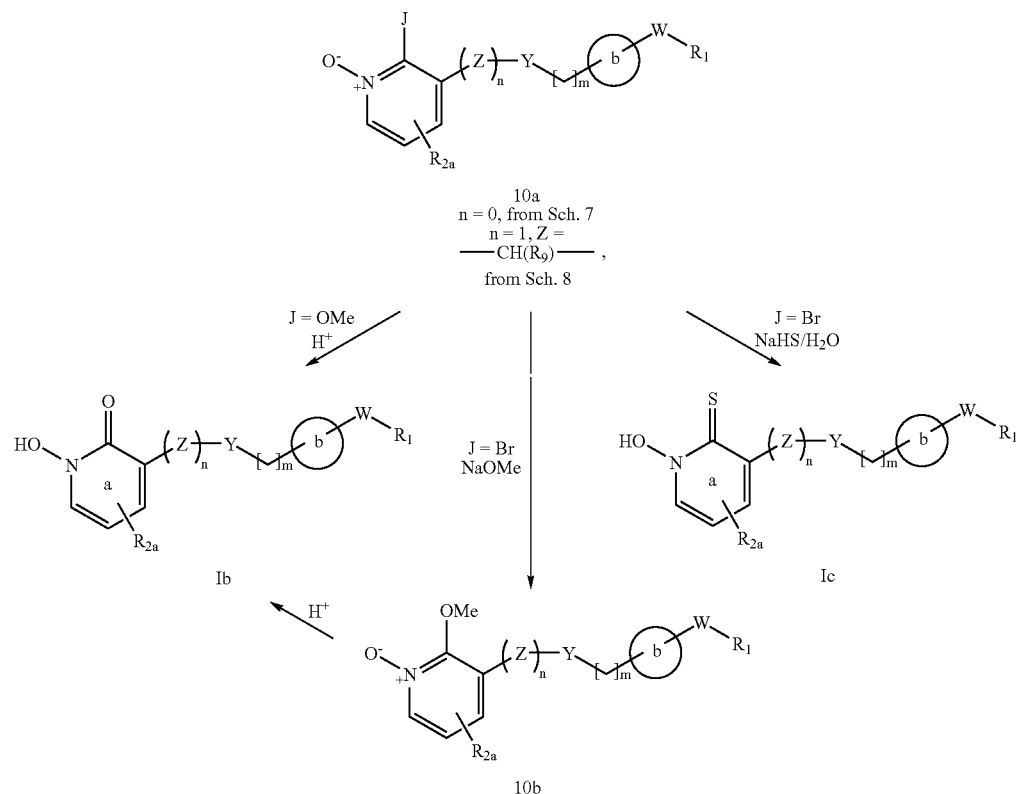

Scheme 11, wherein m, W, ring b, $R_1$, $R_2$, $R_5$, $R_{14}$, P, $P_1$, T, $T_1$, $T_2$, and $T_3$ are as described above, illustrates a representative synthesis of a series of compounds of formula (Id) wherein ring a in formula (I) is a 6- to 9-membered lactam which may contain one or two hetero atoms on the ring, and Y is sulfonyl. Displacement of the leaving group T of 11a with a thiol under basic conditions affords 11b. Alkylation of 11c with 11d containing two electrophile moieties ($T_1$, $T_2$) can yield 11e. Oxidation of the sulfur of 11e to sulfone provides an acidic α-carbon. A basic intramolecular cyclization of the sulfone intermediate give 11f, which can be further functionalized with $R_5$ halides at α-carbon position by treatment with base. Reagents 11d may contain heteroatoms on the linker or are substituted with $R_2$ and are commercially available, or otherwise, can be prepared by the well known methods.

Scheme 11

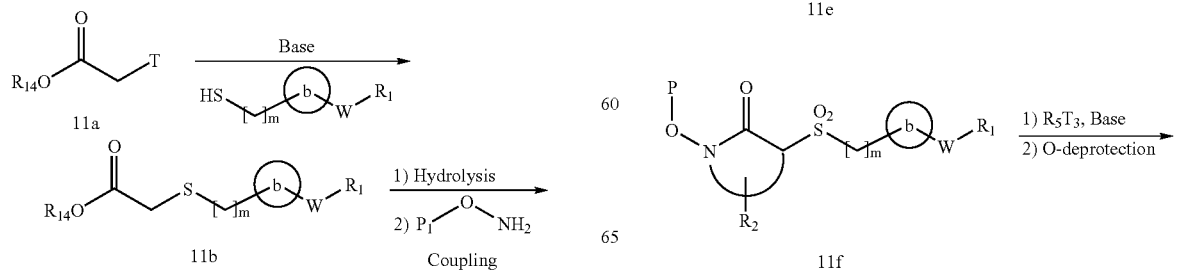

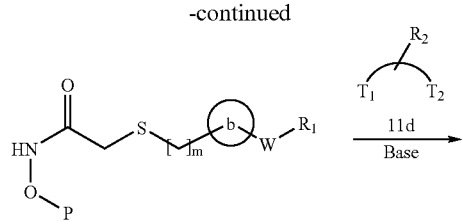

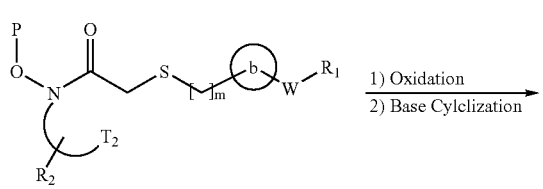

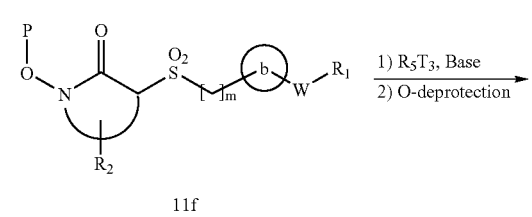

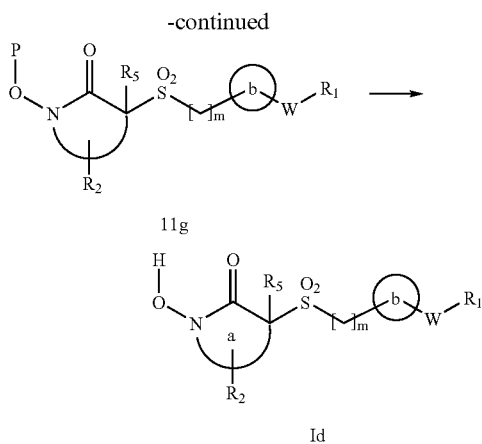

Scheme 12, wherein $R_{2a}$ and $R_{2b}$ are independent members of $R_2$, and m, W, ring b, $R_1$, $R_2$, $R_5$, $R_{14}$, P, $P_1$, T, $T_1$, $T_2$, and $T_3$ are as described above, illustrates a preparation example of a series of compounds of formulae (Ie1) and (Ie2) wherein ring a in formula (I) is an unsaturated or saturated 6- to 9-lactams. The alkene-lactam ZBG formation via RCM methods shown in the Scheme 2 and 12, which are merely representative examples, can be applied to other chemical series with various scaffolds Y. The choice of the metathesis ring closure may be made before or after the introduction of

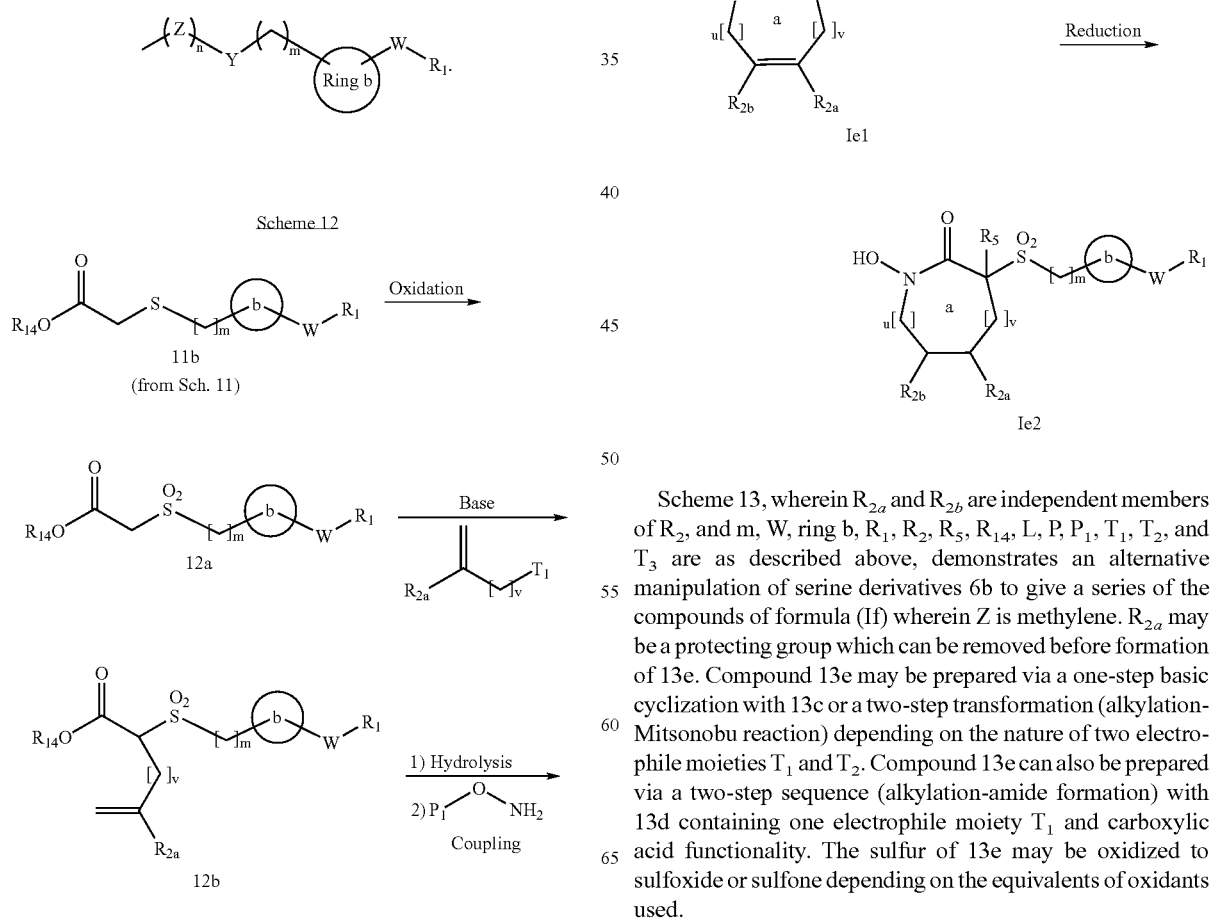

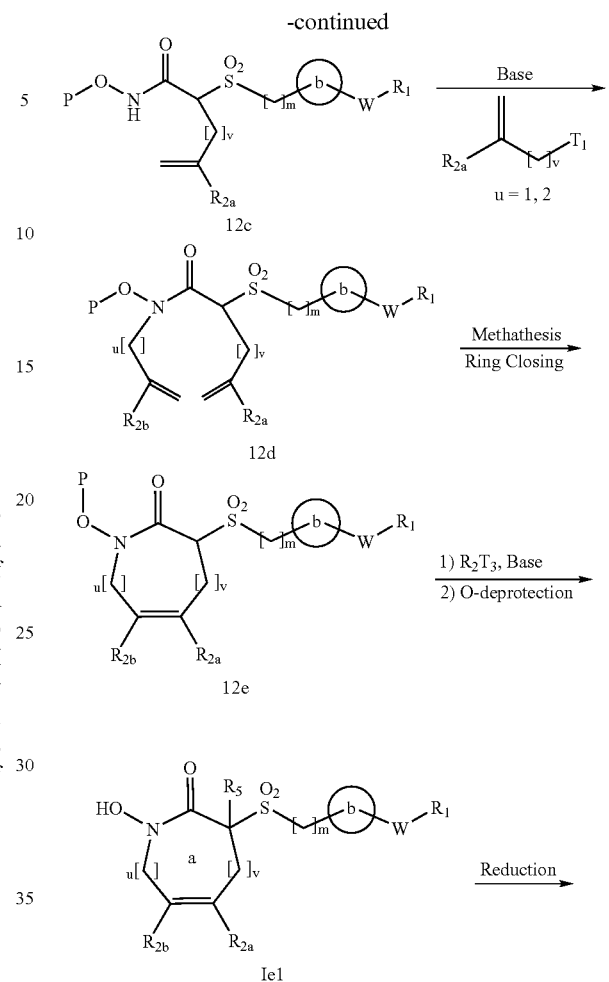

Scheme 13, wherein $R_{2a}$ and $R_{2b}$ are independent members of $R_2$, and m, W, ring b, $R_1$, $R_2$, $R_5$, $R_{14}$, L, P, $P_1$, $T_1$, $T_2$, and $T_3$ are as described above, demonstrates an alternative manipulation of serine derivatives 6b to give a series of the compounds of formula (If) wherein Z is methylene. $R_{2a}$ may be a protecting group which can be removed before formation of 13e. Compound 13e may be prepared via a one-step basic cyclization with 13c or a two-step transformation (alkylation-Mitsonobu reaction) depending on the nature of two electrophile moieties $T_1$ and $T_2$. Compound 13e can also be prepared via a two-step sequence (alkylation-amide formation) with 13d containing one electrophile moiety $T_1$ and carboxylic acid functionality. The sulfur of 13e may be oxidized to sulfoxide or sulfone depending on the equivalents of oxidants used.

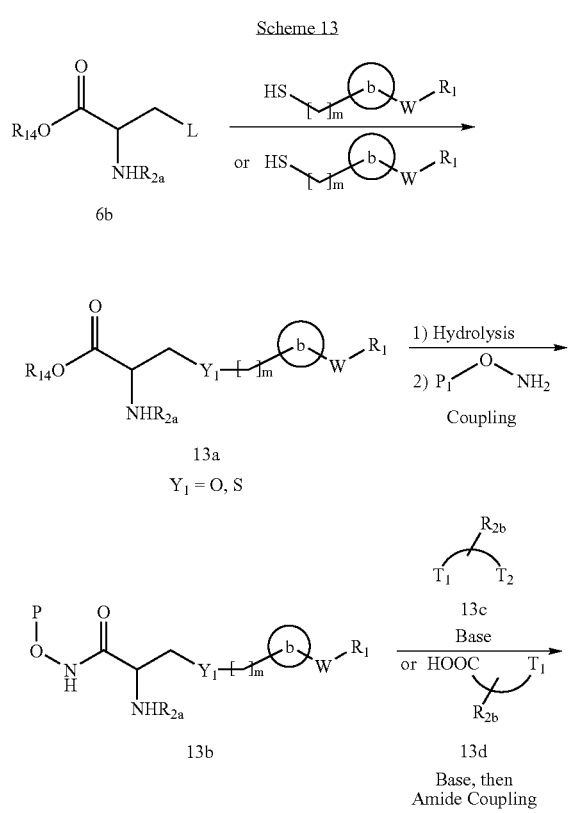
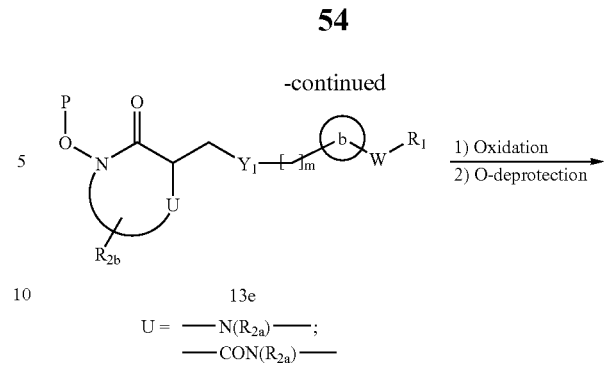

An extension of Scheme 13, Scheme 14 demonstrates the preparation of the compounds with a broader scope of Y, wherein $R_{2a}$ and $R_{2b}$ are independent members of $R_2$, and m, W, ring b, $R_1$, $R_2$, $R_6$, $R_7$, $R_8$, $R_9$, $R_{14}$, P, and T are as described above. Compound 14c, prepared from epoxide 14a via a ring opening process by a nucleophile 14b, may be manipulated in two different ways shown in the Scheme 14. The cyclized compound 14f is prepared either by Mitsonobu reaction of 14e or basic intramolecular cyclization of 14j.

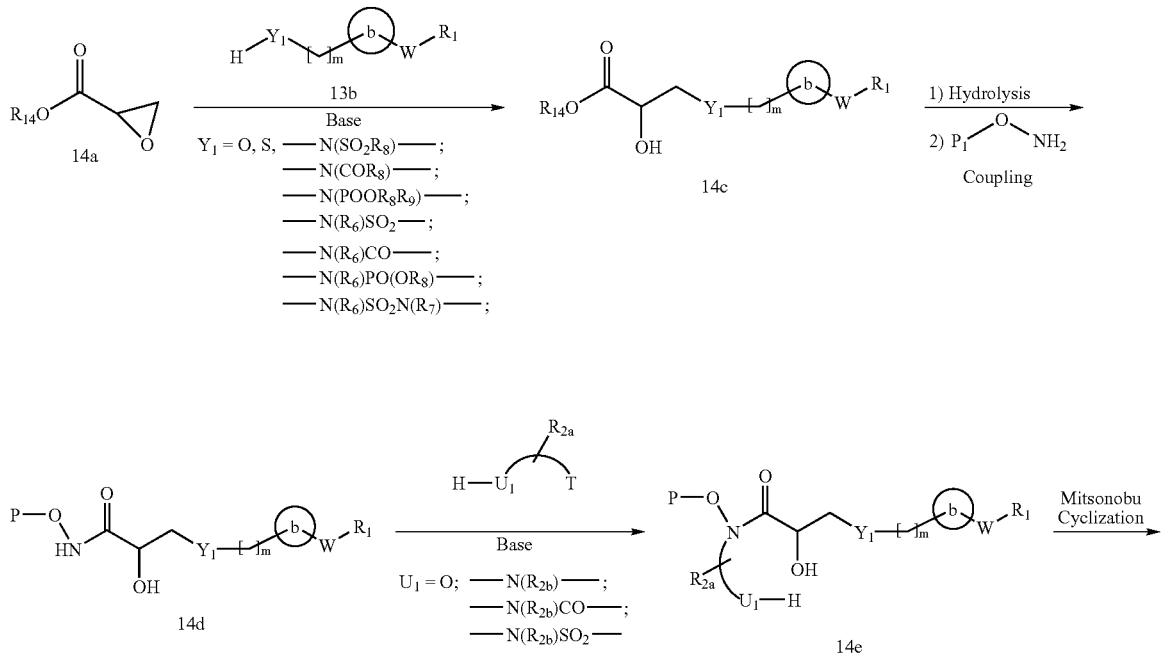

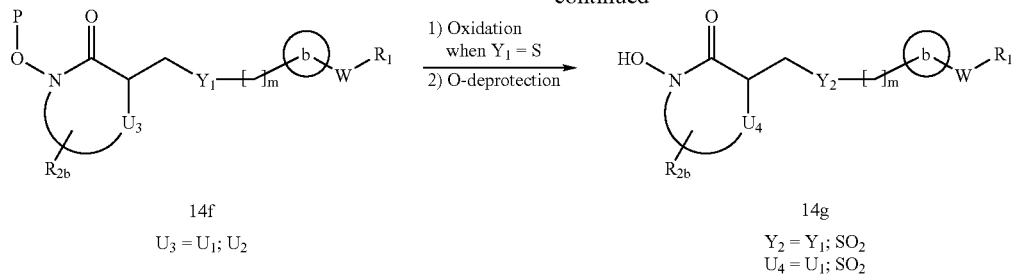

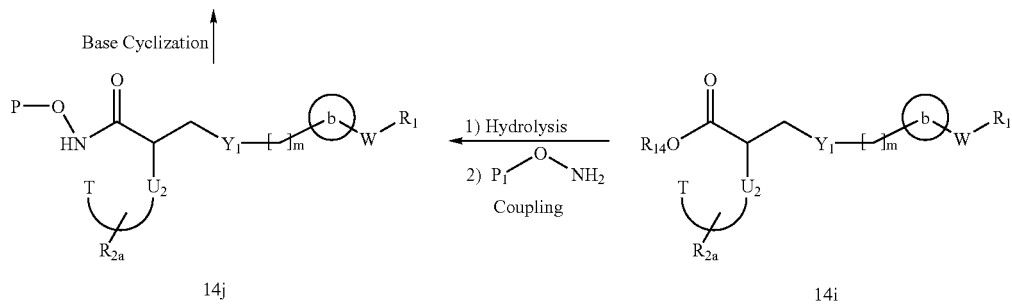

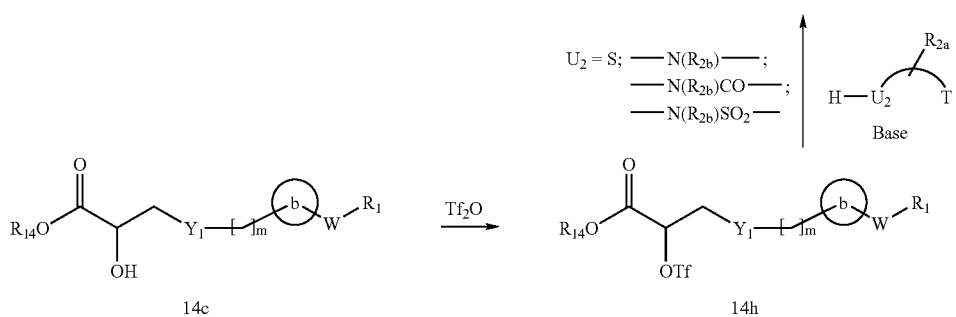

Also an extension of Scheme 13, Scheme 15 illustrates the preparation of the compounds (Ig) wherein $R_5$ is not hydrogen, wherein $R_2$ and $R_{2b}$ are independent members of $R_2$, and m, W, ring b, $R_1$, $R_2$, $R_5$, T, $P_1$, and $P_2$ are as described above. Displacement of leaving group T of 15a followed by Strecker synthesis afforded nitrile 15c, which is hydrolyzed to carboxylic acid (*Bioorg. Med. Chem. Lett.* 2001, 11, 2723-2725). N-protection, oxidation of the sulfur of 15d and N-deprotection give α-amino carboxylic acid 15e. $R_{2a}$ functionalization of the amino group is accomplished by alkylation, acylation or reductive amination.

Scheme 15

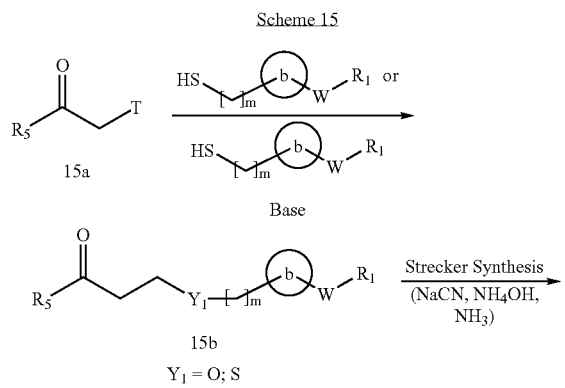

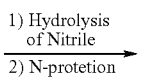

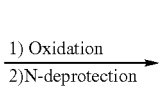

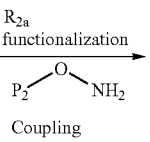

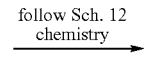

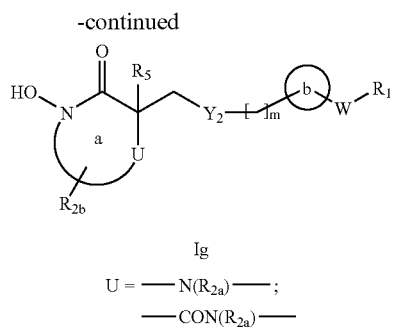

Ig

U = —N(R$_{2a}$)—;
—CON(R$_{2a}$)—

Scheme 16, wherein R$_{2a}$ and R$_{2b}$ are independent members of R$_2$, and m, W, ring b, R$_1$, R$_2$, R$_6$, R$_7$, R$_8$, R$_{14}$, P, and T are as described above, illustrates the preparation of a series of the compounds of formula (Ih) wherein R$_5$ in formula (I) is hydroxy group. Epoxidation of α,β-unsaturated ester 16b followed by anion attack (16d) affords a tertiary alcohol 16e. Similar transformations as discussed in elsewhere yields the compounds of formula (Ih).

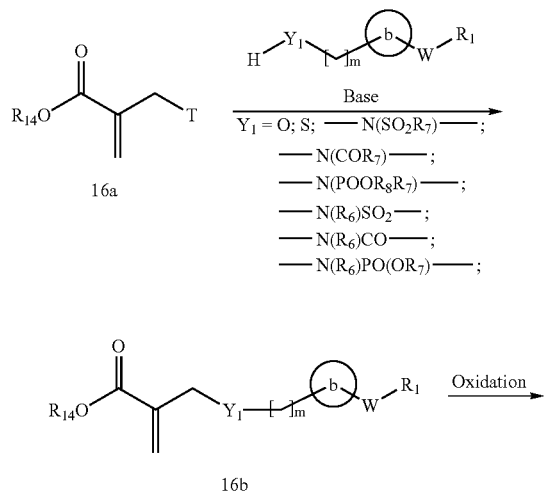

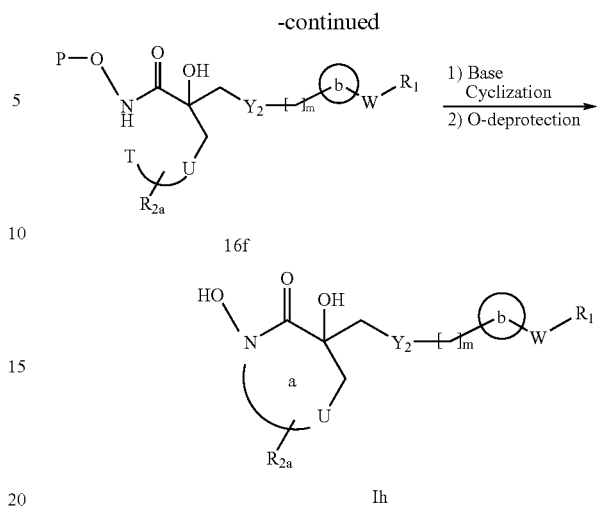

16f

Ih

Scheme 17, wherein m, W, ring b, R$_1$, R$_6$, R$_8$, R$_9$, and P are as described above, illustrates a representative example for preparation of a series of the compounds of formula (Ii) wherein ring a in formula (I) is a 6-membered N-hydroxyl lactam and R$_5$ in formula (I) is a hydroxy group. Hydroxamate 17b is prepared from lactone 17a (preparation of 17a: *Tetrahedron*, 1988, 44, 4207-4219; an alternative preparation method: *J. Chem. Soc. Chem. Commun.* 1984, 2, 132-133) by the hydroxylaminolysis process, preferably with aluminate formed from the O-benzyl hydroxylamine and AlMe$_3$, or preferably by treatment with LiHMDS. Activation of the hydroxyl as a leaving group followed by treatment with base or subjection of the alcohol 17b to the Mitsonobu conditions affords lactam 17c. Epoxidation and subsequent ring opening give 17e. Analogs of 17a which are substituted with R$_1$ on the lactone ring may be synthesized by literature known methods (relevant examples: Tetrahedron, 2003, 59, 9199-9211; *J. Chem. Soc. Perkin Transactions* 1: *org. & Bio-org. Chem.* (1972-1999), 1981, 11, 2848-2863). Such lactones can be converted to N-hydroxy-lactams 17e in a similar manner as outlined in Scheme 17.

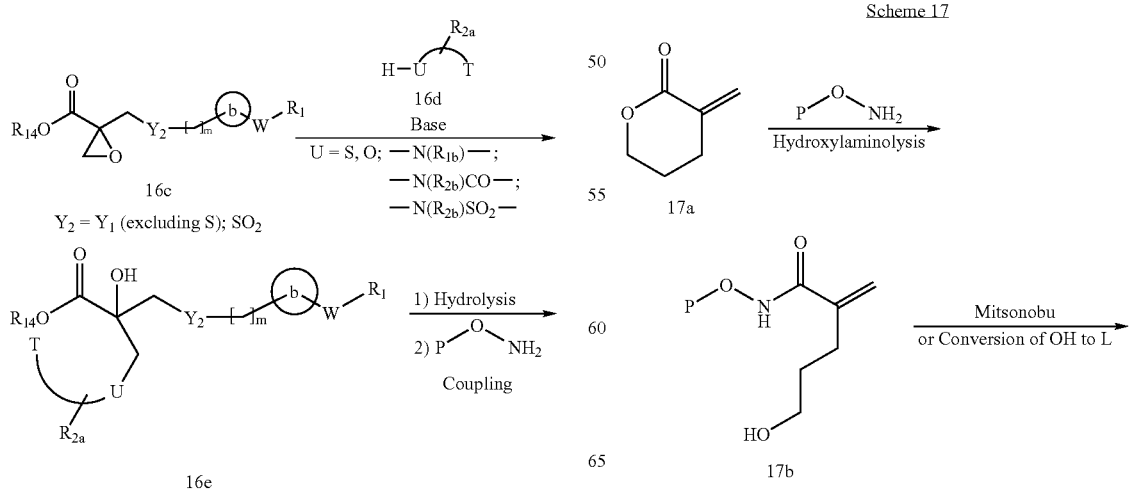

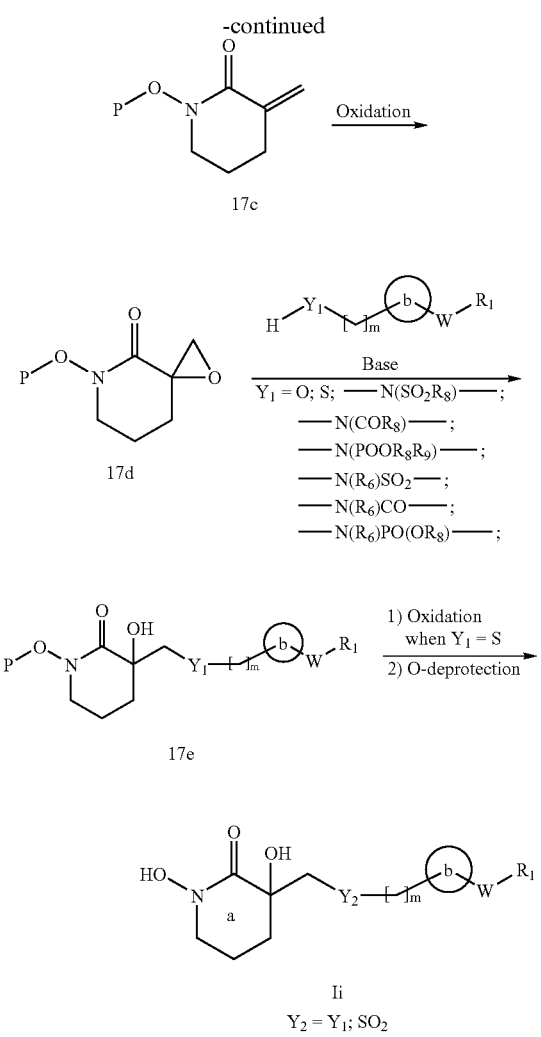

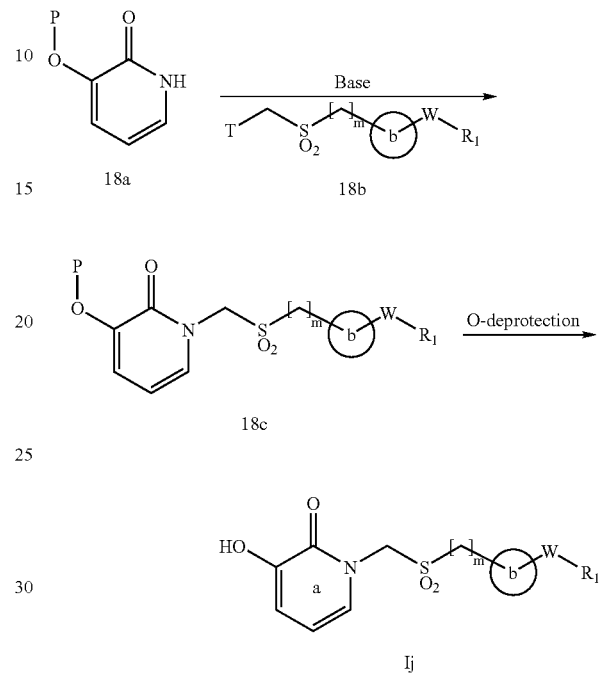

reagents 18b (a general procedure for preparing 18 b type compounds: *Syn. Comm.* 2004, 34, 2443-2449) followed by O-deprotection by acid treatment or subjection to hydrogenation conditions) affords the compounds of formula (Ij).

Scheme 18, wherein m, W, ring b, $R_1$, T, and P are as described above, illustrates a preparation process of the compounds of formula (Ij) wherein ring a in formula (I) is 3-hydroxy-2-pyridone. Alkylation of 18a (preparation of 18a: *J. Comb. Chem.* 2003, 5, 201-204) with halomethyl sulfone An extension of Scheme 18, Scheme 19 demonstrates the preparation of the compounds of formula (Im) with a broader scope of Y and wherein Z is ethylene in formula (I), wherein m, W, ring b, $R_1$, $R_6$, $R_8$, $R_{14}$, L, T, and P are as described above. Hydroxypyridone 19b is protected (19b prepared according to literature procedure: *J. Med. Chem.,* 1990, 33, 1749-1755) as a benzyloxy group preferably and treated with a reducing agent such as lithium aluminum hydride to afford alcohol 19c. Manipulation of 19c in two non-limiting manners as shown in Scheme 19 followed by O-deprotection yields the compounds of formulae (Im1) and (Im2).

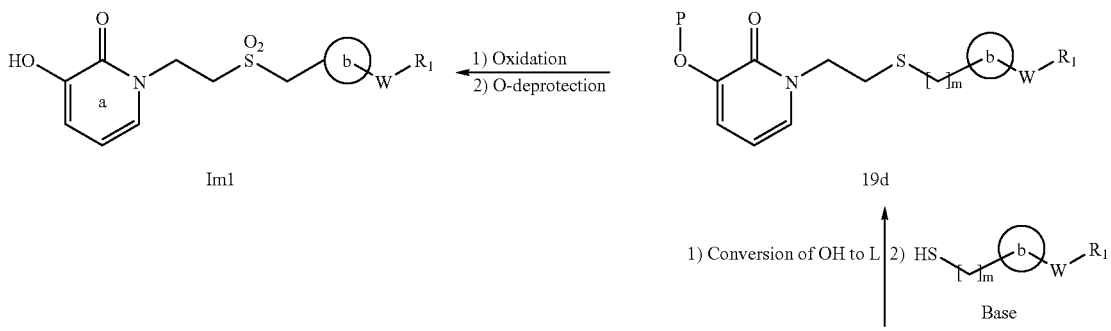

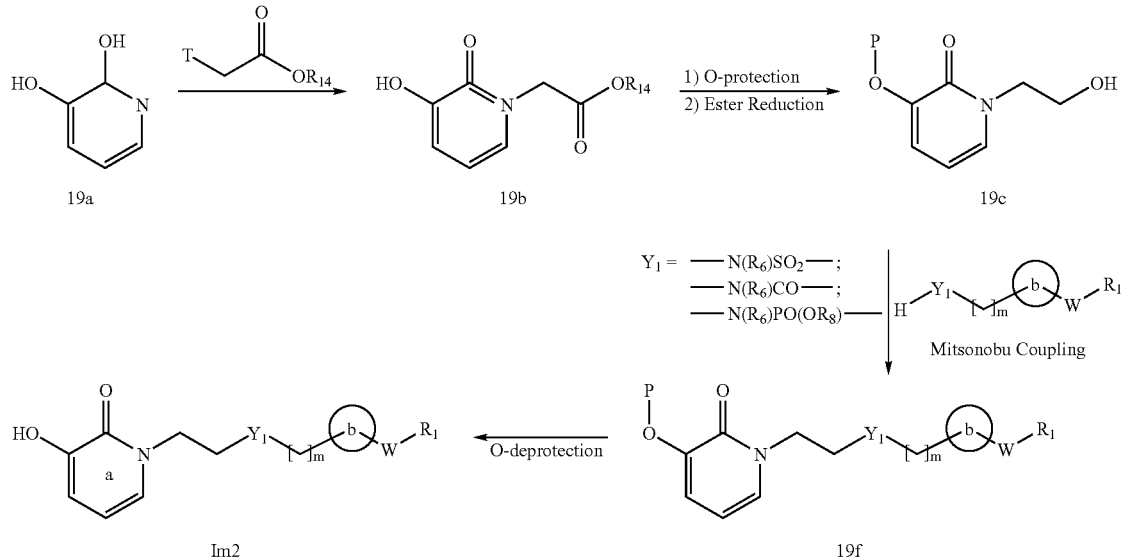

Scheme 20, wherein $R_2'$ and $R_2''$ are independent members of $R_2$ and $R_2$ are as described hereinabove, and Y, m, W, ring b, and $R_1$ are as described in Scheme 19 above, shows a representative and non-limiting example for further manipulation of the compounds of formula (Ik1) (prepared according to schemes 18 and 19). Compounds of formula (Ik2) with amino methyl substitution on the pyridone ring is prepared by the Mannich reaction from Ik1 and a Mannich base formed from amines and aldehydes (*Syn. Comm.* 1998, 28, 1563-1574).

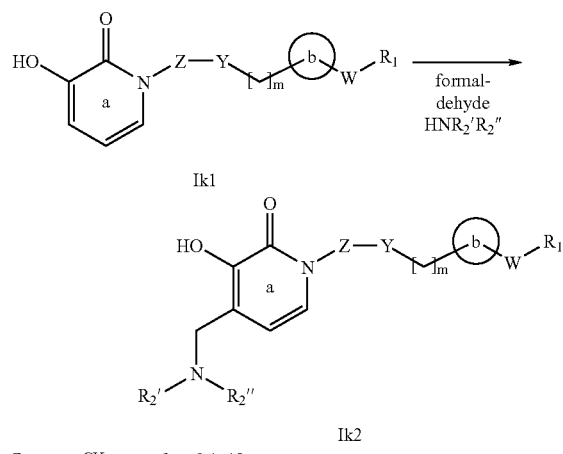

Scheme 21, wherein Z, m, and ring b are as described hereinabove, illustrates representative procedures for the introduction of —W—$R_1$ species to ring b in formula (I). Organometallics chemistry conducted to prepare the compounds of the invention are not limited to the methods shown in Scheme 21. Alternative methods, in a few non-limiting procedures, such as conversion of halogen T of 21a to boronic acids, boronic esters or tin reagents and the like and subsequent coupling with halides or sulfonate ester, may be also suitable. The selection of process as well as reaction conditions shall be consistent with the preparation of compounds of formula (I). Heterocyclic chemistry conducted to prepare the compounds of the invention are not limited to the methods shown in Scheme 21. Moiety 21c containing appropriate G functionality such as aldehydes, ketones, halomethyl ketones, amides and the like may be manipulated with appropriate reagents to form moiety 21d, wherein $R_1$ is heterocyclyl, according to standard methods of organic synthesis (A. R. Katritzky; C. W. Rees; E. F. Scriven *Comprehensive Heterocyclic Chemistry* Vol. 2 to Vol. 9 (1996) Elsevier Science Ltd.).

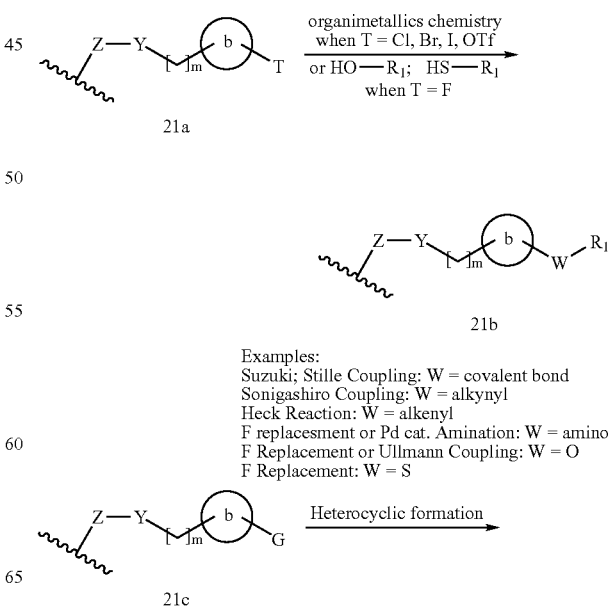

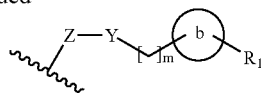

21d
R₁: heterocycles

Examples:
when G = -CHO, R₁:
imidazoles;benzoimidazoles;
oxazoles;
benzoxazoles; thiazoles;
benzothiazoles

EXAMPLES

Example 1

4-(4-Chloro-phenoxy)-N-(1-hydroxy-2-oxo-2,3,4,7-tetrahydro-1H-azepin-3-(R)-yl)-benzenesulfonamide Compound 1

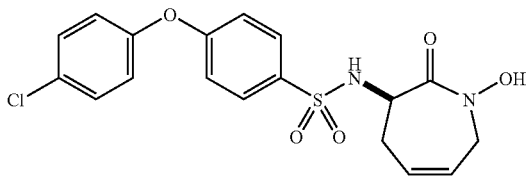

Step A. (1-Benzyloxycarbamoyl-but-3-(R)-enyl)-carbamic acid tert-butyl ester To a solution of 23.88 g of N-t-butoxycarbonyl-allyl-(D)-glycine in 200 mL of chloroform was added 32 g of N-ethyl-N-(dimethylaminopropyl)carbodiimide hydrochloride (EDCl), 15 g of 1-hydroxybenzotriazole, 12.2 mL of 4-N,N-dimethylamino-pyridine, and 15 mL of triethylamine. The solution was stirred at room temperature for 2 hours, and then 17.9 g of O-benzyl-hydroxylamine was added. The reaction was stirred at room temperature for 5 days. The solution was removed under vacuum. The mixture was taken up in ethyl acetate, and washed twice with 5% HCl (aq.) solution, followed by NaHCO₃ (aq.) and NaCl (aq.) solutions. The aqueous layers were re-extracted, and the organic layers combined and dried over Na₂SO₄(s). The reaction was filtered, and then the solvent removed under vacuum. The residue was diluted with Hexanes, and the resulting solids were filtered off and washed three times with Hexanes. The solids were dried to give 7.19 g of a white solid. An additional 3.28 g of material was obtained from the mother liquors (total=10.47 g). MS: 319 (M−H).

Step B. [1-(Allyl-benzyloxy-carbamoyl)-but-3-(R)-enyl]-carbamic acid tert-butyl ester To a solution of 8.36 g of (1-benzyloxycarbamoyl-but-3-(R)-enyl)-carbamic acid tert-butyl ester from Step A in 100 mL of tetrahydrofuran was added 17.8 g of cesium carbonate. The reaction was stirred at room temperature for 90 minutes, and then 14 mL of allyl bromide was added. The reaction was stirred for an additional 6 hours at room temperature. The reaction was then quenched with NH₄Cl (aq.) solution, and extracted with ethyl acetate. The organic layers were washed with NH₄Cl (aq.) and NaCl (aq.) solutions. The aqueous layers were re-extracted with ethyl acetate, and the organic layers combined and dried over Na₂SO₄(s). Filtration and solvent removal gave a white oily solid. This material was diluted with Hexanes, filtered, and then washed with Hexanes four times followed by drying. Gave 7.93 g of a white fluffy solid. MS: 743 (2M+Na), 383 (M+Na), 361 (M+H).

Step C. (1-Benzyloxy-2-oxo-2,3,4,7-tetrahydro-1H-azepin-3-(R)-yl)-carbamic acid tert-butyl ester To a solution of 7.93 g of [1-(allyl-benzyloxy-carbamoyl)-but-3-(R)-enyl]-carbamic acid tert-butyl ester from Step B in 900 mL of dichloromethane was added 750 mg of [(1,3-bis-(2,4,6-trimethylphenyl)-2-dimidazolylidene)dichloro-(phenylmethylene)-(tricyclohexylphosphine)ruthenium]. The reaction was stirred at room temperature for 8 hours, and then filtered over a plug of silica gel with excess dichloromethane. The dichloromethane layer was discarded, and then the silica plug was washed with 700 mL of a 3:4 Hexanes:ethyl acetate mixture. The solvent was removed under vacuum, then Hexanes were added, and the solids were filtered, washed with Hexanes three times and dried. Gave 6.5 g of a light brown solid. MS: 687 (2M+Na), 355 (M+Na).

Step D. 3-(R)-Amino-1-benzyloxy-1,3,4,7-tetrahydro-azepin-2-one

To a solution of 4.14 g (12.45 mmoles) of (1-benzyloxy-2-oxo-2,3,4,7-tetrahydro-1H-azepin-3-(R)-yl)-carbamic acid tert-butyl ester from Step C in 30 mL of dichloromethane was added 20 mL of trifluoroacetic acid. The reaction mixture was stirred for two hours at room temperature, and the solvent was removed under vacuum. Next, the reaction mixture was diluted in dichloromethane, and neutralized with NaHCO₃ (s). The reaction mixture was then extracted with NaHCO₃ (aq.) and NaCl (aq.) solutions. The aqueous layers were re-extracted with dichloromethane twice, and the organic layers combined and dried over Na₂SO₄(s). Filtration and solvent removal gave 3.685 g of a purple, viscous oil. MS: 465 (2M+H), 233 (M+H).

Step E. N-(1-Benzyloxy-2-oxo-2,3,4,7-tetrahydro-1H-azepin-3-(R)-yl)-4-(4-chloro-phenoxy)-benzenesulfonamide To a solution of 3.69 g of 3-(R)-amino-1-benzyloxy-1,3,4,7-tetrahydro-azepin-2-one from Step D in 30 mL of pyridine was added 6.28 g of 4-(4-chloro-phenoxy)-benzene sulfonyl chloride. The reaction was stirred at room temperature for 5 days. The reaction was extracted with ethyl acetate, and washed with 5% HCl (aq.) twice, NaHCO₃ (aq.) twice, and NaCl (aq.) once. The aqueous layers were re-extracted with ethyl acetate, and the organic layers combined and dried over Na₂SO₄(s). The reaction mixture was filtered and the solvent removed. The mixture was dissolved in dichloromethane, and filtered over silica gel. The dichloromethane layer was discarded. The silica gel was eluted with ethyl acetate, and the solvent removed under vacuum. Next, ethyl ether was added, and the solids collected under vacuum. The solids were washed with ethyl ether, and dried. Obtained 4.59 g of a white solid. MS: 521 (M+Na), 499 (M+H).

Step F. 4-(4-Chloro-phenoxy)-N-(1-hydroxy-2-oxo-2,3,4,7-tetrahydro-1H-azepin-3-(R)-yl)-benzenesulfonamide To a solution of 257 mg of N-(1-benzyloxy-2-oxo-2,3,4,7-tetrahydro-1H-azepin-3-(R)-yl)-4-(4-chloro-phenoxy)-benzenesulfonamide from Step E was added 6 mL of methane sulfonic acid. The reaction was stirred at room temperature for 16 hours. The reaction was poured over ice, and 50 mL of H$_2$O was added. The resulting solids were filtered, washed with H$_2$O (4 times), and dried. The solids were dissolved in ethyl acetate, and Hexanes was added after solvent reduction under vacuum. The resulting solids were filtered and washed with Hexanes (3 times), followed by drying. Obtained was 195 mg of a white solid (Compound 1). MS: 839 (2M+Na), 431 (M+Na), 409 (M+H).

Example 2

4'-Chloro-biphenyl-4-sulfonic acid (1-hydroxy-2-oxo-2,3,4,7-tetrahydro-1H-azepin-3-(R)-yl)-amide Compound 2

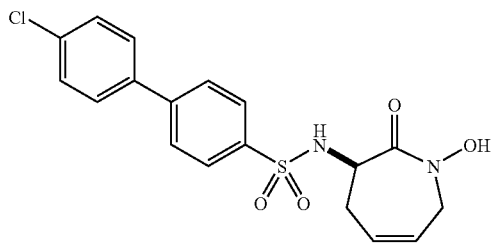

The titled compound was synthesized in a similar manner as described in Example 1 by replacing 4-(4-chloro-phenoxy)-benzene sulfonyl chloride with 4'-chloro-biphenyl-4-sulfonyl chloride in Step E. MS: 807 (2M+Na), 415 (M+Na), 393 (M+H).

Example 3

N-(1-Hydroxy-2-oxo-2,3,4,7-tetrahydro-1H-azepin-3-(R)-yl)-4-phenoxy-benzenesulfonamide Compound 3

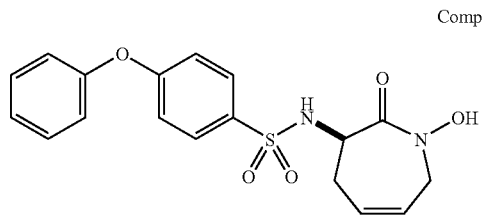

The titled compound was synthesized in a similar manner as described in Example 1 by replacing 4-(4-chloro-phenoxy)-benzene sulfonyl chloride with 4-phenoxy-benzenesulfonyl chloride in Step E. MS: 397 (M+Na), 375 (M+H).

Example 4

N-(1-Hydroxy-2-oxo-2,3,4,7-tetrahydro-H-azepin-3-(R)-yl)-4-(4-methoxy-phenoxy)-benzenesulfonamide Compound 4

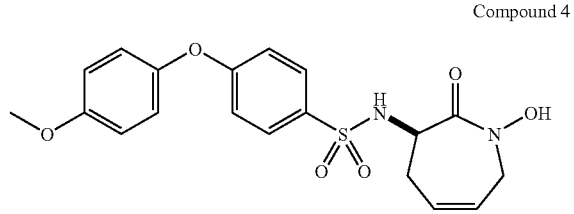

The titled compound was synthesized in a similar manner as described in Example 1 by replacing 4-(4-chloro-phenoxy)-benzene sulfonyl chloride with 4-(4-methoxy-phenoxy)-benzene sulfonyl chloride in Step E. MS: 427 (M+Na), 405 (M+H).

Example 5

N-(1-Hydroxy-2-oxo-2,3,4,7-tetrahydro-H-azepin-3-(R)-yl)-4-(4-trifluoro-methyl-phenoxy)-benzenesulfonamide Compound 5

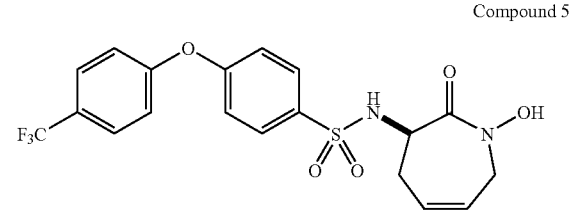

The titled compound was synthesized in a similar manner as described in Example 1 by replacing 4-(4-chloro-phenoxy)-benzene sulfonyl chloride with 4-(4-trifluoromethyl-phenoxy)-benzene sulfonyl chloride in Step E. MS: 907 (2M+Na), 465 (M+Na), 443 (M+H).

Example 6

N-(1-Hydroxy-2-oxo-2,3,4,7-tetrahydro-1H-azepin-3-(R)-yl)-4-(pyridin-4-yloxy)-benzenesulfonamide Compound 6

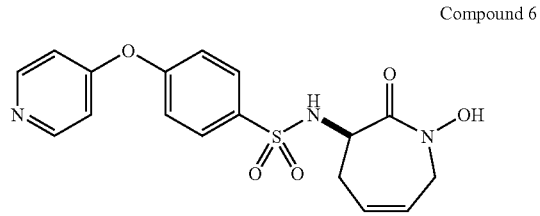

The titled compound was synthesized in a similar manner as described in Example 1 by replacing 4-(4-chloro-phenoxy)-benzene sulfonyl chloride with 4-(pyridin-4-yloxy)-benzenesulfonyl chloride in Step E. MS: 773 (2M+Na), 398 (M+Na), 376 (M+H).

Example 7

4-(3-Chloro-5-trifluoromethyl-pyridin-2-yloxy)-N-(1-hydroxy-2-oxo-2,3,4,7-tetrahydro-1H-azepin-3-(R)-yl)-benzenesulfonamide Compound 7

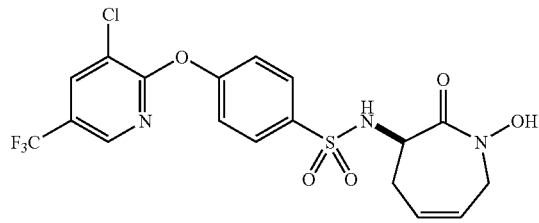

The titled compound was synthesized in a similar manner as described in Example 1 by replacing 4-(4-chloro-phenoxy)-benzene sulfonyl chloride with 4-(3-chloro-5-trifluoromethyl-phenoxy)-benzenesulfonyl chloride in Step E. MS: 977 (2M+Na), 500 (M+Na), 478 (M+H).

Example 8

N-(1-Hydroxy-2-oxo-2,3,4,7-tetrahydro-1H-azepin-3-(R)-yl)-4-(pyridin-2-yloxy)-benzenesulfonamide Compound 8

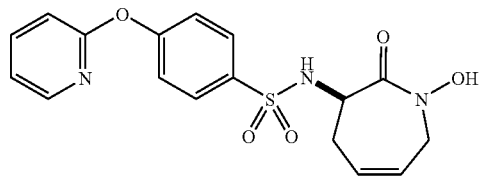

The titled compound was synthesized in a similar manner as described in Example 1 by replacing 4-(4-chloro-phenoxy)-benzene sulfonyl chloride with 4-(pyridin-2-yloxy)-benzenesulfonyl chloride in Step E. MS: 773 (2M+Na), 398 (M+Na), 376 (M+H).

Example 9

N-(1-Hydroxy-2-oxo-2,3,4,7-tetrahydro-1H-azepin-3-(R)-yl)-4-(4-phenyl-piperidin-1-yl)-benzenesulfonamide Compound 9

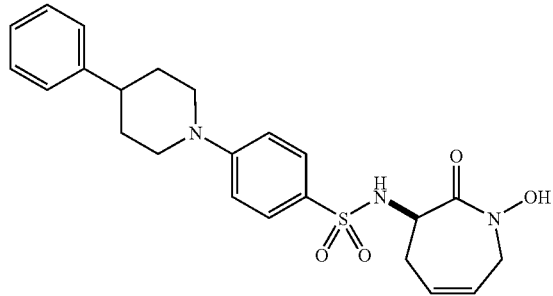

Step A. N-(1-Benzyloxy-2-oxo-2,3,4,7-tetrahydro-1H-azepin-3-(R)-yl)-4-fluoro-benzenesulfonamide To a solution of 551 mg of 3-(R)-amino-1-benzyloxy-1,3,4,7-tetrahydro-azepin-2-one from example 1 Step D in 4 mL of dichloromethane and 4 mL of pyridine was added 565 mg of 4-fluorophenyl sulfonyl chloride. The reaction was stirred at room temperature for 24 hours, and an additional 495 mg of the sulfonyl chloride was added. The reaction was stirred for an additional 24 hours, and then the reaction was extracted with ethyl acetate. The mixture was washed with 5% HCl (aq.), NaHCO₃(aq.), and NaCl(aq.) solutions. The aqueous layers were re-extracted with ethyl acetate, and the organic layers combined and dried over Na₂SO₄(s). Filtration and solvent removal gave a light brown solid. Dilution with ethyl ether, filtration, washing of the solids with ethyl ether and drying gave 548 mg of a light brown solid. MS: 391 (M+H).

Step B. N-(1-Benzyloxy-2-oxo-2,3,4,7-tetrahydro-1H-azepin-3-(R)-yl)-4-(4-phenyl-piperidin-1-yl)-benzenesulfonamide To a solution of 100 mg of N-(1-benzyloxy-2-oxo-2,3,4,7-tetrahydro-1H-azepin-3-(R)-yl)-4-fluoro-benzenesulfonamide from Step A in 2 mL of methylsulfoxide was added 100 mg of 4-phenyl piperidine. The solution was heated to 70° C. for 5 days. The reaction was cooled, and the mixture extracted with ethyl acetate. The organic layers were washed twice with NaCl(aq.) solution, followed by drying over Na₂SO₄(s). Filtration, solvent removal, was followed by dilution with ethyl ether. Filtration of the resulting solids, washing with ethyl ether and methanol, and drying gave 83 mg of an off-white solid. MS: 1063 (2M+H), 532 (M+H).

Step C. N-(1-Hydroxy-2-oxo-2,3,4,7-tetrahydro-1H-azepin-3-(R)-yl)-4-(4-phenyl-piperidin-1-yl)-benzenesulfonamide To 67 mg of N-(1-benzyloxy-2-oxo-2,3,4,7-tetrahydro-1H-azepin-3-(R)-yl)-4-(4-phenyl-piperidin-1-yl)-benzenesulfonamide from Step B was added 2 mL of methanesulfonic acid. The reaction was stirred for 2 days. The mixture was then diluted in water, followed by neutralization with NaHCO₃(s). The aqueous layers were then extracted with ethyl acetate and washed with NaCl(aq.) solution. The organic layer was separated and dried over Na₂SO₄(s). The solution was filtered, and the solvent was removed under vacuum. Methanol was added to the residue, and the resulting solids were filtered and washed with methanol. Drying gave 20 mg of a light orange solid (Compound 9). MS: 905 (2M+Na), 442 (M+H).

Example 10

N-(1-Hydroxy-2-oxo-2,3,4,7-tetrahydro-1H-azepin-3-(R)-yl)-4-(4-phenyl-piperazin-1-yl)-benzenesulfonamide Compound 10

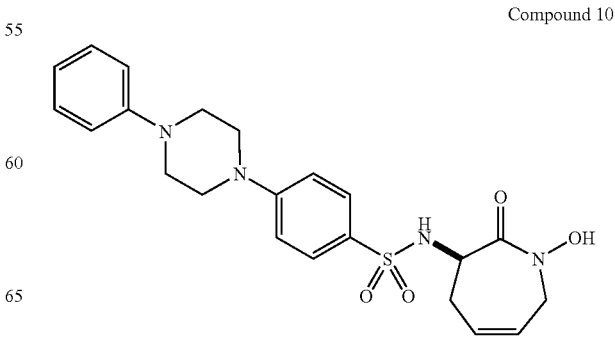

The titled compound was synthesized in a similar manner as described in Example 9 by replacing 4-phenyl piperidine with 1-phenyl-piperazine in Step B. MS: 907 (2M+Na), 443 (M+H).

Example 11

4-(4-Chloro-phenoxy)-N-(1-hydroxy-2-oxo-2,3,4,7-tetrahydro-1H-azepin-3-(R)-yl)-N-(2-morpholin-4-yl-ethyl)-benzenesulfonamide Compound 11

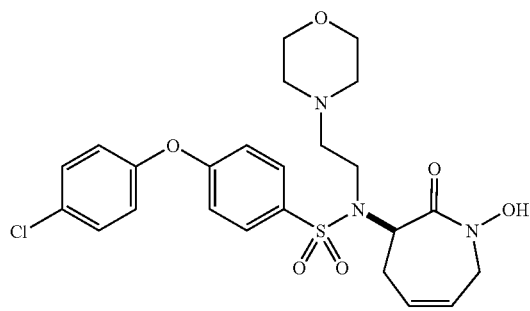

Step A. N-(1-Benzyloxy-2-oxo-2,3,4,7-tetrahydro-1H-azepin-3-(R)-yl)-4-(4-chloro-phenoxy)-N-(2-morpholin-4-yl-ethyl)-benzenesulfonamide To a solution of 1.51 g of N-(1-benzyloxy-2-oxo-2,3,4,7-tetrahydro-1H-azepin-3-(R)-yl)-4-(4-chloro-phenoxy)-benzenesulfonamide from Example 1 Step E in 20 mL of methylsulfoxide (DMSO) was added 2.9 g of $Cs_2CO_3$(s) and 1.2 g of 4-(2-chloroethyl)-morpholine hydrochloride. The mixture was heated to 50° C. for 1 hour. The reaction was cooled, and then dissolved with ethyl acetate. The organic layer was washed with $NH_4Cl$(aq) and NaCl(aq) solutions. The aqueous layers were re-extracted with ethyl acetate, and the organic layers were combined and dried over $Na_2SO_4$(s). Filtration and solvent removal was followed by column chromatography on silica gel using a hexanes-ethyl acetate gradient. Obtained 1.48 g of a pale brown oil (80% yield). MS: 612 (M+H).

Step B. 4-(4-Chloro-phenoxy)-N-(1-hydroxy-2-oxo-2,3,4,7-tetrahydro-1H-azepin-3-(R)-yl)-N-(2-morpholin-4-yl-ethyl)-benzenesulfonamide To a solution of 2.83 g of N-(1-Benzyloxy-2-oxo-2,3,4,7-tetrahydro-1H-azepin-3-(R)-yl)-4-(4-chloro-phenoxy)-N-(2-morpholin-4-yl-ethyl)-benzenesulfonamide from Step B was added 35 mL of methane sulfonic acid. The reaction was stirred at room temperature for 20 hours. The reaction was then poured over ice. The aqueous layer was extracted with 100 mL of ethyl ether twice, followed by extraction of the aqueous layer with dichloromethane (4 times). The dichloromethane layers were combined and dried over $Na_2SO_4$(s). The liquids were filtered off, and solvent removal gave a light yellow film. Dilution with ethyl ether, filtration of the resulting solids, and washing with ethyl ether and hexanes followed by drying gave 2.56 g of an orange solid. MS: 522 (M+H).

Example 12

4-(4-Chloro-phenoxy)-N-(1-hydroxy-2-oxo-2,3,4,7-tetrahydro-1H-azepin-3-(R)-yl)-N-methyl-benzenesulfonamide Compound 12

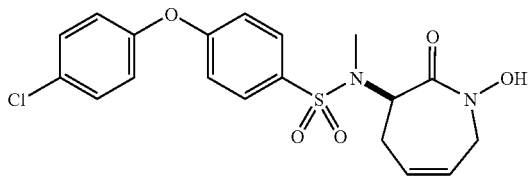

The titled compound was synthesized in a similar manner as described in Example 11 by replacing 4-(2-chloroethyl)-morpholine hydrochloride with methyl iodide in Step A. MS: 867 (2M+Na), 445 (M+Na), 423 (M+H).

Example 13

4-(4-Chloro-phenoxy)-N-(1-hydroxy-2-oxo-2,3,4,7-tetrahydro-1H-azepin-3-(R)-yl)-N-(2-piperidin-1-yl-ethyl)-benzenesulfonamide Compound 13

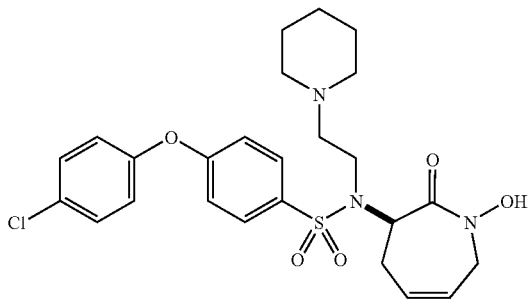

The titled compound was synthesized in a similar manner as described in Example 11 by replacing 4-(2-chloroethyl)-morpholine hydrochloride with 1-(2-chloro-ethyl)-piperidine in Step A. MS: 520 (M+H).

Example 14

4-(4-Chloro-phenoxy)-N-(1-hydroxy-2-oxo-2,3,4,7-tetrahydro-1H-azepin-3-(R)-yl)-N-[2-(4-methyl-piperazin-1-yl)-ethyl]-benzenesulfonamide Compound 14

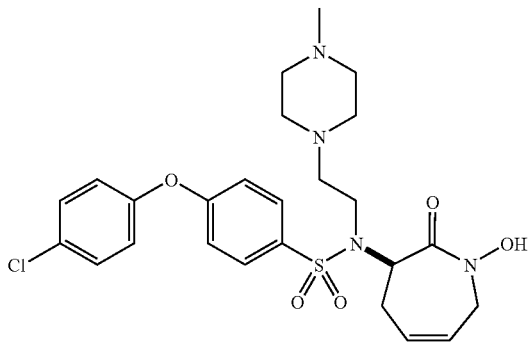

The titled compound was synthesized in a similar manner as described in Example 11 by replacing 4-(2-chloroethyl)-morpholine hydrochloride with 1-(2-chloro-ethyl)-1-methyl-piperazine (*Chem. & Pharm. Bull.* 1987, 35, 1953-68) in Step A. MS: 535 (M+H)

Example 15

(4-Chloro-phenyl)-N-(1-hydroxy-2-oxo-2,3,4,7-tetrahydro-1H-azepin-3-(R)-yl)-methanesulfonamide Compound 15

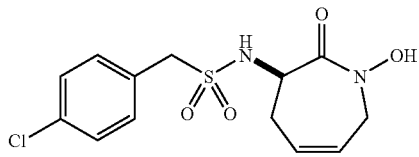

The titled compound was synthesized in a similar manner as described in Example 11 by replacing 4-(4-chloro-phenoxy)-benzene sulfonyl chloride with (4-chloro-phenyl)-methanesulfonyl chloride in Step E. MS: 331.8 (M+H).

Example 16

5-Bromo-thiophene-2-sulfonic acid (1-hydroxy-2-oxo-2,3,4,7-tetrahydro-1H-azepin-3-(R)-yl)-amide Compound 16

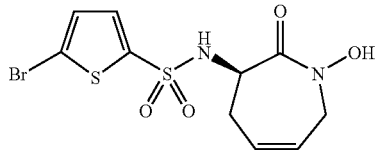

The titled compound was synthesized in a similar manner as described in Example 1 by replacing 4-(4-chloro-phenoxy)-benzene sulfonyl chloride with 5-bromo-thiophene-2-sulfonyl chloride in Step E. MS: 368, 370 (M+H).

Example 17

5-(4-Methoxy-phenyl)-thiophene-2-sulfonic acid (1-hydroxy-2-oxo-2,3,4,7-tetrahydro-1H-azepin-3-(R)-yl)-amide Compound 17

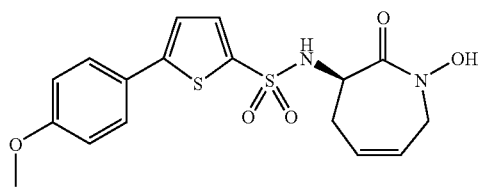

Step A. (R)-5-(4-Methoxy-phenyl)-thiophene-2-sulfonic acid (1-benzyloxy-2-oxo-2,3,4,7-tetrahydro-1H-azepin-3-yl)-amide (R)-5-Bromo-thiophene-2-sulfonic acid (1-benzyloxy-2-oxo-2,3,4,7-tetrahydro-1H-azepin-3-yl)-amide (100 mg, 0.28 mmol) from example 16 was dissolved in THF (3 mL). (4-Methoxyphenyl) boronic acid (64 mg, 0.42 mmol), potassium carbonate (80 mg, 0.56 mmol) and tetrakis(triphenylphosphine)palladium (16 mg, 0.014 mmol) were added at room temperature. The mixture in a sealed vessel was irradiated in microwave oven at 150° C. for 20 min. The resulting reaction mixture was filtered. The solids were washed with water and 1:1 Ether-hexane, then dried under vacuum to give the desired product (70 mg, 51% yield). MS: 485, 487 (M+H).

Step B. 5-(4-Methoxy-phenyl)-thiophene-2-sulfonic acid (1-hydroxy-2-oxo-2,3,4,7-tetrahydro-1H-azepin-3-(R)-yl)-amide The titled compound was prepared in a similar manner as described in Example 1, Step F. MS: 410, 412 (M+H).

Example 18

(R)-5-Bromo-thiophene-2-sulfonic acid (1-hydroxy-2-oxo-2,3,4,7-tetrahydro-1H-azepin-3-yl)-(2-morpholin-4-yl-ethyl)-amide Compound 18

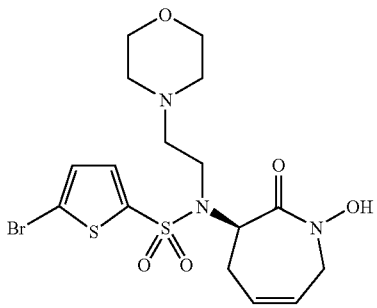

The titled compound was synthesized in a similar manner as described in Example 11 by replacing N-(1-benzyloxy-2-oxo-2,3,4,7-tetrahydro-1H-azepin-3-(R)-yl)-4-(4-chlorophenoxy)-benzenesulfonamide with 5-bromo-thiophene-2-sulfonic acid (1-benzyloxy-2-oxo-2,3,4,7-tetrahydro-1H-azepin-3-(R)-yl)-amide (obtained from example 16) in Step A. MS: 481, 482 (M+H).

Example 19

4-(4-Chloro-phenoxy)-N-(1-hydroxy-6-morpholin-4-ylmethyl-2-oxo-2,3,4,7-tetrahydro-1H-azepin-3-(R)-yl)-benzenesulfonamide Compound 19

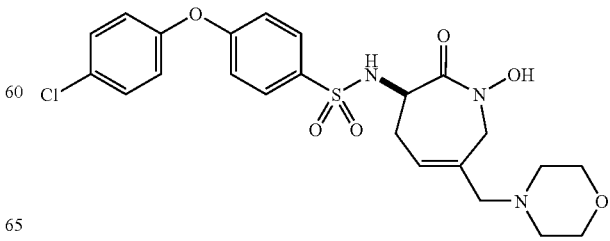

Step A. {1-[Benzyloxy-(2-chloromethyl-allyl)-carbamoyl]-but-3-(R)-enyl}-carbamic acid tert-butyl ester To a solution of 235 mg of (1-benzyloxycarbamoyl-but-3-(R)-enyl)-carbamic acid tert-butyl ester from Example 1 Step A in 8 mL of tetrahydrofuran was added 635 mg of cesium carbonate. The reaction was heated to 60° C. for 60 minutes, and then 1 mL of 2-chloro-3-methallyl chloride was added. The reaction was heated for an additional 20 hours. The reaction was then cooled, quenched with NH$_4$Cl(aq.) solution, and extracted with ethyl acetate. The organic layers were washed with NH$_4$Cl(aq.) and NaCl(aq.) solutions. The aqueous layers were re-extracted with ethyl acetate, and the organic layers combined and dried over Na$_2$SO$_4$(s). Filtration and solvent removal gave a white oily solid. Column chromatography (Hexanes/ethyl acetate gradient) on silica gel, followed by fraction combination, and solvent removal gave 170 mg of a white solid (57% yield). MS: 839 (2M+Na), 431 (M+Na).

Step B. (1-Benzyloxy-6-chloromethyl-2-oxo-2,3,4,7-tetrahydro-1H-azepin-3-(R)-yl)-carbamic acid tert-butyl ester To a solution of 179 mg of {1-[Benzyloxy-(2-chloromethyl-allyl)-carbamoyl]-but-3-(R)-enyl}-carbamic acid tert-butyl ester in 20 mL of 1,2-dichloroethane was added 16 mg of [(1,3-bis-(2,4,6-trimethylphenyl)-2-dimidazolylidene) dichloro-(phenylmethylene)-(tricyclohexylphosphine)ruthenium]. The mixture was heated in a microwave oven at 150° C. for 15 minutes. This process was repeated twice more. The respective vials were combined, and filtered over a plug of silica gel with additional dichloromethane. The dichloromethane layer was discarded, and the silica plug was eluted with 300 mL of 1:1 Hexanes:ethyl acetate. The solvent was removed under vacuum, and the residue was purified by column chromatography (Hexanes/ethyl acetate gradient on silica gel). Obtained 238 mg of an off white solid after fraction combination and solvent removal. MS: 783 (2M+Na), 403 (M+Na).

Step C. (1-Benzyloxy-6-morpholin-4-ylmethyl-2-oxo-2,3,4,7-tetrahydro-1H-azepin-3-(R)-yl)-carbamic acid tert-butyl ester To a solution of 234 mg of (1-Benzyloxy-6-chloromethyl-2-oxo-2,3,4,7-tetrahydro-1H-azepin-3-(R)-yl)-carbamic acid tert-butyl ester in 10 mL of acetonitrile was added 0.5 mL of morpholine. The mixture was heated to 65° C. for 2 hours. The reaction was cooled and the mixture was extracted with ethyl acetate. The organic layer was washed with NaHCO$_3$ (aq.) and NaCl (aq.) solutions. The aqueous layers were re-extracted with ethyl acetate, and the organic layers were combined and dried over Na$_2$SO$_4$(s). Filtration and solvent removal gave 270 mg of a clear oil. MS: 454 (M+Na), 432 (M+H).

Step D. N-(1-Benzyloxy-6-morpholin-4-ylmethyl-2-oxo-2,3,4,7-tetrahydro-1H-azepin-3-(R)-yl)-4-(4-chloro-phenoxy)-benzenesulfonamide To a solution of 270 mg of (1-Benzyloxy-6-morpholin-4-ylmethyl-2-oxo-2,3,4,7-tetrahydro-1H-azepin-3-(R)-yl)-carbamic acid tert-butyl ester in 10 mL of dichloromethane was added 5 mL of trifluoroacetic acid. The mixture was stirred at room temperature for 2 hours. The volatiles were removed under vacuum. Next, NaHCO$_3$(s) was added to neutralize the salts. The mixture was then extracted with dichloromethane followed by washing with NaHCO$_3$(aq.) and NaCl (aq.) solutions. The aqueous layers were re-extracted with dichloromethane twice, and the organic layers combined and dried over Na$_2$SO$_4$(s). The solution was then filtered and the solvent removed. The residue was then taken up in 6 mL of pyridine, and 310 mg of 4-(4-chloro-phenoxy)-phenyl sulfonyl chloride was added. The mixture was stirred at room temperature for 3 days. The pyridine was then removed under vacuum, and the mixture was diluted with ethyl acetate. The organic layer was washed three times with NaHCO$_3$(aq.) solution. The aqueous layers were re-extracted twice, and the organics combined and dried over Na$_2$SO$_4$(s). Filtration and solvent removal gave a residue which was diluted with ethyl ether. The solids were filtered and washed with ethyl ether. Drying gave 251 mg of an off-white solid. MS: 620 (M+Na), 598 (M+H).

Step E. 4-(4-Chloro-phenoxy)-N-(1-hydroxy-6-morpholin-4-ylmethyl-2-oxo-2,3,4,7-tetrahydro-1H-azepin-3-(R)-yl)-benzenesulfonamide To 251 mg of N-(1-Benzyloxy-6-morpholin-4-ylmethyl-2-oxo-2,3,4,7-tetrahydro-1H-azepin-3-(R)-yl)-4-(4-chloro-phenoxy)-benzenesulfonamide was added 8 mL of methanesulfonic acid. The reaction was stirred at room temperature for 20 hours, and then the solution was poured over ice. After the ice melted, the aqueous layer was extracted with ethyl ether. The aqueous layer was then neutralized with NaHCO$_3$(s). The aqueous layers were then extracted with dichloromethane three times. The organic layers were then washed with NaCl(aq.) solution, and dried over Na$_2$SO$_4$(s). Filtration and solvent removal was followed by filtration over silica gel and elution with an ethyl acetate methanol mixture (4:1). Solvent removal, dilution with ethyl ether, filtration of the solids and drying gave 105 mg of a beige solid. MS: 1037 (2M+Na), 530 (M+Na), 508 (M+H).

Example 20

(R)-4-(4-Chloro-phenoxy)-N-(1-hydroxy-6-methyl-2-oxo-2,3,4,7-tetrahydro-1H-azepin-3-yl)-benzenesulfonamide Compound 20

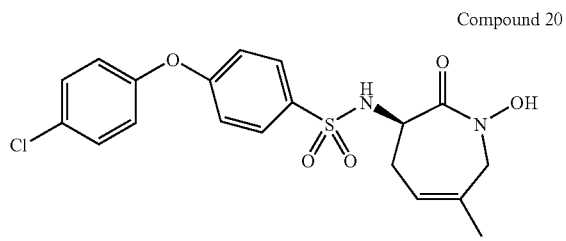

The titled compound was synthesized in a similar manner as described in Example 19 (but omit Step C) by replacing 2-chloro-3-methallyl chloride with 3-chloro-2-methyl-propene in Step A. MS: 424 (M+H).

Example 21

(R)-4-(4-Chloro-phenoxy)-N-[6-(2,6-dimethyl-morpholin-4-ylmethyl)-1-hydroxy-2-oxo-2,3,4,7-tetrahydro-1H-azepin-3-yl]-benzenesulfonamide Compound 21

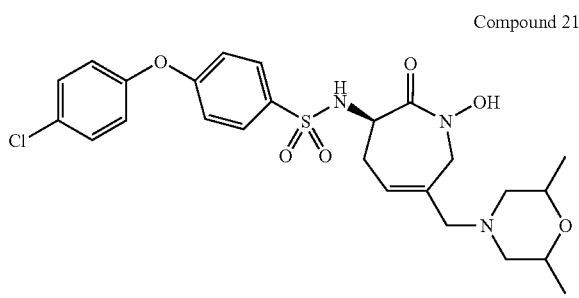

The titled compound was synthesized in a similar manner as described in Example 19 by replacing morpholine with 2,6-dimethyl-morpholine in Step C. MS: 424 (M+H).

Example 22

N-Benzyl-N-(1-hydroxy-2-oxo-1,2-dihydro-pyridin-3-yl)-4-phenoxy-benzene-sulfonamide Compound 22

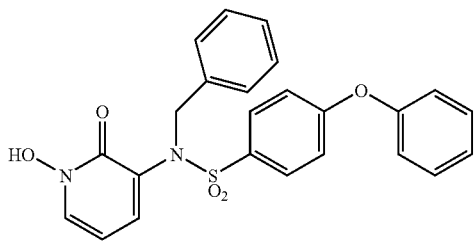

Step A. N-(2-Bromo-pyridin-3-yl)-4-phenoxy-benzenesulfonamide

To a solution of 2-bromo-3-aminopyridine (0.69 g, 3.98 mmol) in dry pyridine (15 mL) was added a solution of 4-phenoxy-benzenesulfonyl chloride (1.03 g, 3.98 mmol) in pyridine (3 mL) at 0 C. The resulting mixture was allowed to warm to room temperature and stirred until TCL showed the completion of the reaction. The reaction mixture was diluted with EtOAc and washed with aqueous HCl solution. After the pyridine was neutralized, the organics were washed with water, brine and dried over anhydrous $Na_2SO_4$. The filtration (Celite) and concentration under vacuo gave a crude material, which was purified by silica column (30% EtOAc/hexanes). MS: 405, 407 (M+H)$^+$.

Step B. N-Benzyl-N-(2-bromo-pyridin-3-yl)-4-phenoxy-benzenesulfonamide

To a suspension of N-(2-bromo-pyridin-3-yl)-4-phenoxy-benzene-sulfonamide (0.38 g, 0.94 mmol) from step A and $K_2CO_3$ (0.39 g, 2.81 mmol) in dry DMF (10 mL) was added benzylbromide (0.13 mL, 1.13 mmol). The resulting mixture was heated at 80 C overnight. The cooled reaction was diluted with EtOAc and water. The aqueous layer was extracted with EtOAc (×3) and the combined organics were washed with water and brine, dried over anhydrous $Na_2SO_4$, and filtered through Celite. The filtrate was concentrated under the reduced pressure and purified by chromatography (silica gel, 25% EtOAc/hexanes). MS: 495, 497 (M+H)$^+$.

Step C. N-Benzyl-N-(2-bromo-1-oxy-pyridin-3-yl)-4-phenoxy-benzenesulfon-amide A mixture of N-benzyl-N-(2-bromo-pyridin-3-yl)-4-phenoxy-benzenesulfonamide (0.23 g, 0.46 mmol) from step B and mCPBA (max. 77%, 0.21 g) in $CH_2Cl_2$ (5 mL) was stirred at room temperature for 2 days. The reaction was diluted with $CH_2Cl_2$ and water. The organic layer was washed with 10% aqueous $Na_2SO_3$ solution, 1N NaOH solution and water subsequently. The organic portion was then concentrated under the reduced pressure and purified by chromatography (silica gel, 1% MeOH/EtOAc). MS: 511, 513 (M+H)$^+$.

Step D. N-Benzyl-N-(2-methoxy-1-oxy-pyridin-3-yl)-4-phenoxy-benzenesulfon amide To a solution of N-benzyl-N-(2-bromo-1-oxy-pyridin-3-yl)-4-phenoxy-benzenesulfon-amide (0.13 g, 0.26 mmol) from step C in anhydrous MeOH (3 mL) was added NaOMe (25 wt % in MeOH, 0.06 mL) and the resulting solution was heated to reflux. After TCL indicated the completion of the reaction, the solvent was removed under the reduced pressure. The crude material was dissolved in $CH_2Cl_2$ and washed with water. After the usual work-up, the crude product was purified by chromatography (silica gel, 8% MeOH/EtOAc). MS: 463 (M+H)$^+$.

Step E. N-Benzyl-N-(1-hydroxy-2-oxo-1,2-dihydro-pyridin-3-yl)-4-phenoxy-benzene-sulfonamide A solution of N-benzyl-N-(2-methoxy-1-oxy-pyridin-3-yl)-4-phenoxy-benzene-sulfonamide (0.08 g, 0.17 mmol) from step D in MeOH (2 mL) was treated with 2N HCl (1.5 mL). The mixture was heated to reflux for 1 h. The reaction was cooled to room temperature, and the solvent was removed. The resulting solid was washed with water and a mixture of $Et_2O$/hexanes (1:2) to give the final product. MS: 449 (M+H)$^+$.

Example 23

N-Benzyl-N-(1-hydroxy-2-thioxo-1,2-dihydro-pyridin-3-yl)-4-phenoxy-benzene-sulfonamide Compound 23

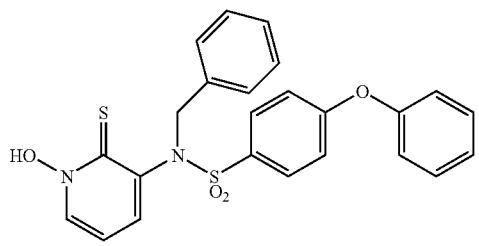

A solution of N-benzyl-N-(2-bromo-1-oxy-pyridin-3-yl)-4-phenoxy-benzenesulfon-amide (0.06 g, 0.12 mmol) from Example 22 step C in DMSO/H$_2$O (0.3 mL/2 mL) was treated with NaHS hydrate (0.48 mmol, 0.026 g). The resulting mixture was heated to reflux for 30 min. After the usual work-up, the crude material was purified by chromatography (silica gel, 70% EtOAc/hexanes) to give the titled compound. MS: 465 (M+H)$^+$.

Example 24

N-(1-Hydroxy-2-oxo-1,2-dihydro-pyridin-3-yl)-N-isobutyl-4-phenoxy-benzenesulfonamide Compound 24

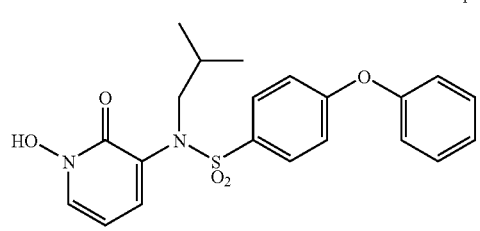

The titled compound was synthesized in a similar manner as described in Example 22 by replacing benzylbromide with isopropyl iodide in Step B. MS: 415 (M+H)$^+$.

Example 25

N-(1-Hydroxy-2-oxo-1,2-dihydro-pyridin-3-yl)-N-methyl-4-phenoxy-benzene-sulfonamide Compound 25

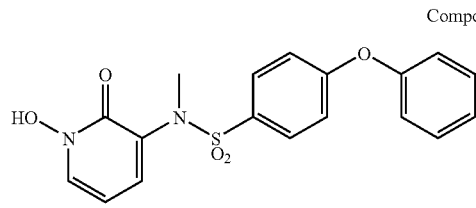

The titled compound was synthesized in a similar manner as described in Example 22 by replacing benzylbromide with methyl iodide in Step B. MS: 373 (M+H)$^+$.

Example 26

N-(1-Hydroxy-2-oxo-1,2-dihydro-pyridin-3-yl)-N-methyl-4-p-tolyloxy-benzene-sulfonamide Compound 26

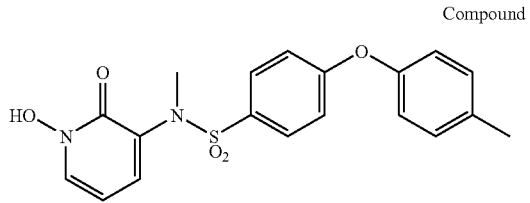

The titled compound was synthesized in a similar manner as described in Example 22 by replacing 4-phenoxy-benzenesulfonyl chloride with 4-p-tolyloxy-benzenesulfonyl chloride in step A, and replacing benzylbromide with methyl iodide in step B. MS: 387 (M+H)$^+$.

Example 27

N-Ethyl-N-(1-hydroxy-2-oxo-1,2-dihydro-pyridin-3-yl)-4-p-tolyloxy-benzene-sulfonamide Compound 27

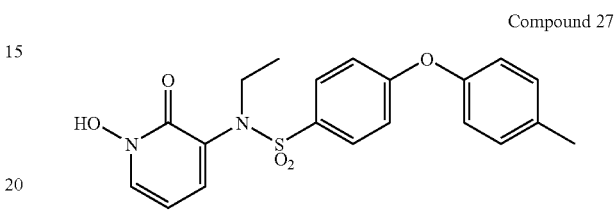

The titled compound was synthesized in a similar manner as described in Example 22 by replacing 4-phenoxy-benzenesulfonyl chloride with 4-p-tolyloxy-benzenesulfonyl chloride in Step A, and replacing benzylbromide with ethyl iodide in Step B. MS: 401 (M+H)$^+$.

Example 28

4-(4-Chloro-phenoxy)-N-(1-hydroxy-2-oxo-1,2-dihydro-pyridin-3-yl)-N-methyl-benzenesulfonamide Compound 28

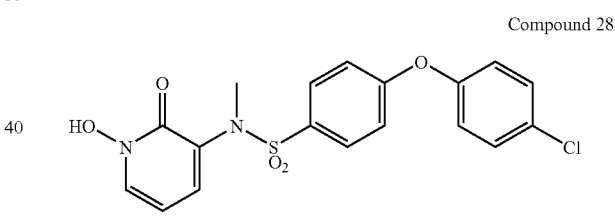

The titled compound was synthesized in a similar manner as described in Example 22 by replacing 4-phenoxy-benzenesulfonyl chloride with 4-(4-chloro-phenoxy)-benzenesulfonyl chloride in Step A, and replacing benzylbromide with methyl iodide in Step B. MS: 407 (M+H)$^+$.

Example 29

N-(1-Hydroxy-2-oxo-1,2-dihydro-pyridin-3-yl)-4-(4-methoxy-phenoxy)-N-methyl-benzenesulfonamide Compound 29

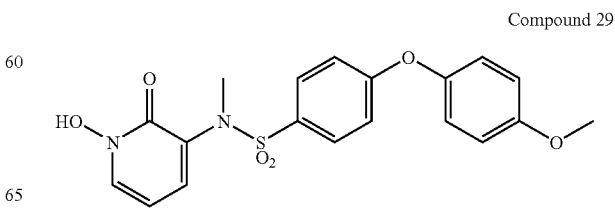

The titled compound was synthesized in a similar manner as described in Example 22 by replacing 4-phenoxy-benzenesulfonyl chloride with 4-(4-methoxy-phenoxy)-benzenesulfonyl chloride in Step A, and replacing benzylbromide with methyl iodide in Step B. MS: 403 (M+H)+.

Example 30

N-(1-Hydroxy-2-oxo-1,2-dihydro-pyridin-3-yl)-N-methyl-4-(4-trifluoromethyl-phenoxy)-benzenesulfonamide

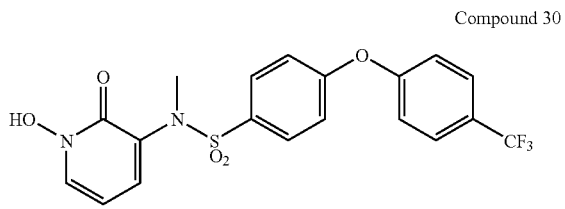

Compound 30

The titled compound was synthesized in a similar manner as described in Example 22 by replacing 4-phenoxy-benzenesulfonyl chloride with 4-(4-trifluoromethyl-phenoxy)-benzenesulfonyl chloride in Step A, and replacing benzylbromide with methyl iodide in Step B. MS: 441 (M+H)+.

Example 31

4-(4-Chloro-phenoxy)-N-(1-hydroxy-4-methyl-2-oxo-1,2-dihydro-pyridin-3-yl)-N-methyl-benzenesulfonamide

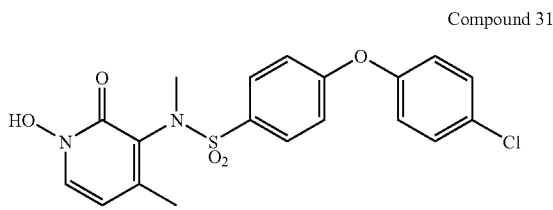

Compound 31

The titled compound was synthesized in a similar manner as described in Example 22 by replacing 2-bromo-3-aminopyridine with 2-bromo-3-amino-4-methyl-pyridine and replacing 4-phenoxy-benzenesulfonyl chloride with 4-(4-trifluoromethyl-phenoxy)-benzenesulfonyl chloride in Step A, and replacing benzylbromide with methyl iodide in Step B. MS: 421 (M+H)+.

Example 32

N-(5-Bromo-1-hydroxy-2-oxo-1,2-dihydro-pyridin-3-yl)-4-(4-chloro-phenoxy)-N-methyl-benzenesulfonamide

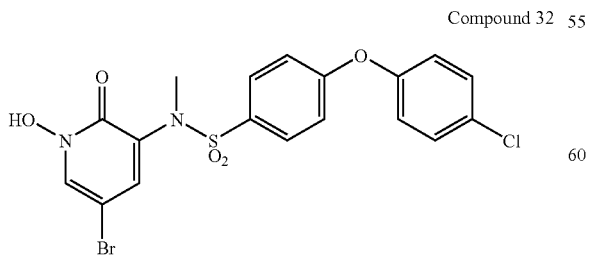

Compound 32

The titled compound was synthesized in a similar manner as described in Example 22, except for step A and step C, which are described as below. MS: 485, 487 (M+H)+.

Step A. 4-(4-Chloro-phenoxy)-N-(2,5-dibromo-pyridin-3-yl)-benzenesulfonamide

To a solution of 2,5-dibromo-3-aminopyridine (0.51 g, 2.0 mmol) and 4-(4-chloro-phenoxy)-benzenesulfonyl chloride (0.76 g, 2.0 mmol) in dry CH$_2$Cl$_2$ (10 mL) was added pyridine (1 mL) at 0 C. The resulting mixture was allowed to warm to room temperature and stirred until TCL showed the completion of the reaction. The reaction mixture was diluted with CH$_2$Cl$_2$ and washed with aqueous HCl solution. After the pyridine was neutralized, the organics were washed with water, brine and dried over anhydrous Na$_2$SO$_4$. The filtration (Celite) and concentration under vacuo gave a crude material, which was purified by silica column (30% EtOAc/hexanes). MS: 516, 518 (M+H)+.

Step B. 4-(4-Chloro-phenoxy)-N-(2,5-dibromo-pyridin-3-yl)-N-methyl-benzene-sulfonamide The titled compound was synthesized in a similar manner as described in example 1 step B by replacing benzylbromide with methyl iodide. MS: 530, 532 (M+H)+.

Step C. 4-(4-Chloro-phenoxy)-N-(2,5-dibromo-1-oxy-pyridin-3-yl)-N-methyl-benzenesulfonamide To a solution of 4-(4-chloro-phenoxy)-N-(2,5-dibromo-pyridin-3-yl)-N-methyl-benzene-sulfonamide (0.53 g, 1.0 mmol) from step B in TFA (5 mL) was added H$_2$O$_2$ (30% in water, 3.7 mL) slowly. The resulting mixture was heated at 60° C. and the reaction was monitored by HPLC. After the reaction was completed, the mixture was carefully neutralized with aqueous NaOH solution under the ice-bath cooling, extracted with CH$_2$Cl$_2$ (×3), and then followed by usual work-up. The crude material was purified by chromatography (silica gel, 1% MeOH/EtOAc). MS: 546, 548 (M+H)+.

Example 33

4-(4-Chloro-phenoxy)-N-(1-hydroxy-6-methyl-2-oxo-1,2-dihydro-pyridin-3-yl)-N-methyl-benzenesulfonamide

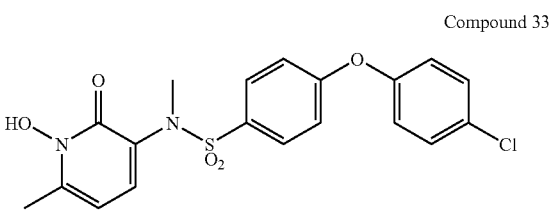

Compound 33

The titled compound was synthesized in a similar manner as described in Example 22 by replacing 2-bromo-3-aminopyridine with 2-bromo-3-amino-6-methyl-pyridine and replacing 4-phenoxy-benzenesulfonyl chloride with 4-(4-trifluoromethyl-phenoxy)-benzenesulfonyl chloride in Step A, and replacing benzylbromide with methyl iodide in Step B; and the procedure of Step C was followed by Example 32 Step C. MS: 421 (M+H)+.

Example 34

N-(1-Hydroxy-2-oxo-1,2-dihydro-pyridin-3-yl)-N-(2-morpholin-4-yl-ethyl)-4-p-tolyloxy-benzene-sulfonamide Compound 34

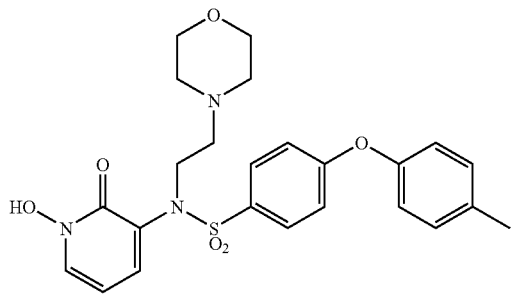

The titled compound was synthesized in a similar manner as described in Example 22 by replacing 4-phenoxy-benzenesulfonyl chloride with 4-(4-methyl-phenoxy)-benzenesulfonyl chloride in Step A; and replacing benzylbromide with 4-(2-chloro-ethyl)-morpholine in Step B. MS: 486 (M+H)$^+$.

Example 35

4-(4-Chloro-phenoxy)-N-(1-hydroxy-2-oxo-1,2-dihydro-pyridin-3-yl)-N-(2-morpholin-4-yl-2-oxo-ethyl)-benzenesulfonamide Compound 35

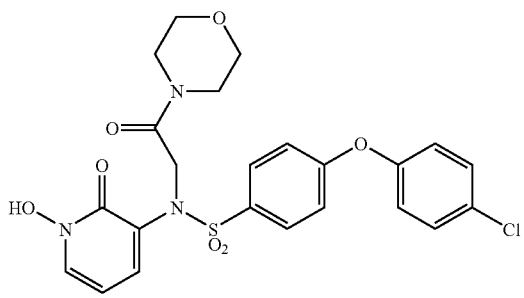

The titled compound was synthesized in a similar manner as described in Example 22 by replacing 4-phenoxy-benzenesulfonyl chloride with 4-(4-chloro-phenoxy)-benzenesulfonyl chloride in Step A; and replacing benzylbromide with 2-chloro-1-morpholin-4-yl-ethanone in Step B. MS: 520 (M+H)$^+$.

Example 36

4'-Chloro-biphenyl-4-sulfonic acid (1-hydroxy-2-oxo-1,2-dihydro-pyridin-3-yl)-methyl-amide Compound 36

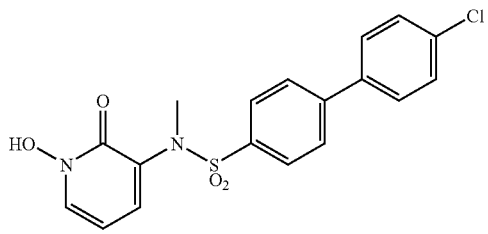

The titled compound was synthesized in a similar manner as described in Example 22, except that in step A 4-phenoxy-benzenesulfonyl chloride was replaced with 4-chlorobiphenylsulfonyl chloride; and in step B benzylbromide was replaced with methyl iodide. MS: 441 (M+H)$^+$.

Example 37

4-(4-Chloro-phenoxy)-N-(1-hydroxy-2-oxo-1,2-dihydro-pyridin-3-yl)-benzene-sulfonamide Compound 37

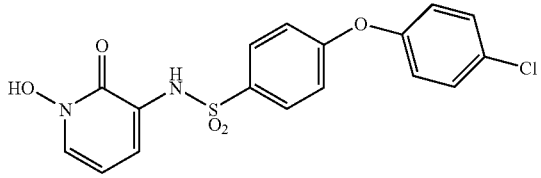

Step A. 4-(4-Chloro-phenoxy)-N-(2-methoxy-pyridin-3-yl)-benzenesulfonamide

The titled compound was synthesized in a similar manner as described in Example 22, step A by replacing 2-bromo-3-amino-pyridine with 2-methoxy-3-amino-pyridine and replacing 4-phenoxy-benzenesulfonyl chloride with 4-chlorobiphenylsulfonyl chloride. MS: 391 (M+H)$^+$.

Step B. 4-(4-Chloro-phenoxy)-N-(2-methoxy-1-oxy-pyridin-3-yl)-benzene-sulfonamide To a solution of 4-(4-chloro-phenoxy)-N-(2-methoxy-pyridin-3-yl)-benzene-sulfonamide (0.39 g, 1.0 mmol) from Step A in dry CH$_2$Cl$_2$ (10 mL) was added urea hydrogen peroxide complex (0.197 g, 2.1 mmol) at 0° C. Trifluoroacetic anhydride (0.42 g, 2.0 mmol) was then slowly added to the reaction mixture (the reaction is exothermic). After 30 min, the reaction was warmed to room temperature and stirred for 3 h. The reaction was quenched with an aqueous solution of Na$_2$SO$_3$ and stirred for 15 min to destroy any residual peroxides. After the usual work-up (CH$_2$Cl$_2$ extraction), the crude material was purified by chromatography (silica gel, 8% MeOH/EtOAc) to provide the desired product. MS: 407 (M+H)$^+$.

Step C. 4-(4-Chloro-phenoxy)-N-(1-hydroxy-2-oxo-1,2-dihydro-pyridin-3-yl)-benzenesulfonamide The titled compound was synthesized in a similar manner as described in Example 22, Step D. MS: 393 (M+H)+.

Example 38

N-(1-Hydroxy-2-oxo-1,2-dihydro-pyridin-3-yl)-N-methyl-4-p-tolyloxy-benzenesulfonamide Compound 38

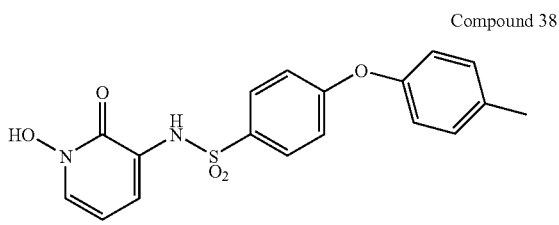

The titled compound was synthesized in a similar manner as described in Example 37 by replacing 4-chlorobiphenyl-sulfonyl chloride with 4-p-tolyloxy-benzenesulfonyl chloride in Step A. MS: 373 (M+H)+.

Example 39

N-(1-Hydroxy-2-oxo-1,2-dihydro-pyridin-3-yl)-N-methyl-4-(4-trifluoro-methoxy-phenoxy)-benzene-sulfonamide Compound 39

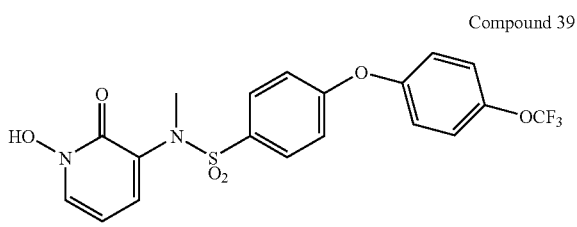

Step A. N-(2-Bromo-pyridin-3-yl)-4-fluoro-benzenesulfonamide

To a solution of 3-amino-2-bromo-pyridine (0.4 g, 2.3 mmol) in dichloromethane (4 ml) and pyridine (4 ml) was added 4-fluoro-benzenesulfonylchloride (0.45 g, 2.3 mmol) in one portion. The mixture was stirred overnight. The mixture was diluted with dichloromethane and washed with saturated NaCl solution. The organic layer was dried over sodium sulfate and concentrated. The crude product was purified through chromatography (2-5% EtOAc in dichloromethane). MS 331.8 (M+H)+

Step B. N-(2-Bromo-pyridin-3-yl)-4-fluoro-N-methyl-benzenesulfonamide

To a solution of N-(2-bromo-pyridin-3-yl)-4-fluoro-benzenesulfonamide (0.3 g, 0.9 mmol) from Step A in DMF (4 ml) was added $Cs_2CO_3$ (0.4 g, 1.3 mmol). To the mixture iodomethane (0.128 ml, 2 mmol) was added at room temperature. The mixture was stirred for 5 hours and then was diluted with EtOAc and washed with saturated NaCl solution. The organic phase was dried over sodium sulfate and concentrated. The crude was purified through Chromatography. (3-4% EtOAc in dichloromethane). MS 344.9 (M+H)+

Step C. N-(2-Bromo-pyridin-3-yl)-N-methyl-4-(4-trifluoromethoxy-phenoxy)-benzenesulfonamide To a solution of N-(2-bromo-pyridin-3-yl)-4-fluoro-N-methyl-benzenesulfonamide (0.1 g, 0.28 mmol) from Step B in dimethylacetamide (2 ml) was added $K_2CO_3$ (0.08 g, 1.0 mmol) and 4-trifluoromethoxyphenol (0.051 g, 0.28 mmol). The mixture was microwaved/heated at 130° C. (PMAX 130 on CEM Reactor) for 15 minutes. The reaction mixture was diluted EtOAc and washed with saturated NaCl and water. The organic phase was dried over sodiumsulfate and concentrated. The crude was purified through chromatography (20-50% EtOAc in hexanes) MS 502.6 (M+H)+

Step D. N-(2-Bromo-1-oxy-pyridin-3-yl)-N-methyl-4-(4-trifluoromethoxy-phenoxy)-benzenesulfonamide N-(2-Bromo-pyridin-3-yl)-N-methyl-4-(4-trifluoromethoxy-phenoxy)-benzene-sulfonamide (0.1 g, 0.19 mmol) from Step C was added to a solution of $H_2O_2$ (30% solution in water) (2 ml) and trifluoroacetic acid (3 ml). The solution was heated to 60° C. for 2 hrs. The reaction mixture was neutralized with sodium hydroxide solution to pH 7. Extracted with EtOAc and washed with water. The organic layer was dried over sodiumsulfate and concentrated. The crude was purified through chromatography (1-5% MeOH in EtOAc). MS 518.8 (M+H)+, 1038.7 (2M+H)+

Step E. N-(2-Methoxy-1-oxy-pyridin-3-yl)-N-methyl-4-(4-trifluoromethoxy-phenoxy)-benzene-sulfonamide To a solution of N-(2-bromo-1-oxy-pyridin-3-yl)-N-methyl-4-(4-trifluoromethoxy-phenoxy)-benzenesulfonamide (0.05 g, 0.09 mmol) from Step D in 4 ml MeOH was added NaOMe solution in methanol (0.5 M) (0.23 ml, 0.11 mmol). The solution was heated to reflux and stirred for 4 hours. The solution was neutralized to pH 7 by adding HCl solution (0.1N). The solution was extracted with dichloromethane. The organic layer was dried over sodium sulfate and concentrated. The crude was purified through chromatography (2-6% MeOH in EtOAc). MS 471.0 (M+H)+

Step F. N-(1-Hydroxy-2-oxo-1,2-dihydro-pyridin-3-yl)-N-methyl-4-(4-trifluoro-methoxy-phenoxy)-benzenesulfonamide To a solution of N-(2-methoxy-1-oxy-pyridin-3-yl)-N-methyl-4-(4-trifluoromethoxy-phenoxy)-benzenesulfonamide (0.05 g, 0.1 mmol) from Step E in dichloromethane (1 ml) was added 5 ml of (6N)HCl solution. The solution was heated to reflux for 2 hrs. Solvents were removed under the reduced pressure. The crude material (Compound 39) was purified through recrystallization in ethylacetate/hexane. MS 457.0 (M+H)+, 479.0 (M+Na)+

Example 40

4'-Chloro-biphenyl-4-sulfonic acid (1-hydroxy-2-oxo-1,2-dihydro-pyridin-3-yl)-amide

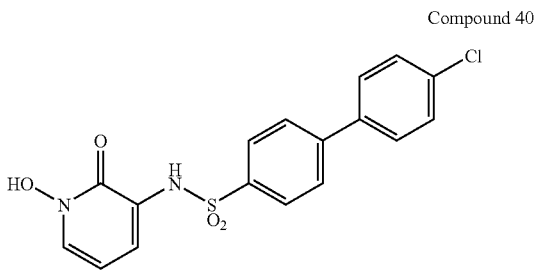

Compound 40

Step A. (2-Methoxy-pyridin-3-yl)-carbamic acid benzyl ester

To a solution of 3-amino-2-methoxypyridine (3.93 g, 31.7 mmol) in THF/$H_2O$ (1:1) (120 mL) was added $Cs_2CO_3$ (12.4 g, 38.0 mmol) and benzylchloroformate (5.33 mL, 37.9 mmol) and the reaction stirred at room temperature for 5 hours. The mixture was diluted with water, extracted with EtOAc, dried over $MgSO_4$, filtered, and the solvent was removed. The crude product was purified by chromatography (silica gel, 25% EtOAc/hexanes). MS 259 (M+H)$^+$.

Step B. (2-Methoxy-1-oxy-pyridin-3-yl)-carbamic acid benzyl ester

The (2-methoxy-pyridin-3-yl)-carbamic acid benzyl ester (6.26 g, 24.2 mmol) from Step A was dissolved in dry $CH_2Cl_2$ (180 mL) and urea hydrogen peroxide complex (6.28 g, 67.9 mmol) was added to the solution, which was cooled to 0 C. TFAA (9.1 mL, 65.5 mmol) was then slowly added to the reaction mixture (the reaction was exothermic). The reaction was allowed to warm to room temperature and stirred overnight. The reaction was quenched with an aqueous solution of $Na_2S_2O_3$ and stirred for 15 min to destroy any residual peroxides. The mixture was then brought up to the usual work. The resulting residual was purified by chromatography (silica gel, 8% MeOH/EtOAc). MS 275 (M+H)$^+$.

Step C. (1-Hydroxy-2-oxo-1,2-dihydro-pyridin-3-yl)-carbamic acid benzyl ester A solution of (2-methoxy-1-oxy-pyridin-3-yl)-carbamic acid benzyl ester (1.7 g, 6.2 mmol) from Step B in MeOH (15 mL) was treated with 10 mL of HCl solution (2N) and the resulting solution was heated at reflux for 30 min. The reaction was cooled to room temperature and most solvent was removed. The product was filtered off as a white solid and washed with water. MS 261 (M+H)$^+$.

Step D. (1-Benzyloxy-2-oxo-1,2-dihydro-pyridin-3-yl)-carbamic acid benzyl ester A suspension of (1-hydroxy-2-oxo-1,2-dihydro-pyridin-3-yl)-carbamic acid benzyl ester (1.5 g, 5.76 mmol) from Step C and $K_2CO_3$ (1.59 g, 11.5 mmol) in dry DMF (15 mL) was added benzyl bromide (0.82 mL, 6.91 mmol). The reaction mixture was stirred at room temperature for 2 h and diluted with water. The usual work-up (EtOAc extraction) and purification by chromatography (silica gel, 25% EtOAc/hexanes) gave the desired product. MS 351 (M+H)$^+$.

Step E. 3-Amino-1-benzyloxy-1H-pyridin-2-one hydrogen bromide salt

To a solution of (1-benzyloxy-2-oxo-1,2-dihydro-pyridin-3-yl)-carbamic acid benzyl ester (1.8 g, 5.14 mmol) from Step D in $CH_2Cl_2$ (12 mL) was added HBr (33% in AcOH, 8 mL) at 0° C. under $N_2$. The reaction solution was stirred at 0 C for 4 hours and then $CDCl_3$/hexanes (1:2) was added. The sticky gum was crunched out. The solvents were decanted and additional $CDCl_3$/hexanes (1:3) were added to the gummy residue. Stirring resulted solid formed Filtration and washed with hexanes/$Et_2O$ afforded HBr salt. MS 217 (M+H)$^+$.

Step F. 4'-Chloro-biphenyl-4-sulfonic acid (1-benzyloxy-2-oxo-1,2-dihydro-pyridin-3-yl)-amide The titled compound was prepared from 3-amino-1-benzyloxy-1H-pyridin-2-one hydrogen bromide salt from Step E and 4'-chloro-biphenyl-4-sulfonyl chloride according to the procedure described in Example 32 Step A. MS 467 (M+H)$^+$.

Step G. 4'-Chloro-biphenyl-4-sulfonic acid (1-hydroxy-2-oxo-1,2-dihydro-pyridin-3-yl)-amide A solution of 4'-chloro-biphenyl-4-sulfonic acid (1-benzyloxy-2-oxo-1,2-dihydro-pyridin-3-yl)-amide (40 mg, 0.086 mmol) in $MeSO_3H$ (0.7 mL) was stirred at room temperature for 5 hours. Ice water was added to the reaction and the resulting solid was filtered and washed with water. The solid obtained (Compound 40) was washed with $Et_2O$/hexanes twice. MS 377 (M+H)$^+$.

Example 41

3-(4'-Bromo-biphenyl-4-yloxymethyl)-1-hydroxy-1H-pyridin-2-one

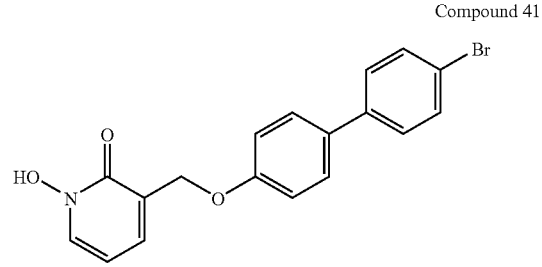

Compound 41

Step A. (2-Methoxy-pyridin-3-yl)-methanol

To a solution of $NaBH_4$ (0.075 g, 2.04 mmol) in absolute EtOH (10 mL) was dropwise added a solution of 2-methoxy-pyridine-3-carbaldehyde (0.98 g, 7.15 mmol) in EtOH (2 mL) at −40° C. under $N_2$. The reaction mixture was stirred at −40° C. for 45 min and then carefully quenched with brine. After warmed up to room temperature, the reaction solvent was removed and then diluted with EtOAc and water. The aqueous layer was extracted with EtOAc (×2) and the combined organics were washed with water, brine and dried over anhydrous $Na_2SO_4$. The mixture was filtered through Celite-silica gel.

The concentration under the reduced pressure provided the product, which was carried to the next step without further purification. ¹H NMR (300 MHz, CDCl₃) 8.13 (m, 1H), 7.63 (m, 1H), 6.90 (m, 1H), 4.67 (s, 2H), 4.02 (s, 3H).

Step B. 3-(4'-Bromo-biphenyl-4-yloxymethyl)-2-methoxy-pyridine

To a mixture of PPh₃ (0.53 g, 2.03 mmol) and DIAD (0.4 mL, 2.03 mmol) in dry THF (3 mL) at 0° C. was added a mixture of (2-methoxy-pyridin-3-yl)-methanol (0.18 g, 1.27 mmol) from Step A and 4'-bromo-biphenyl-4-ol (0.33 g, 1.33 mmol) in dry THF (2 mL). After 1 hr, the reaction was warmed to room temperature and monitored by TLC. After the reaction was completed (~4 h), the reaction mixture was concentrated under vacuo and then diluted with EtOAc. The precipitates were filtered. The filtrate was brought to the usual work-up. The resulting crude product was purified by chromatography (silica gel, 15% EtOAc/hexanes) to give the titled compound. MS: 370, 372 (M+H)⁺.

Step C. 3-(4'-Bromo-biphenyl-4-yloxymethyl)-2-methoxy-pyridine 1-oxide

A mixture of 3-(4'-bromo-biphenyl-4-yloxymethyl)-2-methoxy-pyridine (0.19 g, 0.51 mmol) from Step B and mCPBA (77% max., 0.25 g, 1.13 mmol) in dichloromethane (5 mL) was stirred at room temperature for 3 days. The reaction was diluted with dichloromethane and washed with aqueous Na₂SO₃ solution, 1N NaOH solution, water and brine. The organic layer was dried over anhydrous K₂CO₃ and filtered through Celite. The filtrate was concentrated under vacuo and the residue was purified by chromatography (silica gel, 10% MeOH/EtOAc) to give the desired product. MS: 386, 388 (M+H)⁺.

Step D. 3-(4'-Bromo-biphenyl-4-yloxymethyl)-1-hydroxy-1H-pyridin-2-one

A solution of 3-(4'-bromo-biphenyl-4-yloxymethyl)-2-methoxy-pyridine 1-oxide (0.045 g, 0.12 mmol) from Step C in MeOH (1 mL) was treated with 2N HCl (1.5 mL) at reflux for 1 h. The reaction mixture was concentrated under the reduced pressure and the resulting material (Compound 41) was washed with water and Et₂O/hexanes (1:5) to give the titled compound. MS: 372, 374 (M+H)⁺.

Example 42

N-(1-Hydroxy-2-oxo-1,2-dihydro-pyridin-3-ylmethyl)-N-(4-p-tolyloxy-phenyl)-methanesulfonamide

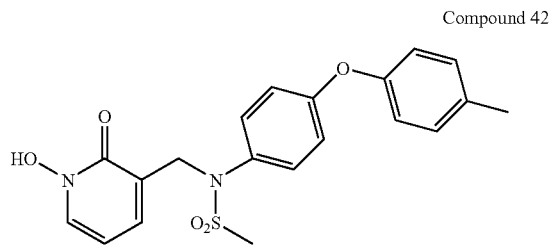

Compound 42

Step A. 3-Chloromethyl-2-methoxy-pyridine

To a solution of (2-methoxy-pyridin-3-yl)-methanol (0.38 g, 2.74 mmol) from example 42 step A and triethylamine (0.5 mL, 3.56 mmol) in 6 mL of CH₂Cl₂ was added methanesulfonyl chloride (0.26 mL, 3.29 mmol) at 0° C. After 1 hr, the reaction was warmed to room temperature and stirred overnight. The reaction mixture was brought to the usual work-up to give the crude product, which was purified by chromatography (silica gel, 25% EtOAc/hexanes). ¹H NMR (300 MHz, CDCl₃) 8.15 (m, 1H), 7.67 (m, 1H), 6.91 (m, 1H), 4.60 (s, 2H), 4.02 (s, 3H).

Step B. N-(4-p-Tolyloxy-phenyl)-methanesulfonamide

To a solution of 4-p-tolyloxy-phenylamine (0.87 g, 4.38 mmol) and pyridine (0.52 mL, 6.53 mmol) in dried CH₂Cl₂ (10 mL) under N₂ at 0° C. was added methanesulfonyl chloride (0.41 mL, 5.26 mmol) dropwise. The mixture was stirred at 0° C. for 1 h and was then poured into CH₂Cl₂/H₂O (10 mL/10 mL). The organic layer was washed with 2N HCl (aq) (3 mL), H₂O, brine, dried (Na₂SO₄), and filtered through Celite. After removal of solvent, the crude product was purified by chromatography (silica gel, 45% EtOAc/hexanes) to give the titled compound. MS (EI) 278 (M+H)⁺.

Step C. N-(2-Methoxy-pyridin-3-ylmethyl)-N-(4-p-tolyloxy-phenyl)-methane-sulfonamide A mixture of 3-chloromethyl-2-methoxy-pyridine (0.2 g, 1.29 mmol) from Step A, N-(4-p-tolyloxy-phenyl)-methane-sulfonamide (0.38 g, 1.35 mmol) from Step B and K₂CO₃ (0.44 g, 3.22 mmol) in dry DMF (5 mL) was heated at 70° C. overnight. The reaction was then diluted with EtOAc/H₂O. The aqueous layer was extracted with EtOAc (×2) and the combined organics were brought to the usual work-up. The resulting crude material was purified by chromatography (silica gel, 40% EtOAc/hexanes) to give the desired product. MS (EI) 399 (M+H)⁺.

Step D. N-(2-Methoxy-1-oxy-pyridin-3-ylmethyl)-N-(4-p-tolyloxy-phenyl)-methane-sulfonamide The titled compound was synthesized from N-(2-methoxy-pyridin-3-ylmethyl)-N-(4-p-tolyloxy-phenyl)-methane-sulfonamide from Step C in a similar manner as described in Example 41, Step C. MS (EI) 415 (M+H)⁺.

Step E. N-(1-Hydroxy-2-oxo-1,2-dihydro-pyridin-3-ylmethyl)-N-(4-p-tolyloxy-phenyl)-methanesulfonamide The titled compound was synthesized from N-(2-methoxy-1-oxy-pyridin-3-ylmethyl)-N-(4-p-tolyloxy-phenyl)-methane-sulfonamide from Step D in a similar manner as described in Example 22, Step D. MS (EI) 401 (M+H)⁺.

Example 43

N-(1-Hydroxy-2-oxo-1,2-dihydro-pyridin-3-ylmethyl)-N-[4-(4-trifluoromethyl-phenoxy)-phenyl]-methanesulfonamide

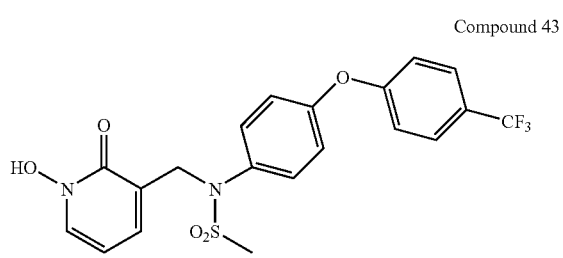

Compound 43

The titled compound was synthesized in a similar manner as described in Example 42 by replacing 4-p-tolyloxy-phenylamine with 4-(4-trifluoromethyl-phenoxy)-phenylamine in Step B. MS (EI) 455 (M+H)⁺.

Example 44

N-[4-(4-Chloro-phenoxy)-phenyl]-N-(1-hydroxy-2-oxo-1,2-dihydro-pyridin-3-ylmethyl)-methane-sulfonamide Compound 44

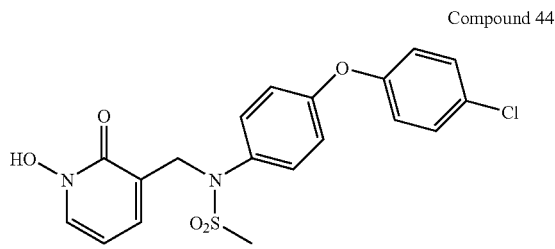

The titled compound was synthesized in a similar manner as described in Example 42 by replacing 4-p-tolyloxy-phenylamine with 4-(4-chloro-phenoxy)-phenylamine in Step B. MS (EI) 421 (M+H)⁺.

Example 45

N-(4-Butyl-phenyl)-N-(1-hydroxy-2-oxo-1,2-dihydro-pyridin-3-ylmethyl)-methane-sulfonamide Compound 45

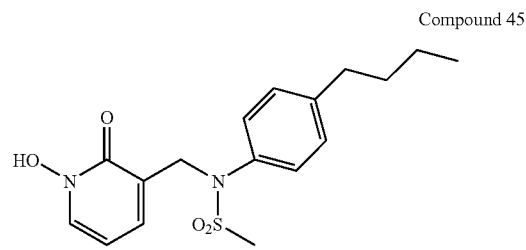

The titled compound was synthesized in a similar manner as described in Example 42 by replacing 4-p-tolyloxy-phenylamine with 4-butyl-phenylamine in Step B. MS (EI) 351 (M+H)⁺.

Example 46

N-(4-Butoxy-phenyl)-N-(1-hydroxy-2-oxo-1,2-dihydro-pyridin-3-ylmethyl)-methanesulfonamide Compound 46

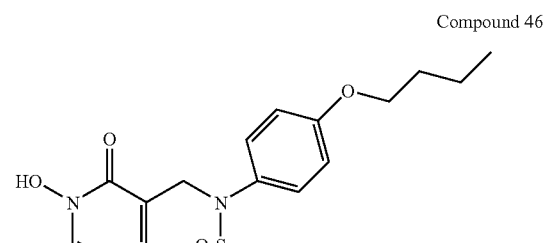

The titled compound was synthesized in a similar manner as described in Example 42 by replacing 4-p-tolyloxy-phenylamine with 4-butoxy-phenylamine in Step B. MS (EI) 367 (M+H)⁺.

Example 47

N-(1-Hydroxy-2-thioxo-1,2-dihydro-pyridin-3-ylmethyl)-N-(4-p-tolyloxy-phenyl)-methanesulfonamide Compound 47

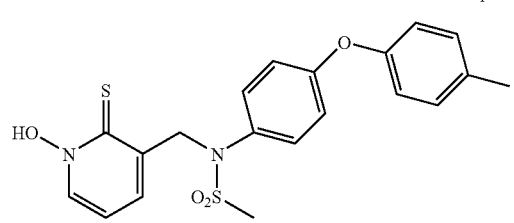

Step A. (2-Bromo-pyridin-3-yl)-methanol

The titled compound was synthesized from 2-bromo-pyridine-3-carbaldehyde in a similar manner as described in Example 41, Step A. ¹H NMR (300 MHz, CDCl₃) 8.30 (m, 1H), 7.84 (m, 1H), 7.32 (m, 1H), 4.77 (s, 2H).

Step B. 2-Bromo-3-chloromethyl-pyridine

The titled compound was synthesized in a similar manner as described in Example 42 Step A. ¹H NMR (300 MHz, CDCl₃) 8.32 (m, 1H), 7.84 (m, 1H), 7.32 (m, 1H), 4.68 (s, 2H).

Step C. N-(2-Bromo-1-oxy-pyridin-3-ylmethyl)-N-(4-p-tolyloxy-phenyl)-methane-sulfonamide The titled compound was synthesized from 2-bromo-3-chloromethyl-pyridine from Step B and N-(4-p-tolyloxy-phenyl)-methanesulfonamide from Example 42 step B in a similar manner as described in Example 42, Step C and Step D. MS (EI) 463, 465 (M+H)⁺.

Step D. N-(1-Hydroxy-2-thioxo-1,2-dihydro-pyridin-3-ylmethyl)-N-(4-p-tolyloxy-phenyl)-methane-sulfonamide To a solution of N-(2-bromo-1-oxy-pyridin-3-ylmethyl)-N-(4-p-tolyloxy-phenyl)-methane-sulfonamide (0.1 g, 0.22 mmol) from Step C in H₂O/DMSO (2 mL/1 mL) was added NaHS hydrate (0.048 g, 0.86 mmol). The reaction solution was heated at 100° C. for 1.5 h and then acidified by 1N aqueous HCl solution. The resulting mixture was extracted with EtOAc. The organic portion was brought to the usual work-up to provide the crude material, which was purified by chromatography (silica gel, 85% EtOAc/hexanes) to give the desired product. MS (EI) 417 (M+H)⁺.

Example 48

N-(1-Hydroxy-4-methyl-2-oxo-1,2-dihydro-pyridin-3-ylmethyl)-N-(4-p-tolyloxy-phenyl)-methanesulfonamide Compound 48

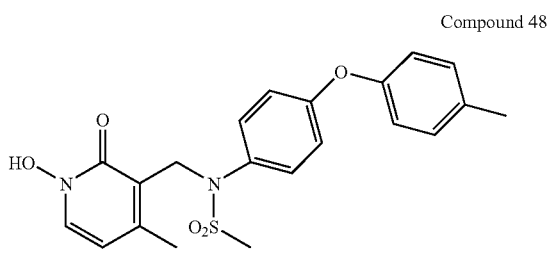

The titled compound was synthesized in a similar manner as described in Example 41, step A, by replacing 2-methoxy-pyridine-3-carbaldehyde with 2-methoxy-4-methyl-pyridine-3-carbaldehyde, and Example 42. MS (EI) 415 (M+H)$^+$.

Example 49

N-(5-Bromo-1-hydroxy-2-oxo-1,2-dihydro-pyridin-3-ylmethyl)-N-(4-p-tolyloxy-phenyl)-methanesulfonamide Compound 49

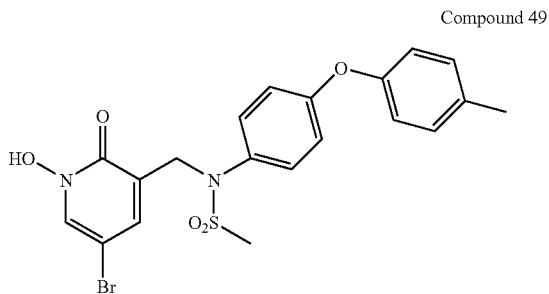

Step A. (5-Bromo-2-methoxy-pyridin-3-ylmethyl)-(4-p-tolyloxy-phenyl)-amine

A solution of 5-bromo-2-methoxy-pyridine-3-carbaldehyde (0.87 g, 4.03 mmol) in dry MeOH (15 mL) was treated with 4-p-tolyloxy-phenylamine (0.88 g, 4.43 mmol) and reflux for 2.5 h. The solution was cooled to 0° C. and treated slowly with NaBH$_4$ (0.38 g, 10.1 mmol). The reaction stirred at room temperature overnight. Additional NaBH$_4$ (0.38 g, 10.1 mmol) was added and the reaction was continued stirring for additional 6 h. The solvent was removed and the residue was partitioned between CH$_2$Cl$_2$ (20 mL) and water (10 mL). The organic portion was brought to the usual work-up to give a crude material. The product was yielded after chromatography purification (silica gel, 25% EtOAc/hexanes). MS (EI) 399, 401 (M+H)$^+$.

Step B. N-(5-Bromo-2-methoxy-pyridin-3-ylmethyl)-N-(4-p-tolyloxy-phenyl)-methanesulfonamide To a solution of (5-bromo-2-methoxy-pyridin-3-ylmethyl)-(4-p-tolyloxy-phenyl)-amine (0.73 g, 1.82 mmol) from Step A in CH$_2$Cl$_2$/pyridine (6 mL/3 mL) was dropwise added methylsulfonyl chloride (0.17 mL, 2.2 mmol) at 0° C. The resulting mixture was warmed to room temperature and stirred overnight. The reaction was then diluted with CH$_2$Cl$_2$ and washed with aqueous HCl (3N) to remove pyridine. The organic layer was then brought to the usual work-up. The crude product was purified by chromatography (silica gel, 30% EtOAc/hexanes). MS (EI) 477, 479 (M+H)$^+$.

Step C. N-(5-Bromo-2-methoxy-1-oxy-pyridin-3-ylmethyl)-N-(4-p-tolyloxy-phenyl)-methanesulfonamide The titled compound was synthesized from N-(5-bromo-2-methoxy-pyridin-3-ylmethyl)-N-(4-p-tolyloxy-phenyl)-methanesulfonamide from Step B in a similar manner as described in Example 37 Step B. MS (EI) 493, 495 (M+H)$^+$.

Step D. N-(5-Bromo-1-hydroxy-2-oxo-1,2-dihydropyridin-3-ylmethyl)-N-(4-p-tolyloxy-phenyl)-methanesulfonamide The titled compound was synthesized from N-(5-bromo-2-methoxy-1-oxy-pyridin-3-ylmethyl)-N-(4-p-tolyloxy-phenyl)-methanesulfonamide from Step C in a similar manner as described in Example 22 Step D. MS (EI) 479, 481 (M+H)$^+$.

Example 50

N-[1-(1-Hydroxy-2-oxo-1,2-dihydro-pyridin-3-yl)-ethyl]-N-(4-p-tolyloxy-phenyl)-methanesulfonamide Compound 50

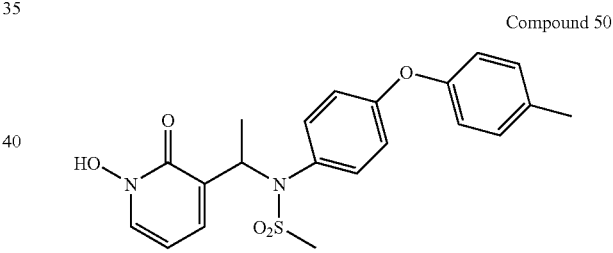

Step A. 1-(2-Bromo-pyridin-3-yl)-ethanol

To a solution of 2-bromo-pyridine-3-carbaldehyde (0.14 g, 0.75 mmol) in dry THF (10 mL) was dropwise added methylmagnesium bromide (1.4 M, 0.59 mL, 0.82 mmol) at −20° C. The reaction was allowed to warm to 0° C. for 20 min and then quenched with aqueous ammonium chloride solution. The usual work up gave a crude material, which was purified by chromatography (silica gel, 40% EtOAc/hexanes). $^1$H NMR (300 MHz, CDCl$_3$) 8.30 (m, 1H), 7.96 (m, 1H), 7.34 (m, 1H), 5.21 (q, 1H), 1.54 (d, 3H).

Step B. N-[1-(2-Methoxy-pyridin-3-yl)-ethyl]-N-(4-p-tolyloxy-phenyl)-methane-sulfonamide To a mixture of PPh$_3$ (0.26 g, 1.0 mmol) and DIAD (0.2 mL, 1.0 mmol) in dry THF (3 mL) at 0 C was added a solution of 1-(2-bromo-pyridin-3-yl)-ethanol (0.14 g, 0.67 mmol) from Step A and N-(4-p-tolyloxy-phenyl)-methanesulfonamide (0.19 g, 0.7 mmol) from Example 42 step B in dry THF (2 mL). After 1 h, the reaction was warmed to room temperature and stirred for 3 h. The reaction was then concentrated under the reduced pressure. The residue was diluted with EtOAc and the precipitates were filtered. The filtrate was brought to the usual work-up. The crude material was purified by chromatography (silica gel, 30% EtOAc/hexanes) to give the desired product. MS (EI) 413 (M+H)+.

Step C. N-[1-(1-Hydroxy-2-oxo-1,2-dihydro-pyridin-3-yl)-ethyl]-N-(4-p-tolyloxy-phenyl)-methanesulfonamide The titled compound was synthesized from N-[1-(2-methoxy-pyridin-3-yl)-ethyl]-N-(4-p-tolyloxy-phenyl)-methanesulfonamide from Step B in a similar manner as described as Example 41, Step C and step D. MS (EI) 415 (M+H)+.

Example 51

N-(1-Hydroxy-5-methyl-2-oxo-1,2-dihydro-pyridin-3-ylmethyl)-N-(4-p-tolyloxy-phenyl)-methanesulfonamide Compound 51

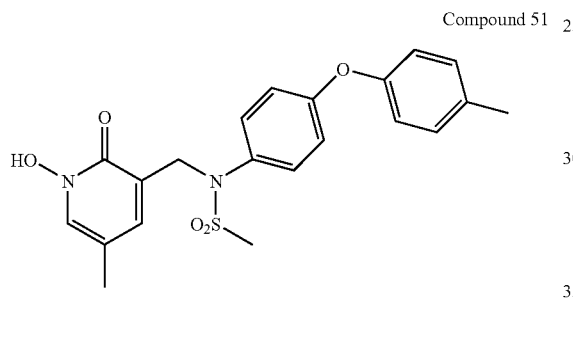

Step A. (2-Bromo-5-methyl-pyridin-3-yl)-methanol

A solution of 2-bromo-5-methyl-nicotinic acid ethyl ester (0.4 g, 1.63 mmol) (synthesized according to Ponticello's procedure J. Org. Chem., 1978, 43, 2529-2535) in Et$_2$O (10 mL) was dropwise added LiAlH$_4$ (1.0 M in THF, 1.79 mL, 1.79 mmol) at −78° C. After the addition was completed, the suspension was stirred at −78 C for 1 h. EtOAc was carefully added at −78° C. and then water was dropwise added. The organic portion was brought to the usual work-up to give the product without further purification. $^1$H NMR (300 MHz, CDCl$_3$) 8.13 (s, 1H), 7.68 (s, 1H), 4.73 (s, 2H), 2.33 (s, 3H).

Step B. N-(2-Bromo-5-methyl-1-oxy-pyridin-3-ylmethyl)-N-(4-p-tolyloxy-phenyl)-methanesulfonamide The titled compound was synthesized from (2-bromo-5-methyl-pyridin-3-yl)-methanol from Step A and N-(4-p-tolyloxy-phenyl)-methanesulfonamide from Example 42 step B, according to the procedures described in Example 41 Step B and Step C. MS (EI) 477, 479 (M+H)+.

Step C. N-(2-Methoxy-5-methyl-1-oxy-pyridin-3-ylmethyl)-N-(4-p-tolyloxy-phenyl)-methanesulfonamide A solution of N-(2-bromo-5-methyl-1-oxy-pyridin-3-ylmethyl)-N-(4-p-tolyloxy-phenyl)-methanesulfonamide (0.52 g, 1.09 mmol) from Step B in anhydrous MeOH (10 mL) was treated with NaOMe (25 wt. % in MeOH, 0.28 mL, 1.22 mmol) and the reaction was heated to reflux for 3.5 h. The solvent was removed and the residue was diluted with CH$_2$Cl$_2$ and water. The organic portion was brought to the usual work-up. The crude material was purified by chromatography (silica gel, 6% MeOH/EtOAc) to give the desired product. MS (EI) 429 (M+H)+.

Step D. N-(1-Hydroxy-5-methyl-2-oxo-1,2-dihydro-pyridin-3-ylmethyl)-N-(4-p-tolyloxy-phenyl)-methanesulfonamide The titled compound was synthesized from N-(2-methoxy-5-methyl-1-oxy-pyridin-3-ylmethyl)-N-(4-p-tolyloxy-phenyl)-methanesulfonamide from Step C in a similar manner as described in Example 22, Step D. MS (EI) 415 (M+H)+.

Example 52

N-(1-Hydroxy-2-oxo-5-phenyl-1,2-dihydro-pyridin-3-ylmethyl)-N-(4-p-tolyloxy-phenyl)-methanesulfonamide Compound 52

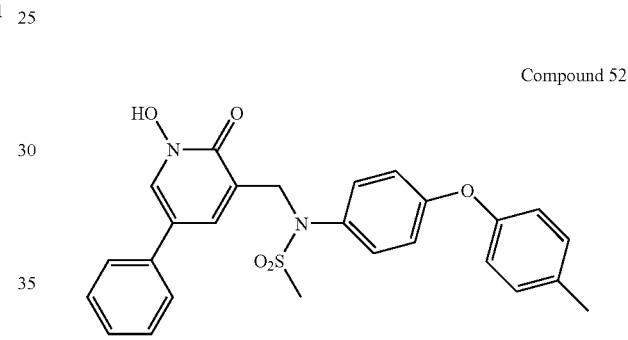

Step A. N-(2-Methoxy-5-phenyl-pyridin-3-ylmethyl)-N-(4-p-tolyloxy-phenyl)-methanesulfonamide A solution of N-(5-bromo-2-methoxy-pyridin-3-ylmethyl)-N-(4-p-tolyloxy-phenyl)-methanesulfonamide (0.16 g, 0.33 mmol) from Example 49 Step A and phenyl boronic acid (0.059 g, 0.49 mmol) in dioxane/H$_2$O (2 mL/0.5 mL) was treated with Na$_2$CO$_3$ (0.11 g, 1.0 mmol) and PdCl$_2$dppf.CH$_2$Cl$_2$ complex (23.8 mg, 0.033 mmol). The resulting mixture was heated at 100° C. overnight. The reaction mixture was brought to the usual work-up and the crude product was purified by chromatography (silica gel, 35% EtOAc/hexanes) to give the desired product. MS (EI) 475 (M+H)+.

Step B. N-(1-Hydroxy-2-oxo-5-phenyl-1,2-dihydro-pyridin-3-ylmethyl)-N-(4-p-tolyloxy-phenyl)-methanesulfonamide The titled compound was synthesized from N-(2-methoxy-5-phenyl-pyridin-3-ylmethyl)-N-(4-p-tolyloxy-phenyl)-methanesulfonamide from Step A in a similar manner as described in Example 41, Step C and Step D. MS (EI) 477 (M+H)+.

Example 53

N-(1-Hydroxy-2-oxo-1,2-dihydro-pyridin-3-ylmethyl)-N-[4-(4-methoxy-phenoxy)-phenyl]-methanesulfonamide

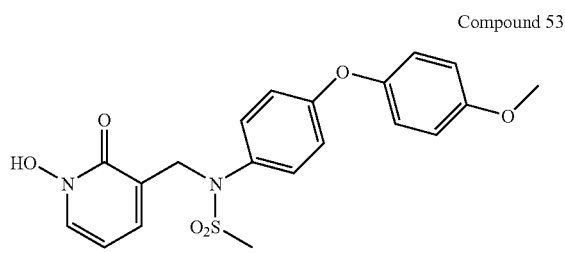

Compound 53

Step A. N-(4-Iodo-phenyl)-methanesulfonamide

The titled compound was synthesized from 4-iodo-phenylamine according to the procedure described in Example 42 Step B. MS (EI) 297 (M+H)$^+$.

Step B. N-[4-(4-Methoxy-phenoxy)-phenyl]-methanesulfonamide

A mixture of N-(4-iodo-phenyl)-methanesulfonamide (0.45 g, 1.52 mmol) from Step A, 4-methoxyphenol (0.28 g, 2.28 mmol), $Cs_2CO_3$ (0.99 g, 3.04 mmol), N,N-dimethylglycine HCl salt (31.8 mg, 0.23 mmol) and CuI (14.5 mg, 0.076 mmol) in dioxane (4 mL) under $N_2$ was heated to 100 C overnight. The reaction was diluted with EtOAc and brought to the usual work-up. The residue was purified by chromatography (silica gel, 30% EtOAc/hexanes) to give the desired product. MS (EI) 294 (M+H)$^+$.

Step C. N-(1-Hydroxy-2-oxo-1,2-dihydro-pyridin-3-ylmethyl)-N-[4-(4-methoxy-phenoxy)-phenyl]-methanesulfonamide The titled compound was synthesized from N-[4-(4-methoxy-phenoxy)-phenyl]-methanesulfonamide from Step B and 3-chloromethyl-2-methoxy-pyridine from Example 42 Step A in a similar manner as described in Example 42 Step C, Step D and Step E. MS (EI) 417 (M+H)$^+$.

Example 54

N-(1-Hydroxy-2-oxo-1,2-dihydro-pyridin-3-ylmethyl)-N-[4-(4-trifluoro-methoxy-phenoxy)-phenyl]-methanesulfonamide Compound 54

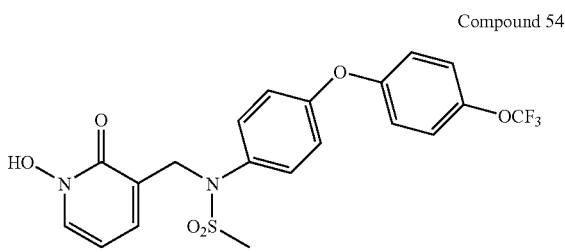

The titled compound was synthesized from 3-chloromethyl-2-methoxy-pyridine from Example 42, Step A and N-[4-(4-trifluoromethoxy-phenoxy)-phenyl]-methanesulfonamide (synthesized according to the procedure shown below) in a similar manner as described in example 54. MS (EI) 471 (M+H)$^+$.

N-[4-(4-Trifluoromethoxy-phenoxy)-phenyl]-methanesulfonamide

To a solution of 4-trifluoromethoxy-phenol (0.7 mL, 5.4 mmol) in NMP (6 mL) was added $Cs_2CO_3$ (1.76 g, 5.4 mmol). The slurry was degassed for 2 min and added N-(4-iodo-phenyl)-methanesulfonamide (0.80 g, 2.7 mmol) from Example 33, Step A, 2,2,6,6-tetramethylheptane-3,5-dione (0.056 mL, 0.27 mmol) and CuCl (0.134 g, 1.35 mmol) subsequently. The reaction mixture was heated to 110° C. under $N_2$ overnight. The reaction was brought to the usual work-up and the crude material was purified by chromatography (20% EtOAc/hexanes). MS (EI) 348 (M+H)$^+$.

Example 55

N-(1-Hydroxy-2-oxo-1,2-dihydro-pyridin-3-ylmethyl)-N-(4-p-tolylethynyl-phenyl)-methanesulfonamide

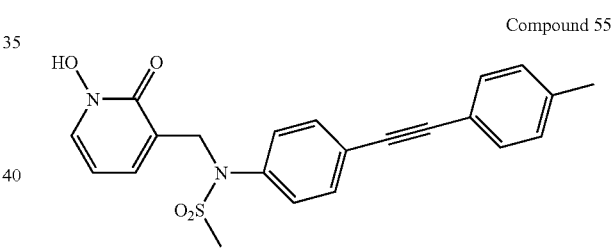

Compound 55

The titled compound was synthesized from 2-bromo-3-chloromethyl-pyridine from Example 47, Step B and N-(4-p-tolylethynyl-phenyl)-methanesulfonamide (synthesized according to the procedure shown below) in a similar manner as described in Example 51. MS (EI) 409 (M+H)$^+$.

N-(4-p-Tolylethynyl-phenyl)-methanesulfonamide

A mixture of N-(4-iodo-phenyl)-methanesulfonamide (0.46 g, 1.54 mmol), Pd(PPh$_3$)$_2$Cl$_2$ (54 mg, 0.077 mmol) and CuI (14.7 mg, 0.077 mmol) in TEA/THF (10 mL/3 mL) was treated with 1-ethynyl-4-methyl-benzene (0.29 mL, 2.32 mmol). The reaction mixture was degassed and stirred at room temperature for 30 min. The solvent was removed under the reduced pressure. The residue was diluted with EtOAc and water. After the usual work-up, the obtained crude material was purified by chromatography (35% EtOAc/hexanes) to give the desired product. MS (EI) 286 (M+H)$^+$.

Example 56

N-(1-Hydroxy-2-thioxo-1,2-dihydro-pyridin-3-ylmethyl)-N-(4-p-tolylethynyl-phenyl)-methanesulfonamide

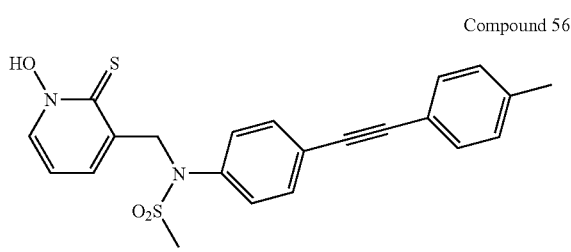

Compound 56

The titled compound was synthesized from 2-bromo-3-chloromethyl-pyridine from Example 47, Step B and N-(4-p-tolylethynyl-phenyl)-methanesulfonamide from Example 55 in a similar manner as described in Example 47. MS (EI) 425 (M+H)$^+$.

Example 57

(R)-4-(4-Chloro-phenoxy)-N-(1-hydroxy-2-oxo-piperidin-3-yl)-benzene-sulfonamide

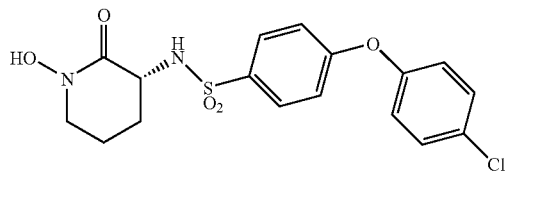

Compound 57 step A. (R)—N-(1-Benzyloxy-2-oxo-piperidin-3-yl)-4-(4-chloro-phenoxy)-benzene-sulfonamide To a suspension of (R)-3-amino-1-benzyloxy-piperidin-2-one hydrogen bromide salt (0.086 g, 0.29 mmol) (synthesized according to Miller's procedure *J. Org. Chem.* 2002, 67, 4759) and 4-(4-chloro-phenoxy)-benzenesulfonyl chloride (0.095 g, 0.31 mmol) in dry CH$_2$Cl$_2$ (3 mL) was treated with TEA (0.12 mL, 0.86 mmol) under N$_2$. The reaction mixture was stirred at room temperature for 6 h and diluted with CH$_2$Cl$_2$ and water. After the usual work-up, the crude material was purified by chromatography (silica gel, 35% EtOAc/hexanes) to give the desired product, (R)—N-(1-Benzyloxy-2-oxo-piperidin-3-yl)-4-(4-chloro-phenoxy)-benzene-sulfonamide. MS (EI) 487 (M+H)$^+$.

step B. Compound 57

A solution of (R)—N-(1-benzyloxy-2-oxo-piperidin-3-yl)-4-(4-chloro-phenoxy)-benzenesulfonamide (0.1 g) in step A in MeSO$_3$H (1.5 mL) was stirred at room temperature under N$_2$ for 16 h. The reaction was quenched with ice-water and the precipitate was filtered. The white solid was washed with water, Et$_2$O/hexanes (1:5) to give the titled compound. MS (EI) 397 (M+H)$^+$.

Example 58

(R)—N-(1-Hydroxy-2-oxo-piperidin-3-yl)-4-(4-trifluoromethyl-phenoxy)-benzenesulfonamide

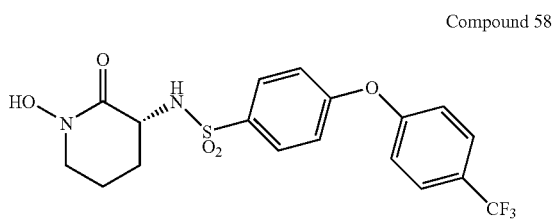

Compound 58

The titled compound was synthesized in a similar manner as described in Example 57 by replacing 4-(4-chloro-phenoxy)-benzenesulfonyl chloride with 4-(4-trifluoromethyl-phenoxy)-benzenesulfonyl chloride in Example 57. MS (EI) 431 (M+H)$^+$.

Example 59

5-Bromo-thiophene-2-sulfonic acid (1-hydroxy-2-oxo-1,2-dihydro-pyridin-3-yl)-methyl-amide

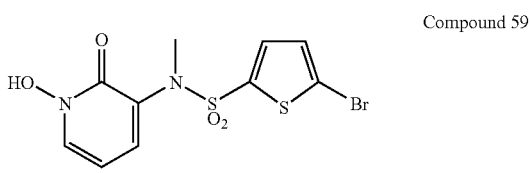

Compound 59

The titled compound was synthesized in a similar manner as described in Example 22 by replacing 4-phenoxy-benzenesulfonyl chloride with 5-bromo-2-thiophenesulfonyl chloride in Step A, and replacing benzylbromide with methyl iodide in Step B. MS: 365, 367 (M+H)$^+$.

Example 60

3-Hydroxy-1-(toluene-4-sulfonylmethyl)-1H-pyridin-2-one

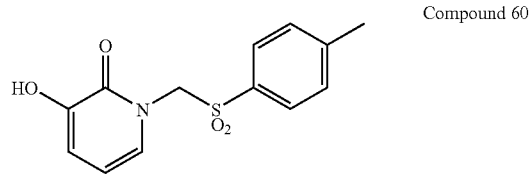

Compound 60

Step A. 3-Benzyloxy-1H-pyridin-2-one

To a mixture of NaOH (4.0 g, 100 mmol) in MeOH (120 mL) was added portion-wise 2,3-dihydroxypyridone (10 g, 90 mmol). The mixture was stirred for 15 min and then benzyl bromide (10.6 mL, 90 mmol) was dropwise added to the reaction mixture. The resulting solution was stirred at room temperature for 30 min and then heated at 40° C. for 1.5 h. After evaporation of the solvent, the residue was diluted with water and extracted with $CH_2Cl_2$ (×3). The combined organic extracts were dried over $MgSO_4$, filtered through Celite and concentrated in vacuo. Recrystallization in ethanol affords the titled compound. MS (EI) 202 (M+H)+.

Step B. 3-Benzyloxy-1-(toluene-4-sulfonylmethyl)-1H-pyridin-2-one

To a suspension of 3-benzyloxy-1H-pyridin-2-one (0.22 g, 1.1 mmol) from step A and $Cs_2CO_3$ (0.72 g, 2.2 mmol) in dry DMF (5 mL) was added 1-chloromethanesulfonyl-4-methyl-benzene (0.31 g, 1.54 mmol). The reaction mixture was heated at 95° C. overnight and then additional 1-chloromethanesulfonyl-4-methyl-benzene (0.22 g, 1.1 mmol) was added. The reaction mixture was stirred for another 18 h. After the usual work-up, the crude material was purified by chromatography (silica gel, 40% EtOAc/hexanes) to give the product. MS (EI) 370 (M+H)+.

Step C. 3-Hydroxy-1-(toluene-4-sulfonylmethyl)-1H-pyridin-2-one

A solution of 3-benzyloxy-1-(toluene-4-sulfonylmethyl)-1H-pyridin-2-one (50 mg) from Step B in $MeSO_3H$ (1.5 mL) was stirred at room temperature for 20 min and then quenched with ice water. The solid was filtered off and washed with water. The crude product was re-dissolved in hot MeOH (1 mL) and removed un-dissolved brownish solid. The filtrate was concentrated in vacuo to give the titled compound. MS (EI) 280 (M+H)+.

Example 61

3-Hydroxy-1-(4-p-tolyloxy-benzenesulfonylmethyl)-1H-pyridin-2-one

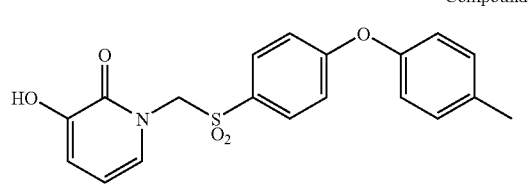

Compound 61

The titled compound was synthesized in a similar manner as described in Example 60 by replacing 1-chloromethanesulfonyl-4-methyl-benzene with 1-chloromethanesulfonyl-4-(p-tolyloxy)-benzene (synthesized according to the following procedures Step A and Step B) in Example 60 Step B. MS (EI) 372 (M+H)+.

Step A. 1-Chloromethanesulfonyl-4-fluoro-benzene

A stirred mixture of 4-fluoro-benzenesulfonyl chloride (10.16 g, 52.2 mmol), sodium sulfite (12.25 g, 97.1 mmol) and sodium bicarbonate (8.02 g, 95.5 mmol) in water (55 mL) is heated at 100° C. for 1 h. The crude sodium sulfinate solution is allowed to cool for 30 min and then treated with bromochloromethane (60 mL) and tetra-N-butyl ammonium bromide (1.68 g, 5.22 mmol). The resulting mixture is heated at 75° C. overnight. The organic layer was separated. The aqueous solution was extracted with $CH_2Cl_2$ (×2). The combined organics were washed with water and brine, and dried over anhydrous $MgSO_4$. The filtration through Celite-silica gel pad and concentration in vacuo gave the desired product without further purification. 1H NMR (300 MHz, $CDCl_3$) 8.00 (m, 2H), 7.30 (m, 2H), 4.53 (s, 2H).

Step B. 1-Chloromethanesulfonyl-4-(p-tolyloxy)-benzene

A mixture of 1-chloromethanesulfonyl-4-fluoro-benzene (0.5 g, 2.4 mmol) from Step A, 4-methyl-phenol (0.21 mL, 2.0 mmol) and $K_2CO_3$ (0.55 g, 4.0 mmol) in dry DMA (10 mL) was heated at 95° C. overnight. The reaction mixture was diluted with EtOAc and water. After the usual work-up, crude product was purified by chromatography (silica gel, 25% EtOAc/hexanes). MS 319 (M+H)+.

Example 62

3-Hydroxy-1-[4-(4-trifluoromethoxy-phenoxy)-benzenesulfonylmethyl]-1H-pyridin-2-one

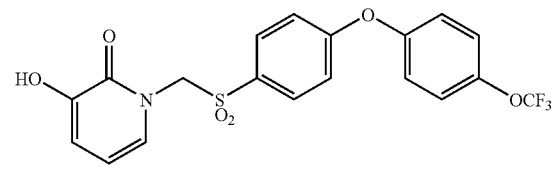

Compound 62

The titled compound was synthesized in a similar manner as described in Example 61 by replacing 4-methyl-phenol with 4-trifluoromethoxy-phenol in Example 61 Step B. MS (EI) 442 (M+H)+.

Example 63

1-(5-Bromo-thiophene-2-sulfonylmethyl)-3-hydroxy-1H-pyridin-2-one

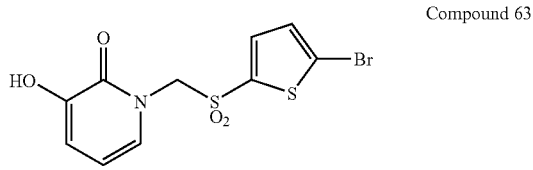

Compound 63

The titled compound was synthesized in a similar manner as described in Example 60 by replacing 1-chloromethanesulfonyl-4-methyl-benzene with 2-bromo-5-chloromethanesulfonyl-thiophene (synthesized from 5-bromo-thiophene-2-sulfonyl chloride according the procedure described in Example 61 step A) and in Example 60 Step B. MS (EI) 350, 352 (M+H)+.

Example 64

3-Hydroxy-1-[5-(4-methoxy-phenyl)-thiophene-2-sulfonylmethyl]-1H-pyridin-2-one

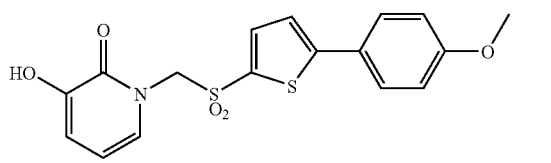

Compound 64

The titled compound was synthesized in a similar manner as described in Example 60 by replacing 1-chloromethane-sulfonyl-4-methyl-benzene with 2-chloromethanesulfonyl-5-(4-methoxy-phenyl)-thiophene (synthesized from 2-bromo-5-chloromethanesulfonyl-thiophene from Example 63 and 4-methoxy-phenyl boronic acid according the procedure described in example 52 Step A) in Example 60 Step B. MS (EI) 378 (M+H)$^+$.

Example 65

1-(4-Bromo-benzenesulfonylmethyl)-3-hydroxy-1H-pyridin-2-one

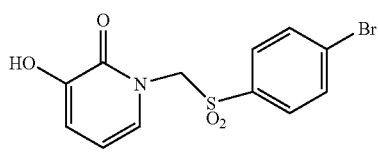

Compound 65

The titled compound was synthesized in a similar manner as described in Example 60 by replacing 1-chloromethane-sulfonyl-4-methyl-benzene with 1-bromo-4-iodomethane-sulfonyl-benzene (synthesized according the following procedure) in Example 60 Step B. MS (EI) 344, 346 (M+H)$^+$.

1-Bromo-4-iodomethanesulfonyl-benzene

A stirred mixture of 4-bromo-benzenesulfonyl chloride (5.12 g, 20 mmol), sodium sulfite (4.69 g, 37.3 mmol) and sodium bicarbonate (3.07 g, 36.6 mmol) in water (20 mL) is heated at 100° C. for 1 h. The crude sodium sulfinate solution is allowed to cool for 30 min and then treated with diiodomethane (25 mL) and tetra-N-butyl ammonium bromide (0.65 g, 2.0 mmol). The resulting mixture is heated at 75° C. overnight. The organic layer was separated. The aqueous solution was extracted with CH$_2$Cl$_2$ (×2). The combined organics were washed with water and brine, and dried over anhydrous MgSO$_4$. The filtration through Celite-silica gel pad and concentration in vacuo gave light yellow liquid residue. Et$_2$O/hexane (1:1) was added to the residue and the mixture was stirred to make homogenous and sit at 0 C for 20 min. The product was crushed out of the solution, filtered and washed with Et$_2$O/hexanes. $^1$H NMR (300 MHz, CDCl$_3$) 7.83 (d, 2H), 7.75 (d, 2H), 4.48 (s, 2H).

Example 66

3-Hydroxy-1-[4-(4-methoxy-phenoxy)-benzene-sulfonylmethyl]-1H-pyridin-2-one

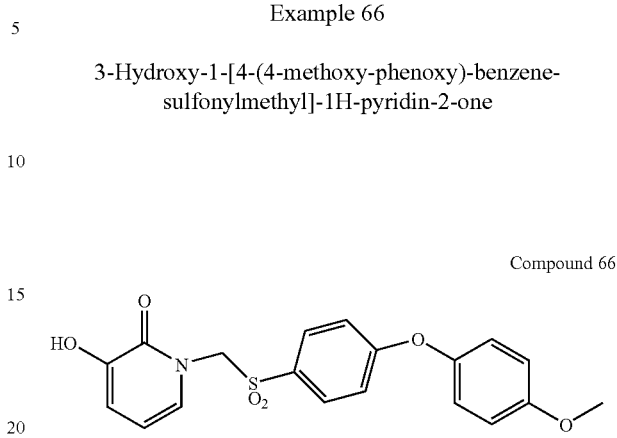

Compound 66

The titled compound was synthesized in a similar manner as described in Example 61 by replacing 4-methyl-phenol with 4-methoxy-phenol in Example 61, Step B. MS: 388 (M+H)$^+$.

Example 67

3-Hydroxy-1-(4'-methoxy-biphenyl-4-sulfonylmethyl)-1H-pyridin-2-one

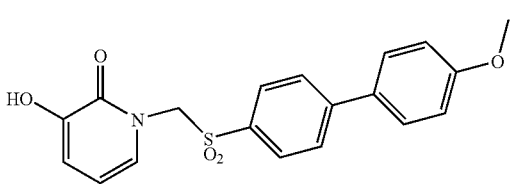

Step A. 3-Benzyloxy-1-(4'-methoxy-biphenyl-4-sulfonylmethyl)-1H-pyridin-2-one

The titled compound was prepared from 3-benzyloxy-1-(4-bromo-benzenesulfonylmethyl)-1H-pyridin-2-one (obtained from Example 65) and 4-methoxy-phenylboronic acid according to the procedure described in Example 52 Step A. MS: 462 (M+H).

Step B. 3-Hydroxy-1-(4'-methoxy-biphenyl-4-sulfonylmethyl)-1H-pyridin-2-one

The titled compound was prepared from 3-benzyloxy-1-(4'-methoxy-biphenyl-4-sulfonylmethyl)-1H-pyridin-2-one from Step A in a similar manner as described in Example 60, Step C. MS: 372 (M+H).

Example 68

(3S)-1-Hydroxy-3-{N-methanesulfonyl-N-[4-(4-trifluoromethylphenoxy)-phenyl]amino}methyl-4-methyl-1,4-diazepan-2-one Compound 68

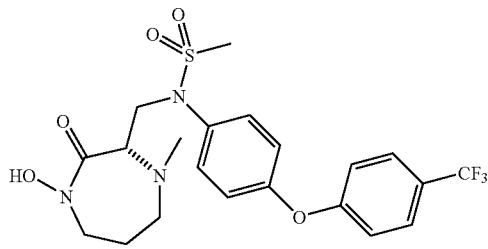

Step A. N-[4-(4-Trifluoromethylphenoxy)phenyl]methanesulfonamide

To a solution of 4-(4-trifluoromethyl-phenoxy)-phenylamine (15.18 g, 60 mmol) and pyridine (7.2 mL, 90 mmol) in dried $CH_2Cl_2$ (100 mL) under $N_2$ at 0° C. was added methanesulfonyl chloride (5.22 mL, 66 mmol) dropwise. The mixture was stirred at 0° C. for 1 h and was then poured into $CH_2Cl_2/H_2O$ (100 mL/100 mL). 2N $HCl_{(aq)}$ (30 mL) was added into additional funnel. The organic layer was then washed with $H_2O$ (100 mL), brine (100 mL), dried ($Na_2SO_4$), and filtered. After removal of solvent, the crude product can be resolidified from $Et_2O$/hexane to give 18.2 g of the titled product (92%) as a pale brown solid. $^1$H NMR (300 MHz, $CDCl_3$) δ 7.58 (d, J=9.0 Hz, 2H), 7.30 (d, J=9.0 Hz, 2H), 7.04 (d, J=9.0 Hz, 4H), 6.93 (s, 1H, NH), 3.04 (s, 3H); MS (EI) 331 ($M^+$), 330 ($M^+$−1, 100).

Step B. N-[(2R)-2-Hydroxy-2-methoxycarbonyl-ethyl]-N-[4-(4-trifluoromethyl-phenoxy)phenyl]methanesulfonamide To a mixture of N-[4-(4-trifluoromethylphenoxy)phenyl]methanesulfonamide (16.55 g, 50 mmol) from Step A, $K_2CO_3$ (17.3 g, 125 mmol), and benzyltriethylammonium chloride (1.135 g, 5 mmol) in dried 1,4-dioxane (75 mL) was added methyl(R)-glycidate (15.3 g, 150 mmol). The mixture was sealed and was heated to 70° C. for 24 h. The mixture was then poured into $Et_2O/H_2O$ (200 mL/200 mL). The organic layer was washed with brine (200 mL), dried ($Na_2SO_4$), and filtered. After removal of solvent, the crude product was recrystallized from $Et_2O$/hexane to give 17.8 g of the product (83%) as a pale brown solid. $^1$H NMR (300 MHz, $CDCl_3$) δ 7.62 (d, J=9.0 Hz, 2H), 7.40 (d, J=9.0 Hz, 2H), 7.10 (d, J=9.0 Hz, 2H), 7.07 (d, J=9.0 Hz, 2H), 4.29 (d, J=6.0 Hz, 1H), 4.03-3.97 (m, 2H), 3.72 (s, 3H), 3.06 (s, 1H, OH), 3.05 (s, 3H); MS (EI) 456 ($M^+$+Na, 100), 434 ($M^+$+1). Anal. Calcd for $C_{18}H_{18}F_3NO_6S$: C, 49.88; H, 4.19; N, 3.23. Found: C, 50.00; H, 4.02; N, 3.22.

Step C. N-[(2R)-2-Methoxycarbonyl-2-trifluoromethanesulfonyloxyethyl]-N-[4-(4-trifluoromethylphenoxy)phenyl]methanesulfonamide To a solution of N-[(2R)-2-hydroxy-2-methoxycarbonyl-ethyl]-N-[4-(4-trifluoro-methyl-phenoxy)phenyl]methanesulfonamide (24 g, 55.4 mmol) from Step B in dried $CH_2Cl_2$ (100 mL) under $N_2$ at ca. −20° C. was added 2,6-lutidine (9.6 mL, 83 mmol) and then methanesulfonic anhydride (10.24 mL, 61 mmol) dropwise. The mixture was stirred for 1 h and was then poured into $CH_2Cl_2/H_2O$ (200 mL/200 mL). 2N $HCl_{(aq)}$ (25 mL) was added into the extraction funnel. The organic layer was washed with $H_2O$ (200 mL), dried ($Na_2SO_4$), and filtered. After removal of solvent, the crude product can be recrystallized from $Et_2O$/hexane to give 28.2 g of the product (90%) as a pale brown solid. $^1$H NMR (300 MHz, $CDCl_3$) δ 7.63 (d, J=9.0 Hz, 2H), 7.39 (d, J=9.0 Hz, 2H), 7.12-7.07 (m, 4H), 5.31 (dd, J=6.0, 3.0 Hz, 1H), 4.34-4.20 (m, 2H), 3.82 (s, 3H), 2.98 (s, 3H).

Step D. N-{(2S)-2-[N-(3-Chloropropyl)-N-methylamino]-2-methoxycarbonylethyl}-N-[4-(4-trifluoromethylphenoxy)phenyl]methanesulfonamide To a solution of N-[(2R)-2-methoxycarbonyl-2-trifluoromethanesulfonyloxyethyl]-N-[4-(4-trifluoromethylphenoxy)phenyl]methanesulfonamide (565 mg, 1.0 mmol) from Step C in dried $CH_2Cl_2$ (2 mL) at 0° C. under $N_2$ was added N-methyl-3-chloropropyl-amine (ca. 1.0 M in $CH_2Cl_2$, 4.0 mL, 4.0 mmol) dropwise. The mixture was allowed to warm to room temperature and was stirred for 1 h. The mixture was directly concentrated to give a crude mixture, which was purified by silica gel chromatography using EtOAc/hexane (1/4 to 1/1) as the eluent to give 455 mg of the product (81%) as a sticky oil. $^1$H NMR (300 MHz, $CDCl_3$) δ 7.62 (d, J=9.0 Hz, 2H), 7.35 (d, J=9.0 Hz, 2H), 7.12-7.04 (m, 4H), 3.96-3.90 (m, 2H), 3.69 (s, 3H), 3.59-3.54 (m, 2H), 3.47 (t, J=7.5 Hz, 1H), 2.94 (s, 3H), 2.75-2.55 (m 2H), 2.27 (s, 3H), 1.90-1.83 (m, 2H); MS (EI) 522 ($M^+$+1, 100).

Step E. N-{(2S)-2-[N-(3-Chloropropyl)-N-methylamino]-2-hydroxycarbonylethyl}-N-[4-(4-trifluoromethylphenoxy)phenyl]methanesulfonamide To a mixture of N-{(2S)-2-[N-(3-Chloropropyl)-N-methylamino]-2-methoxy-carbonylethyl}-N-[4-(4-trifluoromethylphenoxy)phenyl]methanesulfonamide (350 mg, 0.67 mmol) from Step D in THF (1.5 mL) was added lithium hydroxyl (1.0 M in $H_2O$, 1.34 mL, 1.34 mmol) at room temperature. The mixture was stirred at rt for 3 h. Then, $HCl_{(aq)}$ (2 N, 0.67 mL, 0.67 mmol) and hexane (15 mL) were added sequentially. The resulting solid was filtered and was washed with $H_2O$ (50 mL) and hexane (100 mL). The solid was then dried to give 317 mg of the titled compound (92%) as a pale brown solid. $^1$H NMR (300 MHz, $d_6$-DMSO) δ 12.60 (br s, 1H), 7.76 (d, J=9.0 Hz, 2H), 7.46 (d, J=9.0 Hz, 2H), 7.19 (d, J=9.0 Hz, 2H), 7.16 (d, J=9.0 Hz, 2H), 3.96-3.80 (m, 2H), 3.59 (t, J=9.0 Hz, 2H), 3.20 (t, J=7.5 Hz, 1H), 3.00 (s, 3H), 2.67-2.46 (m, 2H), 2.20 (s, 3H), 1.82-1.70 (m, 2H); MS (EI) 509 ($M^+$+1), 507 ($M^+$−1, 100).

Step F. N-{(2S)-2-[N-(3-Chloropropyl)-N-methylamino]-2-(N-triphenylmethoxy)-aminocarbonylethyl}-N-[4-(4-trifluoromethylphenoxy)phenyl]methanesulfonamide To a mixture of N-{(2S)-2-[N-(3-chloropropyl)-N-methylamino]-2-hydroxy-carbonylethyl}-N-[4-(4-trifluoromethylphenoxy)phenyl]methanesulfonamide (255 mg, 0.5 mmol) from Step E, EDC (143 mg, 0.75 mmol), HOBt (101 mg, 0.75 mmol), and 4-N,N-dimethylaminopyridine (92 mg, 0.75 mmol) in $CHCl_3$ (5 mL) was added $Et_3N$ (0.11 mL, 0.75 mmol) under $N_2$ at room temperature. After 30 min stirring, O-tritylhydroxylamine (206 mg, 0.75 mmol) was added and was stirred for 18 h at rt. The mixture was directly concentrated to give a crude mixture, which was purified by silica gel chromatography using EtOAc/hexane (1/4 to 1/1) as the eluent to give 299 mg of the product (78%) as a sticky oil. $^1$H NMR (300 MHz, $CDCl_3$) δ 8.73 (s, 1H), 7.61 (d, J=9.0 Hz, 2H), 7.46 (d, J=9.0 Hz, 4H), 7.73-7.26 (m, 13H), 7.08 (d, J=9.0 Hz, 2H), 7.03 (d, J=9.0 Hz, 2H), 4.09-4.00 (m, 2H), 3.24-3.13 (m, 3H), 2.85 (s, 3H), 2.69-2.55 (m, 2H), 2.05 (s, 3H), 1.65-1.56 (m, 2H); MS (EI) 766 ($M^+$+1), 764 ($M^+$−1, 100).

Step G. (3S)-1-t-Butoxy-3-{N-methanesulfonyl-N-[4-(4-trifluoromethyl-phenoxy)phenyl]amino}methyl-4-methyl-1,4-diazepan-2-one To a mixture of N-{(2S)-2-[N-(3-Chloropropyl)-N-methylamino]-2-(N-triphenyl-methoxy)-aminocarbonylethyl}-N-[4-(4-trifluoromethylphenoxy)phenyl]methane-sulfonamide from Sep F (152 mg, 0.2 mmol), sodium iodide (60 mg, 0.4 mmol), and $Cs_2CO_3$ (196 mg, 0.6 mmol) was added DMF (2 mL) at room temperature. The mixture was stirred at rt for 24 h and was then poured into $Et_2O/H_2O$ (100 mL/100 mL). The organic layer was washed with brine (100 mL), dried ($Na_2SO_4$), and filtered. After removal of solvent, the mixture was purified by silica gel chromatography using EtOAc/hexane (1/4 to 2/3) as the eluent to give 88 mg of the product (60%) as a white solid. $^1$H NMR (300 MHz, $CDCl_3$) δ 7.61 (d, J=9.0 Hz, 2H), 7.40 (d, J=9.0 Hz, 4H), 7.38-7.16 (m, 13H), 7.08 (d, J=9.0 Hz, 2H), 7.00 (d, J=9.0 Hz, 2H), 4.35 (dd, J=12.0, 3.0 Hz, 1H), 4.13 (t, J=12.0 Hz, 1H), 3.71-3.59 (m, 2H), 3.38 (d, J=15.0 Hz, 1H), 3.06 (d, J=12.0 Hz, 1H), 2.87 (s, 3H), 2.84 (d, J=15.0 Hz, 1H), 2.22-2.18 (m, 1H), 1.94 (s, 3H), 1.62-1.56 (m, 1H); MS (EI) 730 ($M^+$+1, 100), 728 ($M^+$−1).

Step H. (3S)-1-Hydroxy-3-{N-methanesulfonyl-N-[4-(4-trifluoromethylphenoxy)-phenyl]amino}methyl-4-methyl-1,4-diazepan-2-one To a suspension of (3S)-1-t-butoxy-3-{N-methanesulfonyl-N-[4-(4-trifluoromethyl-phenoxy)phenyl]amino}methyl-4-methyl-1,4-diazepan-2-one (146 mg, 0.2 mmol) from Step G in $Et_2O$ (0.5 mL) at room temperature was added trifluoroacetic acid (1.5 mL) slowly. The mixture was stirred for 1 h at rt. The mixture was poured into $Et_2O$/pure $H_2O$ (10 mL/30 mL) and hexane (20 mL) was then added. The organic layer was extracted with pure $H_2O$ (30 mL). The aqueous layers were collected and combined. After lyophilization gave 102 mg of the titled compound (85%) as a white trifluoroacetic acid salt. $^1$H NMR (300 MHz, $d_6$-DMSO) δ 10.05-10.00 (br s, 1H), 7.77 (d, J=9.0 Hz, 2H), 7.56 (d, J=9.0 Hz, 2H), 7.21 (d, J=9.0 Hz, 2H), 7.18 (d, J=9.0 Hz, 2H), 4.5-4.0 (m, 5H), 3.37-3.31 (m, 1H), 3.09-3.06 (m, 4H), 2.51 (br s, 3H), 2.14-1.84 (m, 2H); MS (EI) 510 ($M^+$+Na), 488 ($M^+$+1, 100).

Example 69

(3R)-1-Hydroxy-3-(4-phenoxy)benzenesulfonylmethyl-1,4-diazepan-2-one

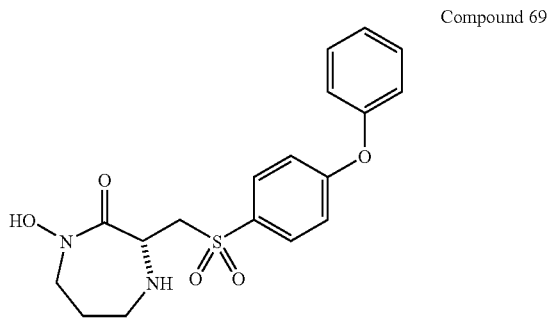

Compound 69

Step A. Methyl (2S)-2-[N-(t-butoxycarbonyl)amino]-3-(4-methylbenzenesulfonyl)-oxypropionate To a solution of N-t-butoxycarbonyl-L-serine methyl ester (6.57 g, 30 mmol) in $CH_2Cl_2$ (30 mL) at 0° C. was added pyridine (10 mL). Then, p-toluenesulfonyl chloride (6.84 g, 36 mmol) was added portionwise. The mixture was allowed to warm to rt and was stirred for 16 h. The mixture was then poured into $EtOAc/H_2O$ (150 mL/100 mL). The organic layer was washed with $H_2O$ (100 mL), brine (100 mL), dried ($Na_2SO_4$), and filtered. After removal of solvent, the mixture was purified by silica gel chromatography using EtOAc/hexane (1/9 to 7/13) as the eluent to give 9.5 g of the desired compound (85%) as a white solid. $^1$H NMR (300 MHz, $CDCl_3$) δ 7.76 (d, J=6.0 Hz, 2H), 7.35 (d, J=9.0 Hz, 2H), 5.34 (d, J=6.0 Hz, 1H), 4.52-4.49 (m, 1H), 4.39 (dd, J=12.0, 3.0 Hz, 1H), 4.29 (dd, J=9.0, 3.0 Hz, 1H), 3.69 (s, 3H), 2.45 (s, 3H), 1.42 (s, 9H).

Step B. Methyl (2R)-2-[N-(t-butoxycarbonyl)amino]-3-(4-phenoxy)thiophen-oxypropionate In a 2-neck flask was placed $K_2CO_3$ (1.035 g, 7.5 mmol) at room temperature. The air was removed and was refilled with $N_2$ for three times. Then, DMF (10 mL) and 4-phenoxythiophenol (1.01 g, 5.0 mmol) were added sequentially. After 5 min stirring, methyl (2S)-2-[N-(t-butoxycarbonyl)amino]-3-(4-methylbenzene-sulfonyl)-oxypropionate (1.865 g, 5.0 mmol) from Step A was added in one portion and the mixture was stirred at rt for 2 h. The mixture was then poured into $Et_2O/H_2O$ (150 mL/100 mL). The organic layer was washed with $H_2O$ (100 mL), brine (100 mL), dried ($Na_2SO_4$), and filtered. After removal of solvent, the mixture was purified by silica gel chromatography using EtOAc/hexane (1/9 to 3/7) as the eluent to give 1.71 g of the product (85%) as a white solid. $^1$H NMR (300 MHz, $CDCl_3$) δ 7.42-7.32 (m, 4H), 7.13 (t, J=6.0 Hz, 1H), 7.02-6.91 (m, 4H), 5.42 (br s, 1H), 4.55 (br s, 1H), 3.59 (s, 3H), 3.31-3.30 (m, 2H), 1.43 (s, 9H); MS (EI) 426 ($M^+$+Na, 100).

Step C. (2R)-2-[N-(t-Butoxycarbonyl)amino]-3-(4-phenoxy)thiophenoxypropionic acid To a solution of methyl (2R)-2-[N-(t-butoxycarbonyl)amino]-3-(4-phenoxy)thiophen-oxypropionate (1.61 g, 4.0 mmol) from Step B in THF (8 mL) at 0° C. as added $LiOH_{(aq)}$ (1 N in $H_2O$, 8.0 mL, 8.0 mmol) dropwise. The mixture was allowed to warm to rt and was stirred for 1 h. The mixture was poured into $EtOAc/H_2O$ (100 mL/100 mL) and HCl (aq) (2 N, 5 mL) was added. The organic layer was washed with $H_2O$ (100 mL), brine (100 mL), dried ($Na_2SO_4$), and filtered. After removal of solvent, the mixture was dried to give 1.50 g of the product (96%) as a sticky oil. $^1$H NMR (400 MHz, $CDCl_3$) δ 7.43-7.32 (m, 4H), 7.13 (t, J=8.0 Hz, 1H), 7.02-6.90 (m, 4H), 5.28 (br d, J=8.0 Hz, 1H), 4.50 (br s, 1H), 3.38 (dd, J=16.0, 4.0 Hz, 1H), 3.27 (dd, J=12.0, 4.0 Hz, 1H), 1.43 (s, 9H); MS (EI) 388 ($M^+$−1, 100).

Step D. (2R)—N-Triphenylmethoxy-2-[N-(t-butoxycarbonyl)amino]-3-(4-phenoxy)-thiophenoxypropionamide To a mixture of (2R)-2-[N-(t-butoxycarbonyl)amino]-3-(4-phenoxy)thiophen-oxypropionic acid (778 mg, 2.0 mmol) from Step C, EDC (573 mg, 3.0 mmol), HOBt (405 mg, 3.0 mmol), and 4-N,N-dimethylaminopyridine (366 mg, 3.0 mmol) in CHCl₃ (10 mL) was added Et₃N (0.42 mL, 3.0 mmol) under N₂ at room temperature. After 10 min stirring, O-tritylhydroxylamine (825 mg, 3.0 mmol) was added and was stirred for 16 h at rt. The mixture was poured into EtOAc/H₂O (150 mL/100 mL). The organic layer was washed with H₂O (100 mL), brine (100 mL), dried (Na₂SO₄), and filtered. After removal of solvent, the product was purified by silica gel chromatography using EtOAc/hexane (1/9 to 1/3) as the eluent to give 890 mg of the product (70%) as a white solid. MS (EI) 645 (M$^+$−1, 100).

Step E. (3R)-4-(t-Butoxycarbonyl)-3-[(4-phenoxy)thiophenoxy]methyl-1-triphenylmethoxy-1,4-diazepan-2-one To a solution of (2R)—N-triphenylmethoxy-2-[N-(t-butoxycarbonyl)amino]-3-(4-phenoxy)-thiophenoxypropionamide (323 mg, 0.5 mmol) from Step D and 3-chloropropyl iodide (102 mg, 0.5 mmol) in DMF/MeCN (1 mL/1 mL) at 0° C. was added Cs₂CO₃ (144 mg, 0.75 mmol). The mixture was allowed to warm to rt and was stirred for 4 h. The mixture was cooled to 0° C. and sodium hydride (60% in mineral oil, 40 mg, 1.0 mmol) was then added. The mixture was allowed to warm to rt and was stirred for 16 h. The mixture was poured into Et₂O/H₂O (100 mL/100 mL). The organic layer was washed with H₂O (100 mL), brine (100 mL), dried (Na₂SO₄), and filtered. After removal of solvent, the product was purified by silica gel chromatography using EtOAc/hexane (1/19 to 1/9) as the eluent to give 65 mg of the product (19%). MS (EI) 709 (M$^+$+Na), 687 (M$^+$+1, 100).

Step F. (3R)-4-(t-Butoxycarbonyl)-3-(4-phenoxy)benzenesulfonylmethyl-1-triphenylmethoxy-1,4-diazepan-2-one To a solution of (3R)-4-(t-butoxycarbonyl)-3-[(4-phenoxy)thiophenoxy]methyl-1-triphenylmethoxy-1,4-diazepan-2-one (60 mg, 0.087 mmol) from Step E in CH₂Cl₂ (2 mL) at 0° C. was added a suspension of 3-chloroperbenzoic acid (77%, 49 mg, 0.22 mmol) in CH₂Cl₂ (1 mL). The mixture was allowed to warm to rt and was stirred for 1 h. The mixture was directly concentrated to give a crude mixture, which was purified by silica gel chromatography using EtOAc/hexane (1/9 to 3/7) as the eluent to give 53 mg of the titled compound (84%) as a white solid. ¹H NMR (300 MHz, CDCl₃) δ 7.64 (d, J=9.0 Hz, 2H), 7.57-7.21 (m, 18H), 7.04 (d, J=9.0 Hz, 2H), 6.97 (d, J=9.0 Hz, 2H), 4.60-4.20 (br m, 3H), 3.90-3.60 (br m, 2H), 3.28 (br d, J=15.0 Hz, 1H), 3.10-3.00 (m, 1H), 2.10-1.90 (m, 1H), 1.76 (br d, J=12.0 Hz, 1H), 1.54 (br s, 3H), 1.34 (br s, 3H), 1.05 (br s, 3H); MS (EI) 741 (M$^+$+Na), 719 (M$^+$+1, 100).

Step G. (3R)-1-Hydroxy-3-(4-phenoxy)benzenesulfonylmethyl-1,4-diazepan-2-one

To a suspension of (3R)-4-(t-butoxycarbonyl)-3-(4-phenoxy)benzene-sulfonylmethyl-1-triphenylmethoxy-1,4-diazepan-2-one (50 mg, 0.07 mmol) from Step F in Et₂O (0.5 mL) at room temperature was added trifluoroacetic acid (1.5 mL) slowly. The mixture was stirred for 1 h at rt. The mixture was poured into Et₂O/pure H₂O (10 mL/30 mL) and hexane (20 mL) was then added. The organic layer was extracted with pure H₂O (30 mL). The aqueous layers were collected and combined. After lyophilization, the product was resolidified from EtOAc/Et₂O/hexane (1/2/7) to gave 25 mg of the titled compound (74%) as a white trifluoroacetic acid salt. ¹H NMR (300 MHz, CD₃CN) δ 7.86 (d, J=9.0 Hz, 2H), 7.46 (d, J=9.0 Hz, 2H), 7.27 (t, J=9.0 Hz, 1H). 7.14-7.10 (m, 2H), 4.32-4.29 (br m, 3H), 3.90-3.60 (br m, 2H), 3.35-3.25 (m, 1H), 3.10-2.90 (m, 2H), 2.00-1.90 (m, 2H); MS (EI) 399 (M$^+$+Na), 376 (M$^+$+1, 100).

Example 70

1-Hydroxy-3-[4-(4-methoxy-phenoxy)-benzenesulfonyl]-azepan-2-one

Compound 70

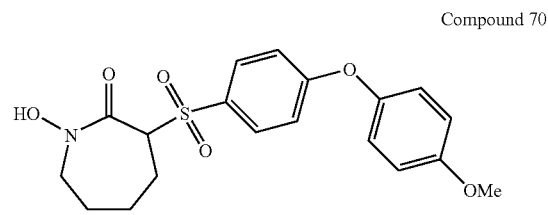

Step A. (4-Fluoro-phenylsulfanyl)-acetic acid methyl ester

To a solution of bromo acetic acid methyl ester (1.53 g, 0.95 ml, 10.0 mmol) and triethylamine (3.0 ml) in dry THF (25 mL) was added 4-fluoro-benzenethiol (1.62 g, 12.6 mmol) in one portion at room temperature. The resulting mixture was heated to reflux and stirred until the TLC showed the completion of the reaction. The reaction mixture was diluted with EtOAc and washed sequentially with aqueous HCl, water and saturated NaCl solution. The organic phase was then dried over anhydrous Na₂SO₄ and concentrated under reduced pressure to gave a crude material, which was then purified by a column chromatography with 0~5% EtOAc in hexanes. MS: 201.3 (M+H)$^+$.

Step B. (4-Fluoro-phenylsulfanyl)-acetic acid

To a refluxed solution of bromo acetic acid methyl ester (1.65 g, 8.24 mmol) in MeOH (15 mL) was added KOH aqueous solution (2.36 g, 42.0 mmol) in 12 ml of H₂O in one portion. The resulting mixture was heated to reflux and stirred until the TLC showed the consumption of the starting material (<15 min). The reaction mixture was concentrated to about 5 ml under reduced pressure and then was acidified with 4N aqueous HCl to pH of 1~2. The white solid formed was filtered and air dried for over night. MS: 185.0 (M–H)$^+$.

Step C. 2-(4-Fluoro-phenylsulfanyl)-N-trityloxy-acetamide

A mixture of (4-fluoro-phenylsulfanyl)-acetic acid (1.52 g, 8.17 mmol) from step B and O-Trityl-hydroxylamine (2.26 g, 10 mmol) in dry DMF was sequentially added NMP (3.0 ml), EDCl (2.05 g, 10.7 mmol), and HOBT (1.45 g, 10.74 mmol). The resulting mixture was stirred at room temperature for overnight. The reaction was diluted with EtOAc and water. The organic layer was washed sequentially with 1N HCl solution, 10% aqueous Na₂CO₃, water and saturated NaCl solution. The organic portion was dried over anhydrous Na₂SO₄ and concentrated under reduced pressure to gave a crude material, which was then purified by a column chromatography with 0~25% EtOAc in hexanes. MS: 466.0 (M+H)$^+$.

Step D. N-(4-Bromo-butyl)-2-(4-fluoro-phenylsulfanyl)-N-trityloxy-acetamide

To a solution of 2-(4-fluoro-phenylsulfanyl)-N-trityloxy-acetamide (132.1 mg, 0.228 mmol) from step C and Cs$_2$CO$_3$ (125.6 mg, 0.385 mmol) in anhydrous DMF (3 mL) was added 1,4-dibromo-butane (0.2 ml, 364.8 mg) in one portion and the resulting solution was warmed to 60° C. After TLC indicated the completion of the reaction (<30 min), the reaction mixture was diluted with EtOAc and washed sequentially with water and saturated NaCl solution. The organic phase was then dried over anhydrous Na$_2$SO$_4$ and concentrated under reduced pressure to give a crude material, which was then used in next step without further purification.

Step E. N-(4-Bromo-butyl)-2-(4-fluoro-benzenesulfonyl)-N-trityloxy-acetamide N-(4-Bromo-butyl)-2-(4-fluoro-phenylsulfanyl)-N-trityloxy-acetamide from step D (105.2 mg, 0.182 mmol) and mCPBA (max. 77%, 0.21 g) in CH$_2$Cl$_2$ was stirred at room temperature for 30 min. The reaction was diluted with CH$_2$Cl$_2$ and water. The organic layer was sequentially washed with saturated Na$_2$CO$_3$ solution, 10% aqueous Na$_2$SO$_3$ and saturated Na$_2$CO$_3$ solution again. The organic phase was then dried and concentrated under the reduced pressure and purified by a column chromatography (0~30% EtOAc in hexane). MS: 632.0, (M+Na)$^+$.

Step F. 3-(4-Fluoro-benzenesulfonyl)-1-trityloxy-azepan-2-one

N-(4-Bromo-butyl)-2-(4-fluoro-benzenesulfonyl)-N-trityloxy-acetamide prepared from step E (170.2 mg, 0.279 mmol) and Cs$_2$CO$_3$ (187.3 mg, 0.575 mmol) in anhydrous DMF (6 mL) was stirred at room temperature for overnight.). The reaction mixture was diluted with EtOAc and washed sequentially with water and saturated NaCl solution. The organic phase was then dried over anhydrous Na$_2$SO$_4$ and concentrated under reduced pressure to gave a crude material, which was then purified by a column chromatography (0~30% EtOAc in hexane). MS: 552.2 (M+Na)$^+$.

Step G. 3-[4-(4-Methoxy-phenoxy)-benzenesulfonyl]-1-trityloxy-azepan-2-one

A Mixture of 3-(4-fluoro-benzenesulfonyl)-1-trityloxy-azepan-2-one prepared from step F (18.9 mg, 0.0357 mmol), 4-methoxy-phenol (19.2 mg, 0.154 mmol) and K$_2$CO$_3$ (38.1 mg, 0.275 mmol) in anhydrous DMA (1.5 mL) was stirred and heated at 100° C. for overnight. The reaction mixture was diluted with EtOAc and washed sequentially with water and saturated NaCl solution. The organic phase was then dried over anhydrous Na$_2$SO$_4$ and concentrated under reduced pressure to gave a crude material, which was then purified by a column chromatography (0~25% EtOAc in hexane). MS: 656.5 (M+Na)$^+$.

Step H. 1-Hydroxy-3-[4-(4-methoxy-phenoxy)-benzenesulfonyl]-azepan-2-one

3-[4-(4-Methoxy-phenoxy)-benzenesulfonyl]-1-trityloxy-azepan-2-one prepared from step G (3.2 mg, 0.00817 mmol) in 1.0 ml of anhydrous CH$_2$Cl$_2$ was added 1.0 ml of TFA and the resulting solution was stirred for 30 min. After TLC indicated the completion of the reaction (<30 min), the reaction mixture was concentrated under reduced pressure to gave a crude material, which was then purified by a column chromatography (0~5% MeOH in CH$_2$Cl$_2$). MS: 391.8 (M+H)$^+$, 413.9 (M+Na)$^+$.

Example 71

1-Hydroxy-3-[4-(4-trifluoromethoxy-phenoxy)-benzenesulfonyl]-azepan-2-one

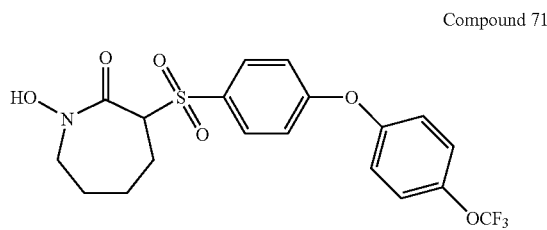

Compound 71

The titled compound was synthesized in a similar manner as described in Example 70 by replacing 4-methoxy-phenol with 4-trifluoromethoxy-phenol in Step G. MS: 448.1 (M+H)$^+$.

Example 72

1-Hydroxy-3-[4-(4-methoxy-phenoxy)-benzenesulfonyl]-piperidin-2-one

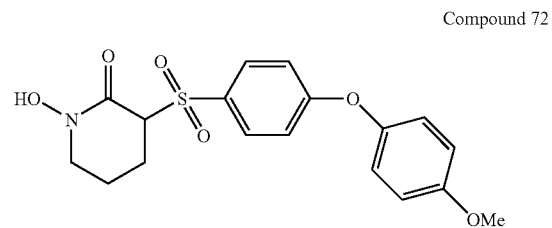

Compound 72

The titled compound was synthesized in a similar manner as described in Example 70 by replacing 1,4-dibromo-butane with 1,3-dibromo-propane in Step D. MS: 378.4 (M+H)$^+$, 400.2 (M+Na)$^+$.

Example 73

1-Hydroxy-3-[4-(4-methoxy-phenoxy)-benzenesulfonyl]-azocan-2-one

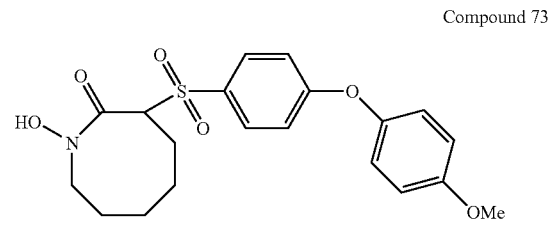

Compound 73

The titled compound was synthesized in a similar manner as described in Example 70 except step G, by replacing 1,4-dibromo-butane with 1,5-dibromo-pentane. MS: 406.0 (M+H)$^+$, 428.1 (M+Na)$^+$.

Example 74

1-Hydroxy-3-[4-(5-trifluoromethyl-1H-benzoimidazol-2-yl)-benzenesulfonyl]-azepan-2-one

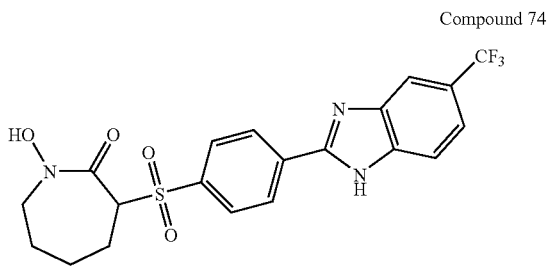

Compound 74

Step A. (4-Hydroxymethyl-phenylsulfanyl)-acetic acid methyl ester

The titled compound was synthesized in a similar manner as described in step A of Example 1 by replacing 4-fluorobenzenethiol with (4-Mercapto-phenyl)-methanol. MS: 235.1 (M+Na)$^+$.

Step B. (4-Hydroxymethyl-phenylsulfanyl)-acetic acid

The titled compound was synthesized in a similar manner as described in step B of Example 1. MS: 220.9 (M+Na)$^+$, 196.9 (M−H)$^+$.

Step C. 2-(4-Hydroxymethyl-phenylsulfanyl)-N-trityloxy-acetamide

The titled compound was synthesized in a similar manner as described in step C of Example 1. MS: 457.1 (M+H)$^+$, 478.2 (M+Na)$^+$.

Step D. N-(4-Bromo-butyl)-2-(4-hydroxymethyl-phenylsulfanyl)-N-trityloxy-acetamide The titled compound was synthesized in a similar manner as described in step D of Example 1. MS: MS: 612.0 (M+Na)$^+$.

Step E. N-(4-Bromo-butyl)-2-(4-hydroxymethyl-benzenesulfonyl)-N-trityloxy-acetamide The titled compound was synthesized in a similar manner as described in step E of Example 1. MS: 644.0 (M+Na)$^+$.

Step F. 3-(4-Hydroxymethyl-benzenesulfonyl)-1-trityloxy-azepan-2-one

The titled compound was synthesized in a similar manner as described in step F of Example 1. MS: 542.2 (M+H)$^+$, 564.2 (M+Na)$^+$.

Step G. 4-(2-Oxo-1-trityloxy-azepane-3-sulfonyl)-benzaldehyde

To a solution of oxalyl chloride (0.12 ml, 2.0 M in dichloromethane) in dichloromethane (5.0 ml) was added DMSO (0.05 ml) at −78 degree C. dropwise. The mixture was stirred for 15 minutes, at which time, 3-(4-hydroxymethyl-benzenesulfonyl)-1-trityloxy-azepan-2-one (60.5 mg in 2 ml of dichloromethane) from step F was added dropwise. The resulting solution was stirred for 30 minutes and then TEA (0.9 ml) was added in one portion. The reaction mixture was stirred and warmed to 0 degree C. for a period of 15 minutes, at which time, the reaction mixture was diluted with dichloromethane and washed sequentially with water and saturated NaCl solution. The organic phase was then dried over anhydrous Na$_2$SO$_4$ and concentrated under reduced pressure to give a crude material, which was then purified by a column chromatography (0~30% EtOAc in hexane). MS: 562.1 (M+Na)$^+$.

Step H. 3-[4-(5-Trifluoromethyl-1H-benzoimidazol-2-yl)-benzenesulfonyl]-1-trityloxy-azepan-2-one 4-(2-Oxo-1-trityloxy-azepane-3-sulfonyl)-benzaldehyde prepared from step G (17.4 mg, 0.0322 mmol) and 4-Trifluoromethyl-benzene-1,2-diamine (23.6 mg, 0.13 mmol) in 5.0 ml of anhydrous EtOH was heated to reflux and a 1.2 ml aqueous solution of NaHSO$_3$ (100.1 mg) was added in one portion. The resulting solution was stirred and heated to reflux for overnight. The reaction mixture was concentrated under reduced pressure and diluted with EtOAc and water. The organic phase was washed sequentially with water and saturated NaCl solution, and then dried over anhydrous Na$_2$SO$_4$. The EtOAc solution was concentrated under reduced pressure to give a crude material, which was then purified by a column chromatography (0~10% EtOAc in hexane and dichloromethane 1:1). MS: 696.2 (M+H)$^+$.

Step J. 1-Hydroxy-3-[4-(5-trifluoromethyl-1H-benzoimidazol-2-yl)-benzene-sulfonyl]-azepan-2-one 3-[4-(5-trifluoromethyl-1H-benzoimidazol-2-yl)-benzenesulfonyl]-1-trityloxy-azepan-2-one prepared from step H (8.2 mg, 0.0117 mmol) in 0.75 ml of anhydrous CH$_2$Cl$_2$ was added 0.75 ml of TFA and the resulting solution was stirred for 30 min. After TLC indicated the completion of the reaction (<30 min), the reaction mixture was concentrated under reduced pressure to gave a crude material, which was then purified by a column chromatography (0~5% MeOH in EtOAc and CH$_2$Cl$_2$ 1:1). MS: 454.0 (M+H)$^+$, 476.0 (M+Na)$^+$.

Example 75

1-Hydroxy-3-[4-(5-methyl-1H-benzoimidazol-2-yl)-benzenesulfonyl]-azepan-2-one

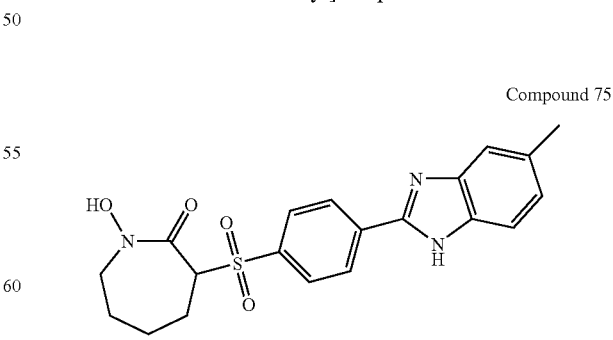

Compound 75

The titled compound was synthesized in a similar manner as described in Example 74 by replacing 4-trifluoromethyl-benzene-1,2-diamine with 4-methyl-benzene-1,2-diamine in Step H. MS: 400.0 (M+H)$^+$.

Example 76

2-[4-(1-Hydroxy-2-oxo-azepane-3-sulfonyl)-phenyl]-1H-benzimidazole-5-carbonitrile

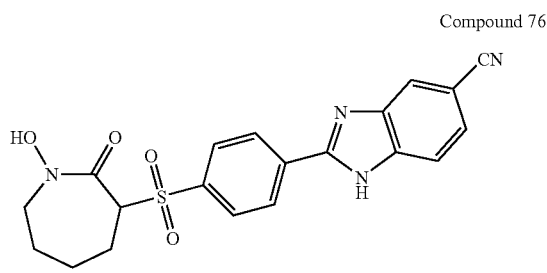

Compound 76

The titled compound was synthesized in a similar manner as described in Example 74 by replacing 4-trifluoromethyl-benzene-1,2-diamine with 3,4-diamino-benzonitrile in Step H. MS: 411.1 (M+H)$^+$, 433.0 (M+Na)$^+$.

Example 77

1-Hydroxy-3-[4-(5-methoxy-1H-benzoimidazol-2-yl)-benzenesulfonyl]-azepan-2-one

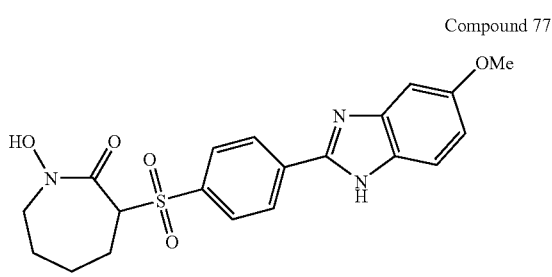

Compound 77

The titled compound was synthesized in a similar manner as described in Example 74 by replacing 4-trifluoromethyl-benzene-1,2-diamine with 4-methoxy-benzene-1,2-diamine in Step H. MS: 416.1 (M+H)$^+$, 438.0 (M+Na)$^+$.

Example 78

3-[4-(5-Fluoro-1H-benzoimidazol-2-yl)-benzenesulfonyl]-1-hydroxy-azepan-2-one

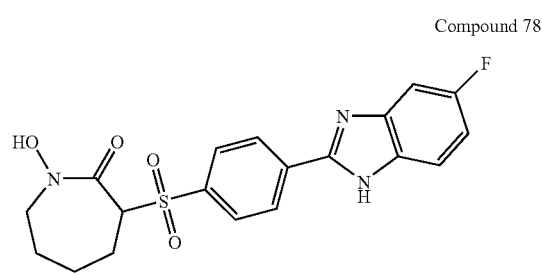

Compound 78

The titled compound was synthesized in a similar manner as described in Example 74 by replacing 4-trifluoromethyl-benzene-1,2-diamine with 4-fluoro-benzene-1,2-diamine in Step H. MS: 404.1 (M+H)$^+$, 426.0 (M+Na)$^+$.

Example 79

3-(4-Fluoro-benzenesulfonyl)-1-hydroxy-azepan-2-one

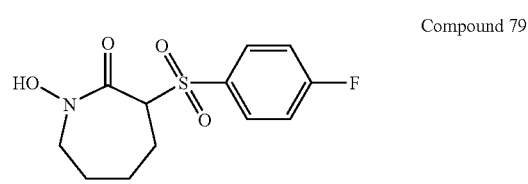

Compound 79

The titled compound was synthesized in a similar manner as described in Example 70, except that step G was omitted. MS: 288.0 (M+H)$^+$.

Example 80

1-Hydroxy-3-(4'-methoxy-biphenyl-4-sulfonyl)-azepan-2-one

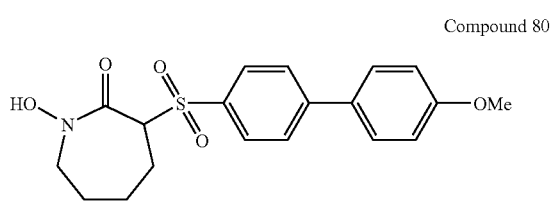

Compound 80

Step A. (4-Bromo-phenylsulfanyl)-acetic acid methyl ester

The titled compound was synthesized in a similar manner as described in step A of Example 70 except by replacing 4-fluoro-benzenethiol with 4-bromo-benzenethiol.

Step B. (4-Bromo-phenylsulfanyl)-acetic acid

The titled compound was synthesized in a similar manner as described in step B of Example 70. MS: 246.9 (M−H)$^+$.

Step C. 2-(4-Bromo-phenylsulfanyl)-N-trityloxy-acetamide

The titled compound was synthesized in a similar manner as described in step C of Example 70. MS: 526.0 (M+H)$^+$.

Step D. N-(4-Bromo-butyl)-2-(4-bromo-phenylsulfanyl)-N-trityloxy-acetamide

The titled compound was synthesized in a similar manner as described in step D of Example 70.

Step E. N-(4-Bromo-butyl)-2-(4-bromo-benzenesulfonyl)-N-trityloxy-acetamide

The titled compound was synthesized in a similar manner as described in step E of Example 70. MS: 693.9 (M+Na)$^+$.

Step F. 3-(4-Bromo-benzenesulfonyl)-1-trityloxy-azepan-2-one

The titled compound was synthesized in a similar manner as described in step F of Example 70. MS: 612.0 (M+Na)+.

Step G. 3-(4'-Methoxy-biphenyl-4-sulfonyl)-1-trityloxy-azepan-2-one

The mixture of 3-(4-Bromo-benzenesulfonyl)-1-trityloxy-azepan-2-one prepared from step F (10.1 mg, 0.0171 mmol), 4-Methoxybenzeneboronic acid (10.2 mg, 0.0671 mmol) and Pd(PPh$_3$)$_4$ (3.1 mg, 0.00268 mmol) in 2.0 ml of toluene was added 0.4 ml of saturated Na$_2$CO$_3$ aqueous solution and the resulting mixture was stirred and heated to reflux for 4 hours. The reaction mixture was filtered through celite and diluted with EtOAc and water. The organic phase was washed sequentially with water and saturated NaCl solution, and then dried over anhydrous Na$_2$SO$_4$. The EtOAc solution was concentrated under reduced pressure to give a crude material, which was then purified by a column chromatography (0~30% EtOAc in hexane). MS: 618.2 (M+H)+, 640.2 (M+Na)+.

Step H. 1-Hydroxy-3-(4'-methoxy-biphenyl-4-sulfonyl)-azepan-2-one 3-(4'-Methoxy-biphenyl-4-sulfonyl)-1-trityloxy-azepan-2-one prepared from step G (5.1 mg, 0.00826 mmol) in 0.75 ml of anhydrous CH$_2$Cl$_2$ was added 0.75 ml of TFA and the resulting solution was stirred for 30 min. After TLC indicated the completion of the reaction (<30 min), the reaction mixture was concentrated under reduced pressure to gave a crude material, which was then purified by a column chromatography (0~5% MeOH in CH$_2$Cl$_2$). MS: 376.0 (M+H)+, 398.1 (M+Na)+.

Example 81

3-(4-Bromo-benzenesulfonyl)-1-hydroxy-azepan-2-one

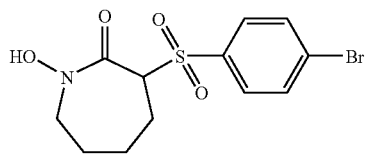

Compound 81

The titled compound was synthesized in a similar manner as described in Example 80 except that step G was omitted. MS: 348.0 (M+H)+, 370.0 (M+Na)+.

Example 82

3-(4'-Chloro-biphenyl-4-sulfonyl)-1-hydroxy-azepan-2-one

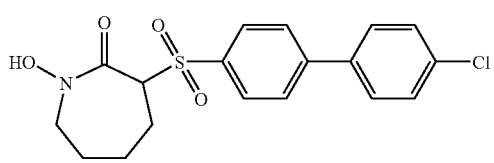

Compound 82

The titled compound was synthesized in a similar manner as described in Example 80 by replacing 4-methoxybenzeneboronic acid with 4-chlorobenzeneboronic acid in Step G. MS: 380.1 (M+H)+, 402.0 (M+Na)+.

Example 83

3-(Biphenyl-4-sulfonyl)-1-hydroxy-azepan-2-one

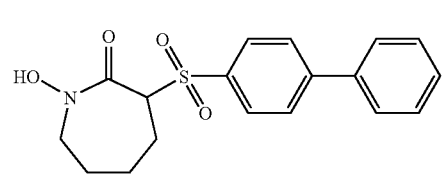

Compound 83

The titled compound was synthesized in a similar manner as described in Example 80 by replacing 4-methoxybenzeneboronic acid with phenylboronic acid in step G. MS: 346.0 (M+H)+, 368.1 (M+Na)+.

Example 84

4'-(1-Hydroxy-2-oxo-azepane-3-sulfonyl)-biphenyl-4-carbonitrile

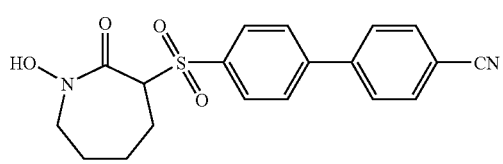

Compound 84

The titled compound was synthesized in a similar manner as described in Example 80 by replacing 4-methoxybenzeneboronic acid with 4-cyanophenylboronic acid in Step G. MS: 371.1 (M+H)+, 393.0 (M+Na)+.

Example 85

1-Hydroxy-3-(4'-trifluoromethoxy-biphenyl-4-sulfonyl)-azepan-2-one

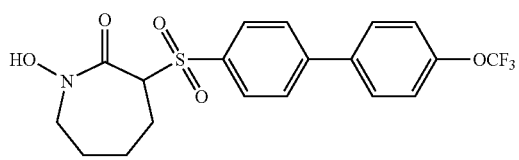

Compound 85

The titled compound was synthesized in a similar manner as described in Example 80 by replacing 4-methoxybenzeneboronic acid with 4-trifluoromethoxy)benzeneboronic acid in Step G. MS: 430.0 (M+H)+, 452.1 (M+Na)+.

Example 86

1-Hydroxy-3-(4'-methyl-biphenyl-4-sulfonyl)-azepan-2-one

Compound 86

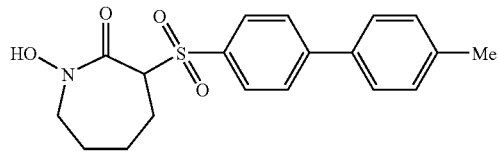

The titled compound was synthesized in a similar manner as described in Example 80 by replacing 4-methoxybenzeneboronic acid with 4-methylbenzeneboronic acid in Step G. MS: 360.1 (M+H)$^+$, 382.0 (M+Na)$^+$.

Example 87

4-(4-Chloro-phenoxy)-N-(1-hydroxy-2-oxo-1,2-dihydro-pyridin-3-yl)-N-(2-morpholin-4-yl-ethyl)-benzenesulfonamide Compound 87

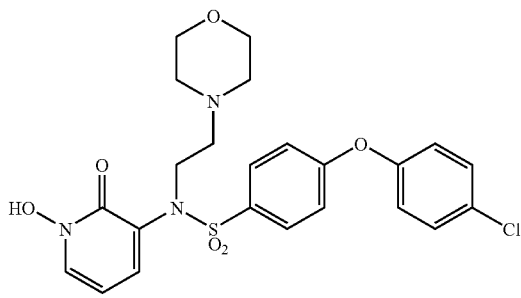

The titled compound was synthesized in a similar manner as described in Example 22 by replacing 4-phenoxy-benzenesulfonyl chloride with 4-(4-chloro-phenoxy)-benzene-sulfonyl chloride in Step A; and replacing benzylbromide with 4-(2-chloro-ethyl)-morpholine in Step B. MS: 506 (M+H)$^+$.

Example 88

N-(1-Hydroxy-2-oxo-1,2-dihydro-pyridin-3-yl)-N-(2-thiomorpholin-4-yl-ethyl)-4-p-tolyloxy-benzenesulfonamide Compound 98

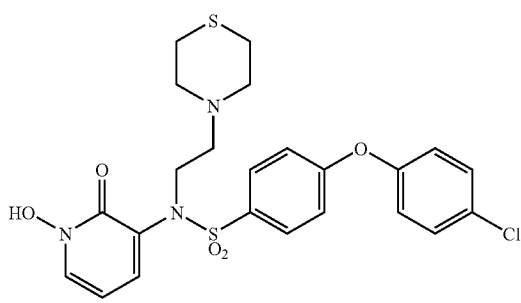

The titled compound was synthesized in a similar manner as described in Example 22 (above) by replacing 4-phenoxy-benzenesulfonyl chloride with 4-(4-chloro-phenoxy)-benzenesulfonyl chloride in Step A; and modified the procedure of Step B as follows. MS: 521 (M+H)$^+$.

Step B. N-(2-morpholin-4-yl-ethyl)-N-(2-bromo-pyridin-3-yl)-4-(4-chloro-phenoxy)-benzenesulfonamide To a suspension of N-(2-bromo-pyridin-3-yl)-4-phenoxy-benzene-sulfonamide (0.38 g, 0.94 mmol) from step A and Cs$_2$CO$_3$ (0.92 g, 2.81 mmol) in dry DMF (10 mL) was added 1,2-dibromoethane (0.38 g, 2.0 mmol). The resulting mixture was heated at 50 C overnight. The cooled reaction was diluted with EtOAc and water. The aqueous layer was extracted with EtOAc (×3) and the combined organics were washed with water and brine, dried over anhydrous Na$_2$SO$_4$, and filtered through Celite. The filtrate was concentrated under the reduced pressure and purified by chromatography (silica gel, 10% EtOAc/hexanes) to give N-(2-bromoethyl)-N-(2-bromo-pyridin-3-yl)-4-(4-chloro-phenoxy)-benzenesulfonamide. MS: 544, 546 (M+H)$^+$. To a solution of this intermediate (0.4 g, 0.73 mmol) in dry DMF was added slowly thiomorpholine (0.19 g, 1.83 mmol) and the mixture was warm to 40 C for 2 h. The usual work-up and purification by chromatography (35% EtOAc/hexanes) provided the product N-(2-morpholin-4-yl-ethyl)-N-(2-bromo-pyridin-3-yl)-4-(4-chloro-phenoxy)-benzenesulfonamide. MS: 567, 569 (M+H)$^+$.

Example 89

4-(4-Chloro-phenoxy)-N-[2-(4-methyl-piperazin-1-yl)-ethyl]-N-(2-oxo-1,2-dihydro-pyridin-3-yl)-benzenesulfonamide Compound 99

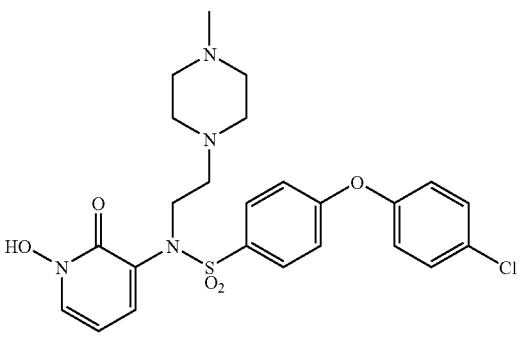

The titled compound was synthesized in a similar manner as described in Example 88 by replacing thiomorpholine with 1-methyl-piperazine in Step B MS: 518 (M+H)$^+$.

Following the general synthetic procedures outlined above and specific steps in Examples 1-89, the compounds of Table 1 below were prepared.

TABLE 1
| Compound No. | Structure |
|---|---|
| 42 | 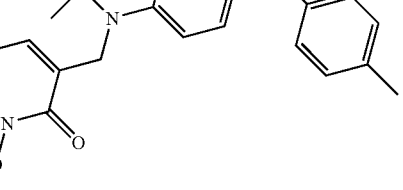 |
| 51 | 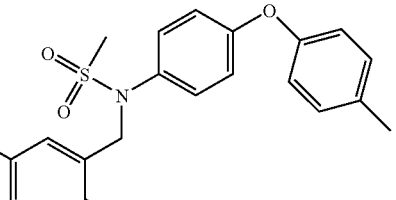 |
| 43 | 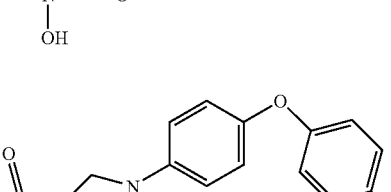 |
| 45 | 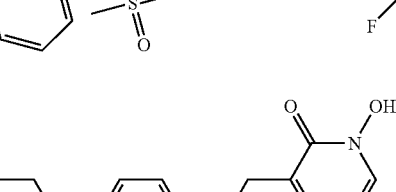 |
| 46 | 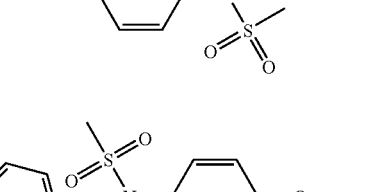 |
| 53 | 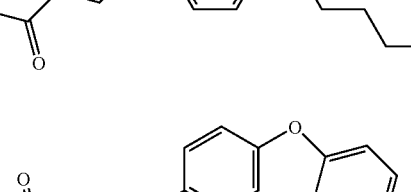 |

TABLE 1-continued

| Compound No. | Structure |
| --- | --- |
| 44 | 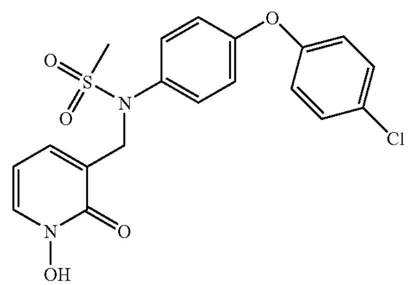 |
| 49 | 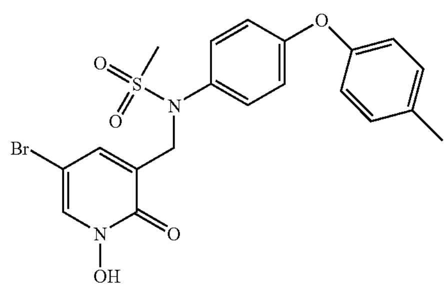 |
| 54 | 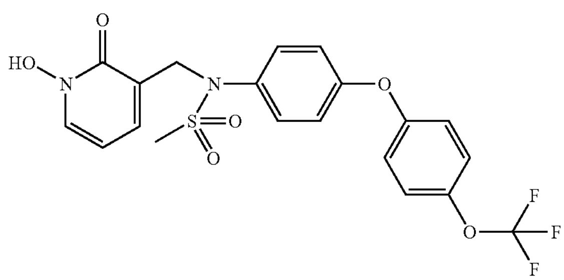 |
| 48 | 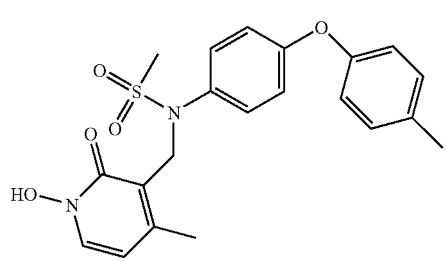 |
| 50 | 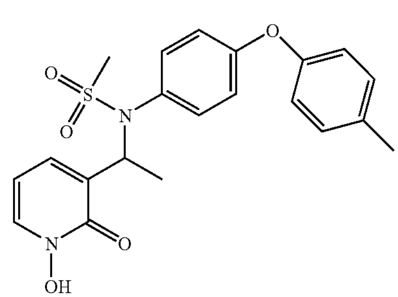 |

TABLE 1-continued

| Compound No. | Structure |
|---|---|
| 41 | 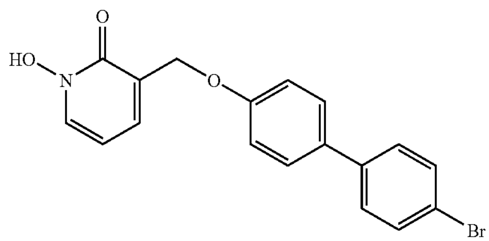 |
| 47 | 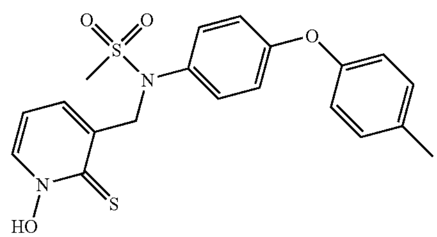 |
| 55 | 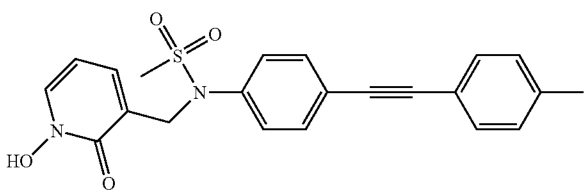 |
| 56 | 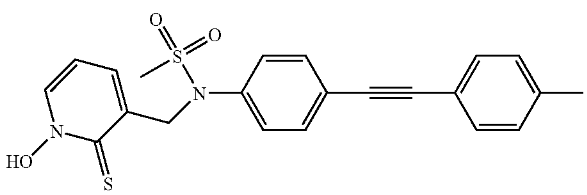 |
| 52 | 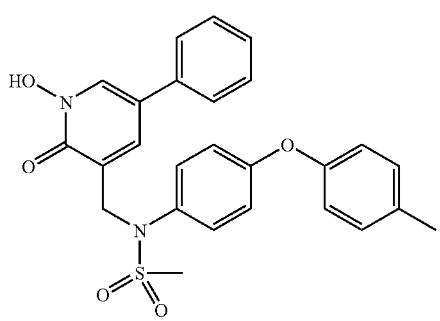 |
| 23 | 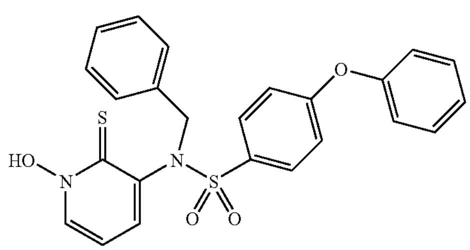 |

TABLE 1-continued

| Compound No. | Structure |
|---|---|
| 22 | 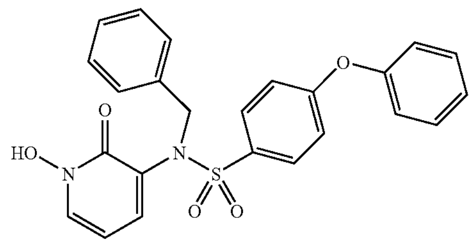 |
| 25 | 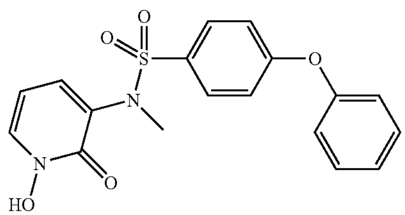 |
| 27 | 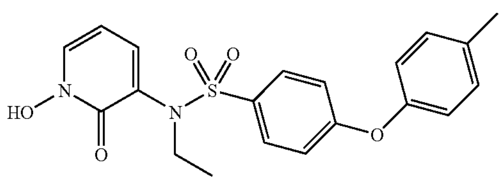 |
| 24 | 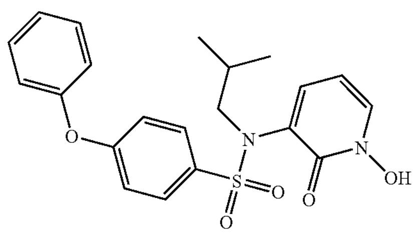 |
| 26 | 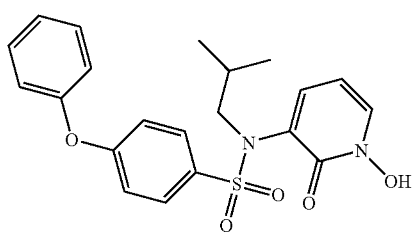 |
| 37 | 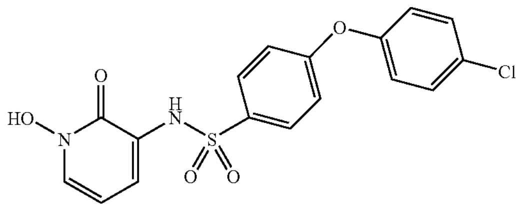 |
| 28 | 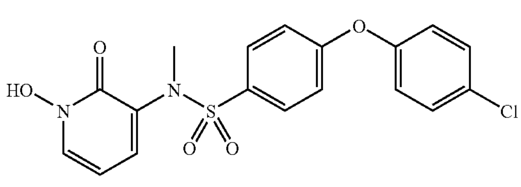 |

TABLE 1-continued

| Compound No. | Structure |
|---|---|
| 29 | 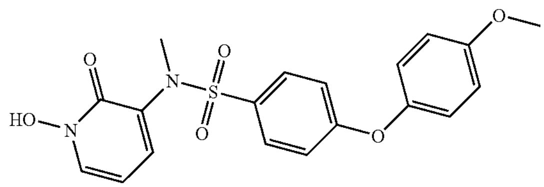 |
| 30 | 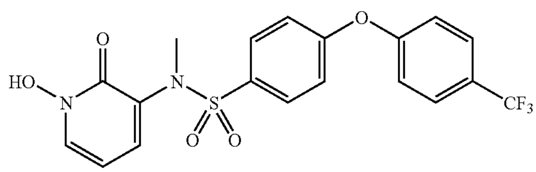 |
| 39 | 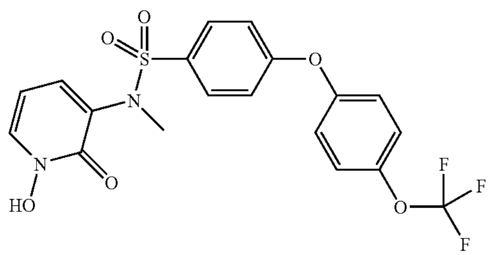 |
| 31 | 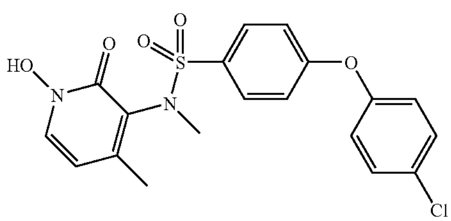 |
| 32 | 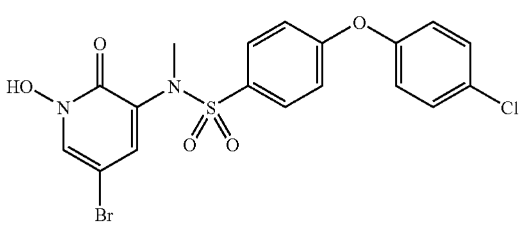 |
| 33 | 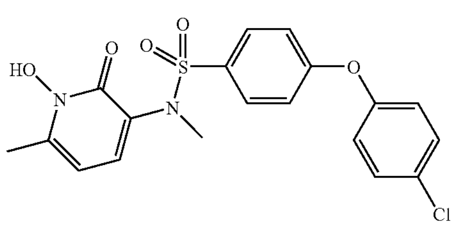 |
| 36 | 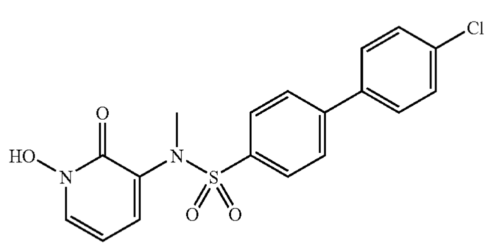 |

TABLE 1-continued

| Compound No. | Structure |
| --- | --- |
| 38 | 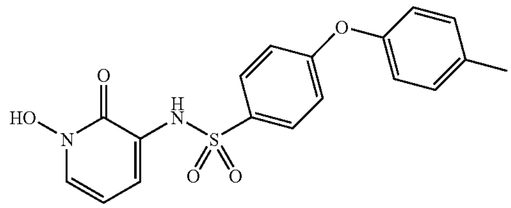 |
| 34 | 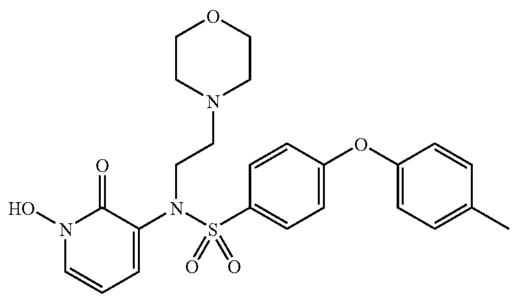 |
| 35 | 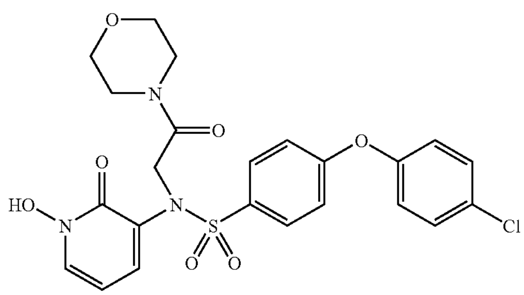 |
| 40 | 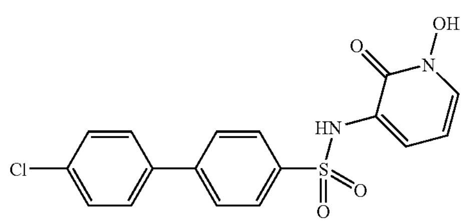 |
| 58 | 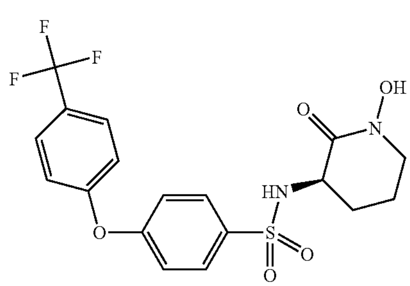 |
| 57 | 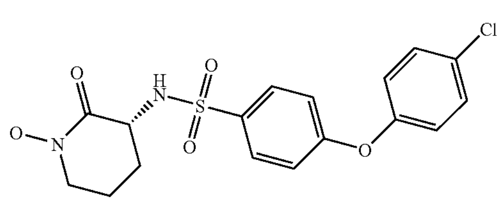 |

TABLE 1-continued

| Compound No. | Structure |
| --- | --- |
| 59 | 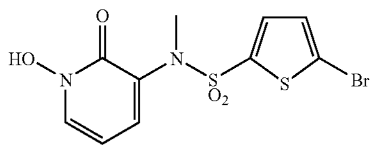 |
| 60 | 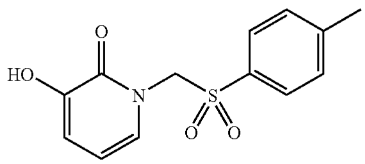 |
| 61 | 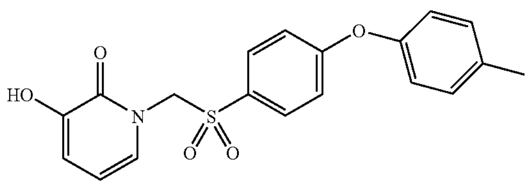 |
| 62 | 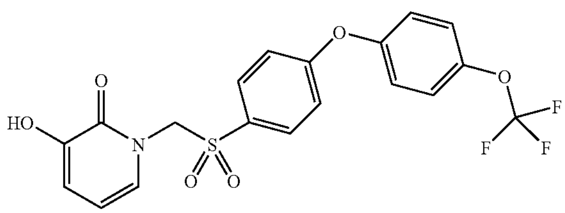 |
| 63 | 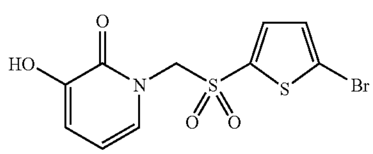 |
| 64 | 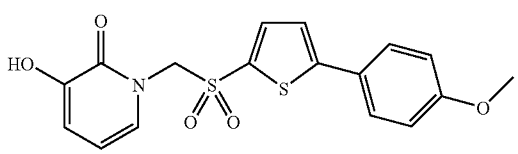 |
| 65 | 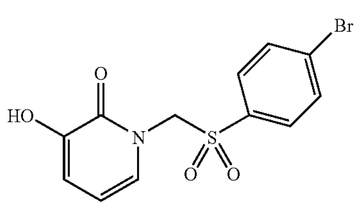 |
| 66 | 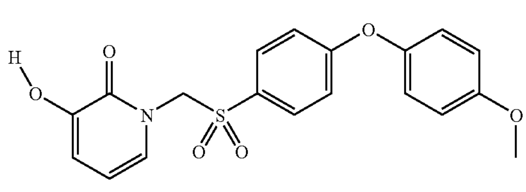 |

TABLE 1-continued

| Compound No. | Structure |
|---|---|
| 67 | 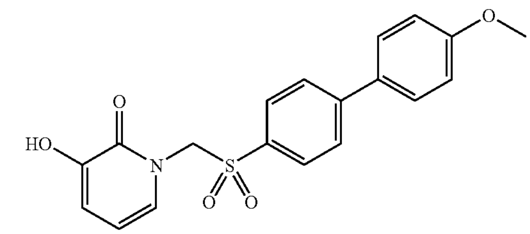 |
| 88 | 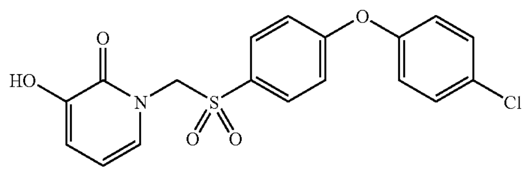 |
| 2 | 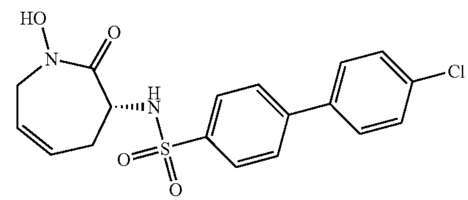 |
| 1 | 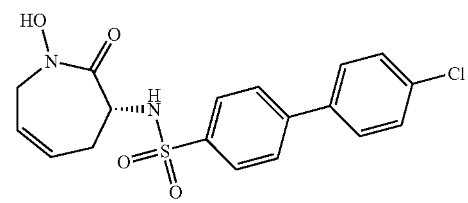 |
| 12 | 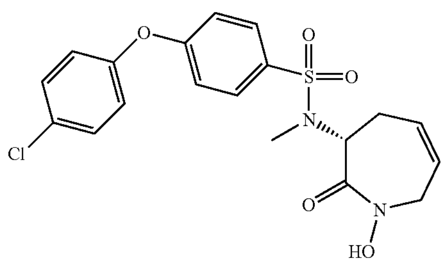 |
| 3 | 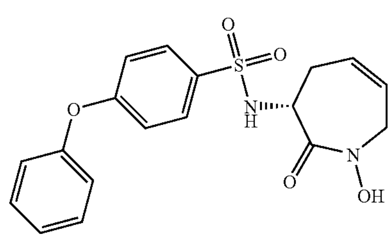 |
| 4 | 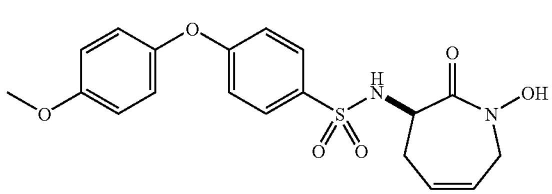 |

TABLE 1-continued

| Compound No. | Structure |
|---|---|
| 5 | 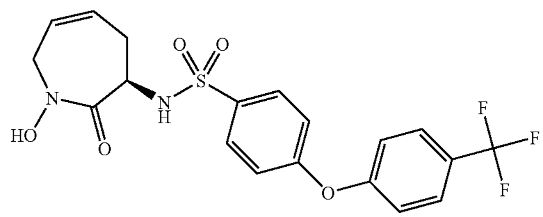 |
| 6 | 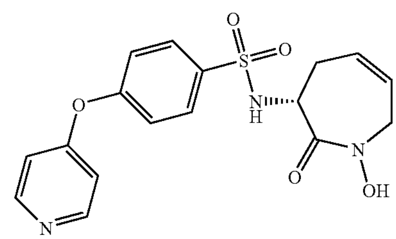 |
| 9 | 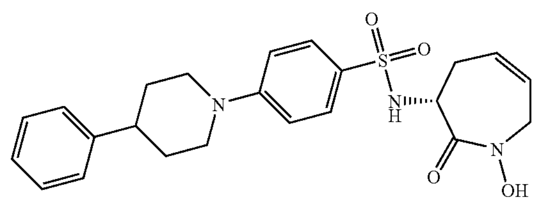 |
| 10 | 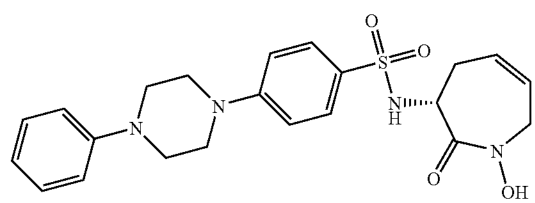 |
| 20 | 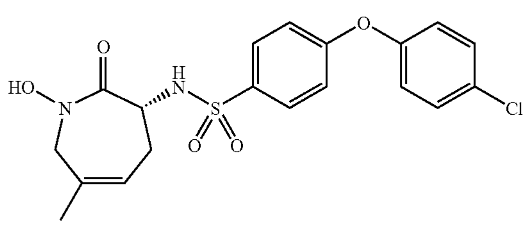 |
| 11 | 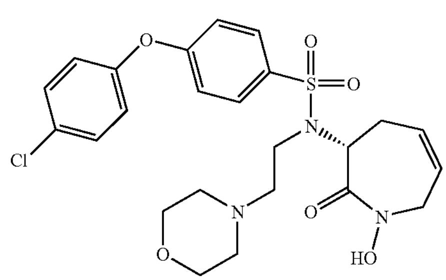 |

TABLE 1-continued
| Compound No. | Structure |
| --- | --- |
| 7 | 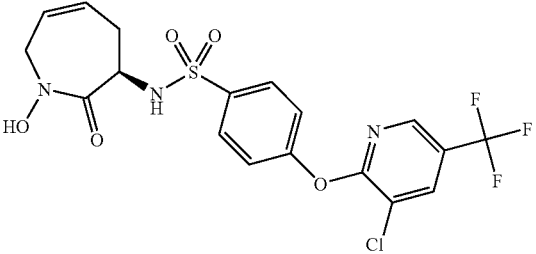 |
| 8 | 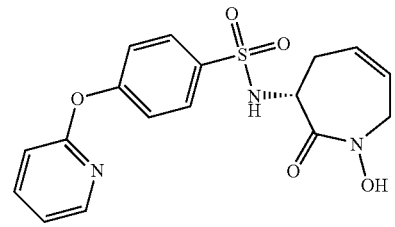 |
| 15 | 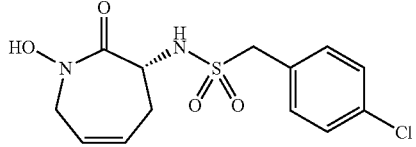 |
| 16 | 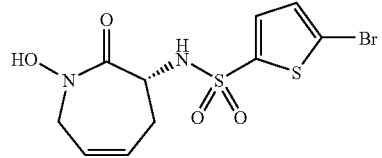 |
| 17 | 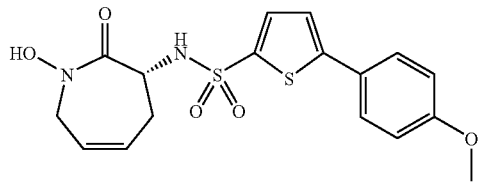 |
| 18 | 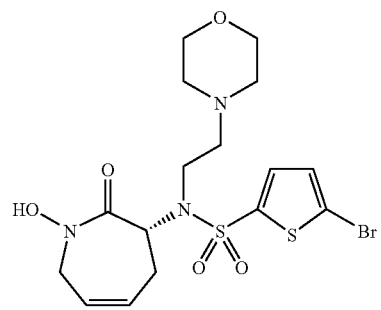 |

TABLE 1-continued

| Compound No. | Structure |
|---|---|
| 89 | 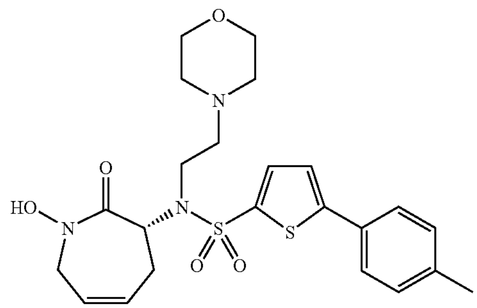 |
| 90 | 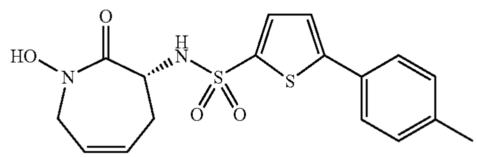 |
| 91 | 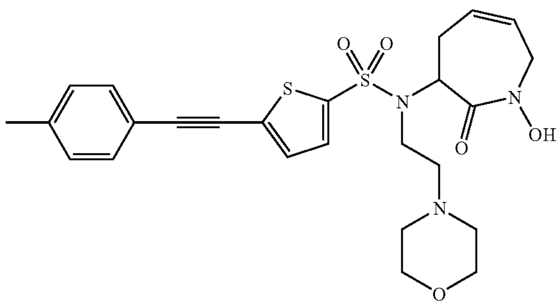 |
| 92 | 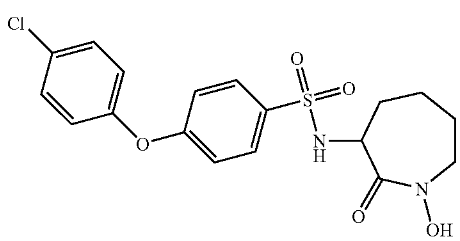 |
| 93 | 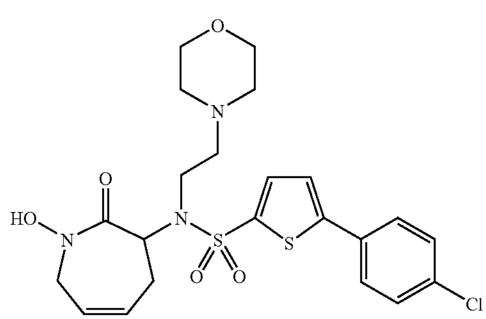 |

TABLE 1-continued

| Compound No. | Structure |
| --- | --- |
| 19 | 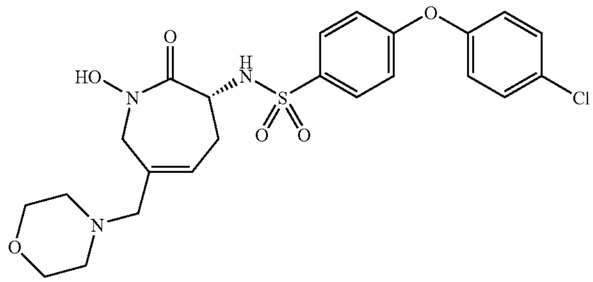 |
| 13 | 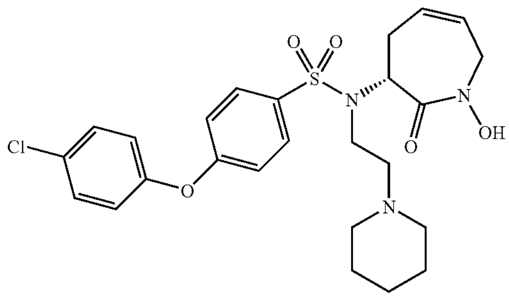 |
| 14 | 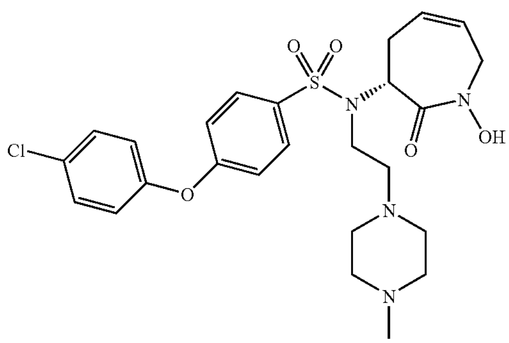 |
| 21 | 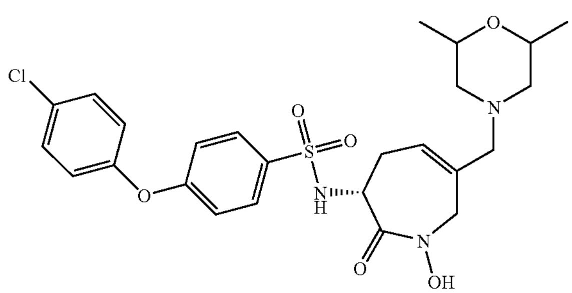 |
| 94 | 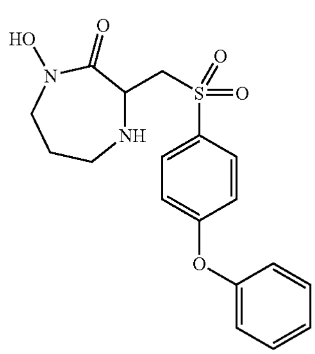 |

TABLE 1-continued

| Compound No. | Structure |
|---|---|
| 72 | (structure) |
| 70 | (structure) |
| 71 | (structure) |
| 79 | (structure) |
| 73 | (structure) |
| 74 | (structure) |
| 78 | (structure) |

TABLE 1-continued

| Compound No. | Structure |
|---|---|
| 77 | 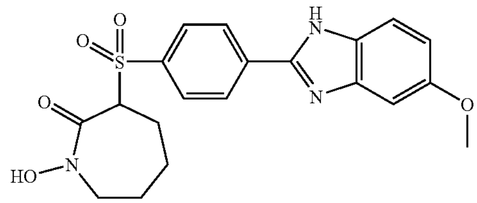 |
| 76 | 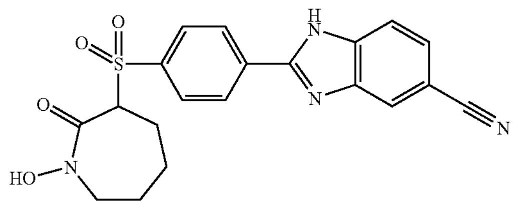 |
| 75 | 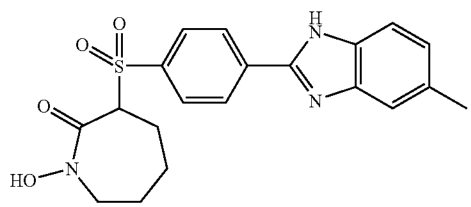 |
| 81 | 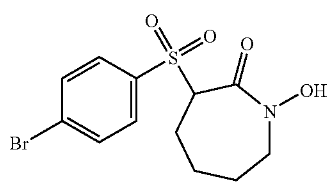 |
| 95 | 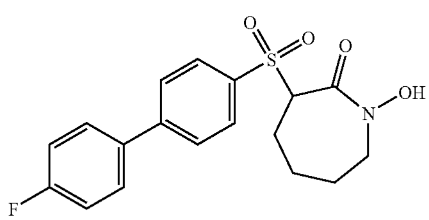 |
| 80 | 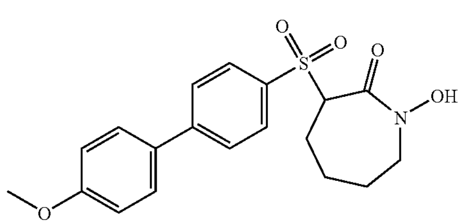 |
| 82 | 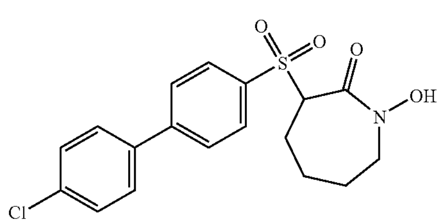 |

TABLE 1-continued

| Compound No. | Structure |
|---|---|
| 83 | 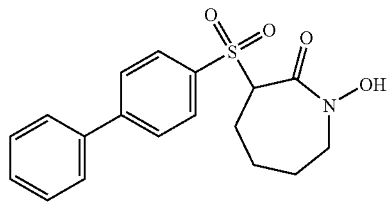 |
| 84 | 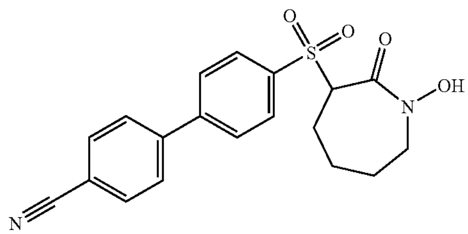 |
| 85 | 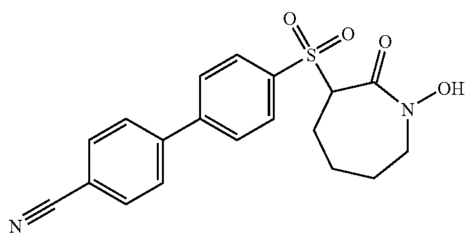 |
| 86 | 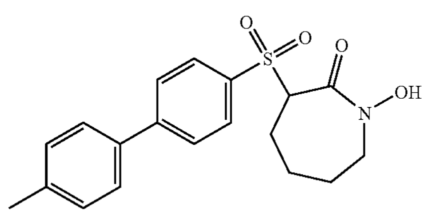 |
| 87 | 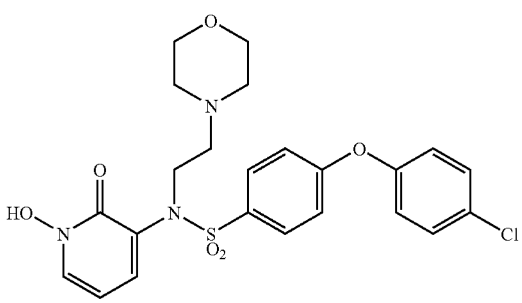 |
| 96 | 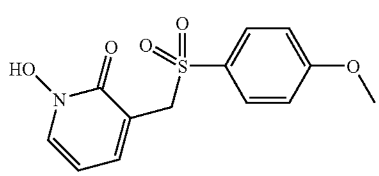 |
| 97 | 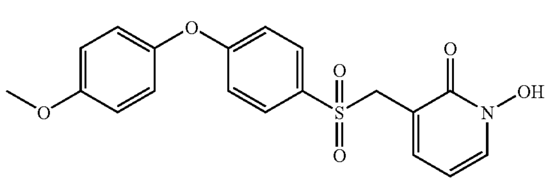 |

TABLE 1-continued

| Compound No. | Structure |
|---|---|
| 69 | 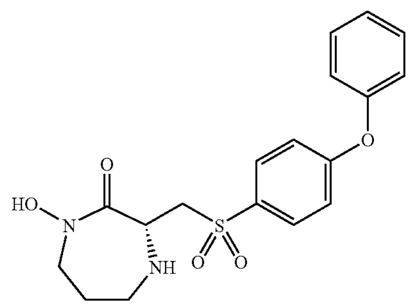 |
| 68 | 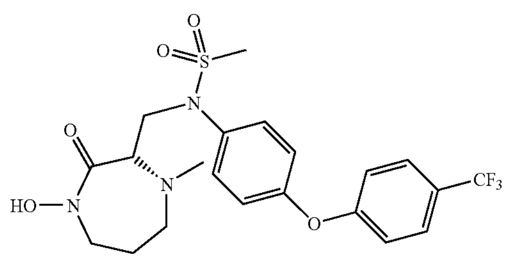 |
| 98 | 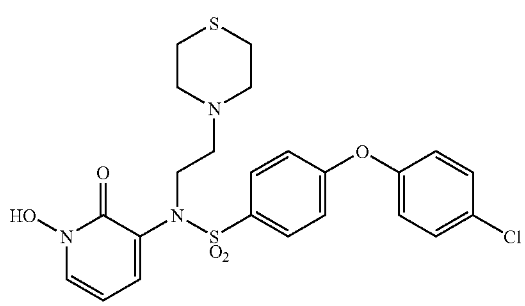 |
| 99 | 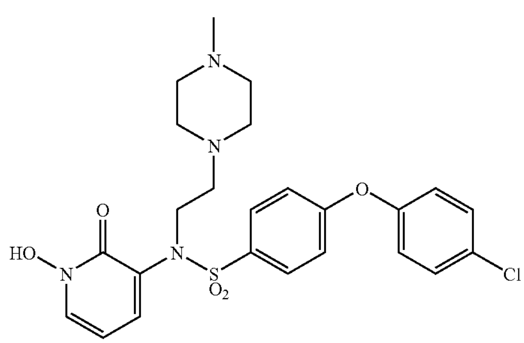 |

Biological Assays and Activity

MMP Enzymatic Assays

Reagents
10×MMP Assay Buffer: (500 mM HEPES pH 7.4, 100 mM CaCl$_2$, 0.5% Brij-35)
Trupoint Peptide [Acetyl-Cys(Eu)-Pro-Leu-Gly-Leu-Lys-(QSY7)-Ala-Arg-amide], 500 µM stock in DMSO
MMP Enzymes
  Human MMP-1 catalytic domain (aa 100-262), 3234 µM stock
  Human MMP-2 full length (aa 1-660), 22.4 µM stock
  Human MMP-3 catalytic domain (aa 100-265), 72.8 µM stock
  Human MMP-9 catalytic domain (aa 107-446), 14.2 µM stock,
  Human MMP-13 catalytic domain (aa 103-268), 663 µM stock
  Rat MMP-9 catalytic domain (aa 108-446), 18.7 µM stock General Well Setup: 20 µl compound solution
20 µl enzyme solution
10 µl substrate solution
50 µl total volume 1) Prepare appropriate 1×MMP assay buffer from 10× stock. Will need ~30 ml per 384-well plate.
2) Resuspend dry powdered compound to 100 mM in 100% DMSO.
3) Want to have a final top concentration in the assay of 1 µM compound. Need to prepare a 2.5× concentration stock (2.5 µM) to achieve this concentration in 50 µl. Dilute compound to 2.5 mM in 100% DMSO (a 1:40 dilution), then dilute the 2.5 mM compound to 2.5 µM (1:1000) into 1× assay buffer. Make 1 ml 2.5 µM compound in assay buffer.
4) Fill the rows B through P of a 384-well plate with assay buffer+0.1% DMSO.
5) Add 30 ul of the 2.5 µM compound in assay buffer to the top row of the plate, doing each compound in triplicate. The plate setup should be as follows, using GM6001 as plate reference compound:

| 1, 2, 3 | 4, 5, 6 | 7, 8, 9 | 10, 11, 12 | 13, 14, 15 | 16, 17, 18 | 19, 20, 21 | 22, 23, 24 |
|---|---|---|---|---|---|---|---|
| cmpd1 | cmpd2 | cmpd3 | cmpd4 | cmpd5 | cmpd6 | GM6001 | DMSO |

6) Serially dilute 10 µl down the plate to achieve 1:3 dilutions in subsequent wells. After each dilution, change pipette tips to avoid compound carryover. Discard the remaining 10 µl after diluting into the final row.
7) Prepare enzyme dilutions at 2.5× of final desired concentration (see below). Will need 10 ml enzyme solution per plate. Add enzyme to plate, 20 µl per well. Incubate 1 hr.

| Enzyme | Stock (µM) | Final (µM) | 2.5× (µM) | Dilution |
|---|---|---|---|---|
| hMMP-1 | 3234 | 0.625 | 1.562 | 1:2070 |
| hMMP-2 | 22.4 | 0.015 | 0.038 | 1:600 |

-continued

| Enzyme | Stock (µM) | Final (µM) | 2.5× (µM) | Dilution |
|---|---|---|---|---|
| hMMP-3 | 72.8 | 0.063 | 0.16 | 1:455 |
| hMMP-9 | 14.2 | 0.030 | 0.075 | 1:190 |
| hMMP-13 | 663 | 0.094 | 0.235 | 1:2821 |
| rMMP-9 | 18.7 | 0.094 | 0.235 | 1:80 |

8) Dilute the 500 µM Trupoint peptide 1:1000 into assay buffer to achieve a 5× working stock of 500 nM. Prepare 5 ml total per plate. Add 10 ul of substrate to each well to achieve a final concentration of 100 nM in well. Also prepare background subtraction wells by adding 10 µl 5× substrate to 40 µl assay buffer per well, typically do ~32 wells.
9) Incubate assay at room temperature for 15 min. Read in plate reader.

| Plate Reading Specifications | |
|---|---|
| Excitation Wavelength: | 340 nM |
| Emission Wavelength: | 615 nM |
| Number of Flashes: | 100 |
| Delay Before Reading: | 300 msec |

Analysis Specifications
  Calculate average background value from substrate/assay buffer wells
  Subtract this from entire plate
  Calculate average of DMSO wells for each enzyme. This is the positive control, 100% value.
  For each well, calculate percent of control by dividing well value by the average DMSO value obtained above.
  Paste percent of control values into Graphpad Prism 4.0. Calculate IC$_{50}$ values by fitting values to a curve established by nonlinear regression.
  Use sigmoidal dose-response, variable slope
  Constrain values from 0 to 100

In-Vivo Activity in Ischemic Stroke Model

Rat Focal Ischemia Model

All experiments were performed using an institutionally approved protocol following the National Institutes of Health Guide for the Care and Use of Laboratory Animals. Sprague-Dawley rats (male, weighing 250 to 280 g from Charles River) were anesthetized with isoflurane (2% to 2.5%) under spontaneous respiration in pure oxygen. The animal was positioned faced up and an incision was made at ventral cervical midline. The right external carotid artery (ECA) and common carotid artery were exposed and ligated. The right internal carotid artery (ICA) was temporarily clipped. A small incision was made in the ECA and a tip-rounded 3-0 filament suture was gently inserted into ICA until feeling a minor resistance. At this point, the right middle cerebral artery (MCA) was occluded at its original site. Two hours later, reperfusion was achieved by withdrawal of the occluding filament.

Brain Edema Evaluation

Twenty-four hours after ischemia, the rats were deeply anesthetized with 5% isoflorane and the brain removed. The brain samples were heated in a vacuumed-oven for 24 hours, and the brain water content was calculated using the following formula: (wet weight−dry weight)/wet weight*100%. The brain edema was expressed as the difference of brain water content between ipsilateral and contralateral hemisphere.

Compounds listed in Table 2 below were tested in the above assay(s):

TABLE 2

| Cpd | MMP-2 nM $IC_{50}$ | MMP-9 nM $IC_{50}$ |
| --- | --- | --- |
| 42 | 207.990 | 46.850 |
| 51 | 240.990 | 43.950 |
| 43 | 490.910 | 232.810 |
| 45 | >1,000 | >1,000 |
| 46 | >1,000 | >1,000 |
| 53 | 183.650 | 14.690 |
| 44 | 405.790 | 126.210 |
| 49 | 546.520 | 116.200 |
| 54 | 465.590 | 11.070 |
| 48 | >1,000 | 457.090 |
| 50 | 2,552.700 | 223.360 |
| 41 | >10,000 | 7144.960 |
| 47 | >1000 | 486.410 |
| 55 | >10,000 | >10,000 |
| 56 | >10,000 | >10,000 |
| 52 | 914.110 | 316.960 |
| 23 | 4591.980 | 693.420 |
| 22 | 22.39 | 33.42 |
| 25 | 1.520 | 1.410 |
| 27 | 6.500 | 3.600 |
| 24 | 41.020 | 57.540 |
| 26 | 6.100 | 3.400 |
| 37 | 242.100 | 315.500 |
| 28 | 6.900 | 3.280 |
| 29 | 5.600 | 0.870 |
| 30 | 104.470 | 32.660 |
| 39 | 5.750 | 1.850 |
| 31 | 66.220 | 158.490 |
| 32 | 662.217 | 1386.756 |
| 33 | 66.370 | 34.910 |
| 36 | 1300.000 | 1800.000 |
| 38 | 49.770 | 64.560 |
| 34 | 3.500 | 2.410 |
| 35 | 4.930 | 4.840 |
| 40 | >1,000 | >1,000 |
| 58 | 46.660 | 743.020 |
| 57 | 108.390 | 57.940 |
| 60 | 467.730 | 1066.720 |
| 61 | 16.670 | 45.830 |
| 62 | 13.59 | 4.910 |
| 63 | >1,000 | 668.340 |
| 64 | 184.580 | 522.200 |
| 65 | >1000 | >1000 |
| 66 | 84.500 | 56.090 |
| 67 | >10000 | >10000 |
| 88 | 10.6 | 16.4 |
| 2 | 68.550 | 1142.890 |
| 1 | 0.810 | 0.780 |
| 12 | 1.990 | 1.320 |
| 3 | 1.070 | 1.760 |
| 5 | 1.790 | 2.040 |
| 6 | 2.670 | 15.940 |
| 9 | >1,000 | >1,000 |
| 10 | >1000 | >1000 |
| 20 | 0.720 | 0.680 |

TABLE 2-continued

| Cpd | MMP-2 nM $IC_{50}$ | MMP-9 nM $IC_{50}$ |
| --- | --- | --- |
| 11 | 0.310 | 0.200 |
| 7 | >1,000 | >1,000 |
| 8 | 15.100 | 22.850 |
| 15 | >1,000 | >1,000 |
| 16 | 43.050 | 28.440 |
| 17 | 3.900 | 10.670 |
| 18 | 48.080 | 14.350 |
| 89 | 6.7 | 10.5 |
| 90 | 4.2 | 8.6 |
| 91 | 2.2 | 0.6 |
| 92 | 3.7 | 5.9 |
| 93 | 16.4 | 17.2 |
| 19 | 0.390 | 0.770 |
| 13 | 0.550 | 0.210 |
| 14 | 0.490 | 0.200 |
| 21 | 1.250 | 0.89 |
| 68 | 1253.141 | 405.509 |
| 94 | 36.813 | 21.135 |
| 72 | 167.494 | 87.902 |
| 70 | 95.940 | 30.974 |
| 71 | 110.408 | 44.361 |
| 79 | >1,000 | >1,000 |
| 73 | >1,000 | >1,000 |
| 74 | >1,000 | >1,000 |
| 78 | 376.600 | 846.1 |
| 77 | >1,000 | >1,000 |
| 76 | >1,000 | >1,000 |
| 75 | >1,000 | >1,000 |
| 81 | >1,000 | >1,000 |
| 95 | 584.000 | 1186.000 |
| 80 | >1,000 | >1,000 |
| 82 | >1,000 | >1,000 |
| 83 | >1,000 | >1,000 |
| 84 | >1,000 | >1,000 |
| 85 | >1,000 | >1,000 |
| 86 | >1,000 | >1,000 |
| 96 | >1,000 | >1,000 |
| 97 | 17.258 | 7.261 |
| 87 | 5.0 | 4.2 |
| 69 | 46.7 | 30.6 |
| 98 | 6.1 | 4.9 |
| 99 | 1.7 | 1.3 |

The present invention is not to be limited in terms of the particular embodiments or examples described in this application, which are intended as single illustrations of individual aspects of the invention. Many modifications and variations of this invention can be made without departing from its spirit and scope, as will be apparent to those skilled in the art. Functionally equivalent methods and combinations within the scope of the invention, in addition to those enumerated herein will be apparent to those skilled in the art from the foregoing description, examples and accompanying drawings. Such modifications and variations are intended to fall within the scope of the appended claims. The present invention is to be limited only by the terms of the appended claims, along with the full scope of equivalents to which such claims are entitled.

REFERENCES CITED

All references cited herein are incorporated herein by reference in their entirety and for all purposes to the same extent as if each individual publication or patent or patent application was specifically and individually indicated to be incorporated by reference in its entirety for all purposes.

The discussion of references herein is intended merely to summarize the assertions made by their authors and no admission is made that any reference constitutes prior art. Applicants reserve the right to challenge the accuracy and pertinence of the cited references.

The invention claimed is:
1. A compound of Formula (I):

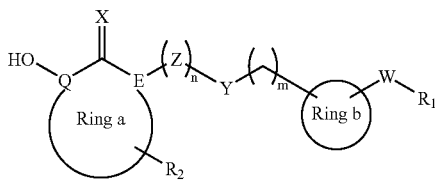

wherein
Ring a is a 7, -membered heterocyclyl consisting of 6 carbons and one nitrogen, wherein
X is O
E is selected from an

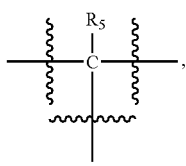

wherein
$R_5$ is selected from H, hydroxy, amino, alkoxy, alkylthio, sulfonyl, $C_{1-10}$alkyl, $C_{2-6}$alkenyl, $C_{2-6}$alkynyl, aryl, heteroaryl, and heterocyclyl, and
Q is N;
Ring b is selected from
aryl;
heteroaryl; and
heterocyclyl of the formula

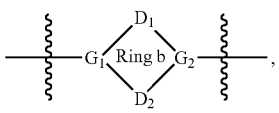

wherein
$G_1$ and $G_2$ are independently selected from N, C, and CH; and
$D_1$ and $D_2$ are each 1-3 independent members selected from CH, $CH_2$, N, S, and O, provided that when $G_1$ or $G_2$ is N, $D_1$ and $D_2$ are independently selected from CH and $CH_2$;
$R_1$ is selected from halo, nitrile, hydroxyl, thiol, amino, alkoxy, alkylthio, sulfonyl, $C_{1-10}$alkyl, $C_{2-6}$alkenyl, $C_{2-6}$alkynyl, cycloalkyl, aryl, heteroaryl, heterocyclyl, carbonyl, and —CHO;
$R_2$ is 0-2 independent members selected from halo, nitrile, hydroxyl, amino, $C_{1-10}$alkyl, $C_{2-6}$alkenyl, $C_{2-6}$alkynyl, alkoxy, alkylthio, sulfonyl, aryl, heteroaryl, heterocyclyl, —C(O)$R_3$, —C(O)O$R_3$, and —C(O)N$R_3R_4$, wherein
$R_3$ and $R_4$ are independently selected from H, $C_{1-10}$alkyl, aryl, heteroaryl, and heterocyclyl, or
$R_3$ and $R_4$ together with the N they are attached to form a 3-, 4-, 5-, 6-, or 7-membered heterocyclyl;
W is selected from a covalent bond, —(CH$_2$)$_p$—O—, —O—(CH$_2$)$_p$—, —S(O)$_p$—, —C(O)—, $C_{1-3}$alkylene, $C_{2-3}$alkenylene, $C_{2-3}$alkynylene, and 5-7 membered aliphatic ring containing one or two nitrogens, wherein
p is 0, 1, or 2;
Y is selected from O, S, S(O), S(O)$_2$, —SO$_2$N(R$_6$)—, —N(R$_6$) SO$_2$—, —N(R$_6$) SO$_2$N(R$_7$)—, —N(R$_6$)CO—, —N(R$_6$)PO(OR$_8$)—, —N(SO$_2$R$_8$)—, —N(COR$_8$)—, —N(POOR$_8$R$_9$)—, —CH(OH)—,

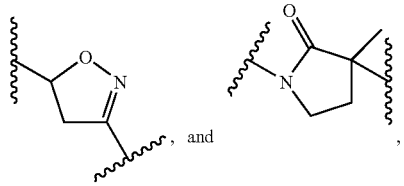

wherein
$R_6$ and $R_7$ are independently selected from H, $C_{1-10}$alkylsulfonyl, arylsulfonyl, alkylcarbonyl, and arylcarbonyl, and
$R_8$ and $R_9$ are independently selected from $C_{1-6}$alkyl, aryl, heteroaryl, and heterocyclyl;
Z is —CH(R$_{10}$)— or —CH(R$_{10}$)CH(R$_{11}$)—, wherein
$R_{10}$ and $R_{11}$ are independently selected from H, $C_{1-6}$alkyl, $C_{2-6}$alkenyl, $C_{2-6}$alkynyl, aryl, heteroaryl, and heterocyclyl;
m is 0, 1, or 2; and
n is 0 or 1 with the proviso that when n is 0, E is not N and Y is not O;
or an optical isomer, enantiomer, diastereomer, racemate, prodrug or pharmaceutically acceptable salt thereof.
2. The compound of claim 1 wherein ring a is selected from

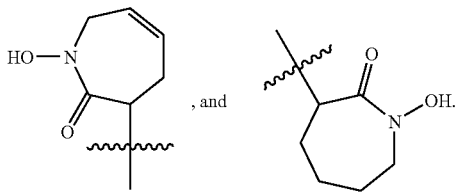

3. The compound of claim 1 wherein ring b is 5 or 6-membered aryl or 5 or 6-membered heteroaryl.
4. The compound of claim 1 wherein ring b is fused ring aryl or fused ring heteroaryl wherein the two points of attachment are on two rings.
5. The compound of claim 1 wherein ring b is phenyl or

6. The compound of claim 1 wherein $R_1$ is selected from halo, alkoxy, $C_{1-10}$alkyl, aryl, heteroaryl, and heterocyclyl.
7. The compound of claim 1 wherein $R_2$ is 0-1 member selected from halo, $C_{1-10}$alkyl, and aryl.
8. The compound of claim 1 wherein Q is N.

9. The compound of claim 1 wherein E is

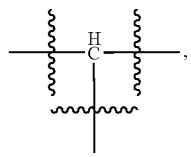

10. The compound of claim 1 wherein X is O.
11. The compound of claim 1 wherein Z is —CH($R_{10}$)— wherein $R_{10}$ is H or $C_{1-6}$alkyl.
12. The compound of claim 1 wherein Y is selected from O, S(O)$_2$, —N(R$_6$)SO$_2$—, —N(SO$_2$R$_8$)—, wherein $R_6$ is H or $C_{1-10}$alkyl, and $R_8$ is $C_{1-10}$alkyl.
13. The compound of claim 1 wherein W is selected from a covalent bond, O, —O—(CH$_2$)—, $C_{1-3}$alkylene, and $C_{2-3}$alkynylene.
14. The compound of claim 1 wherein m is 0 or 1.
15. The compound of claim 1 wherein n is 0.
16. The compound of claim 1 wherein n is 1.
17. The compound of claim 1 wherein
Ring a is selected from

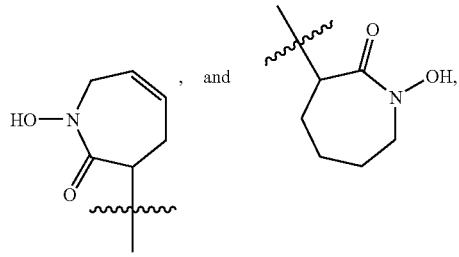

Ring b is 5 or 6-membered aryl or 5 or 6-membered heteroaryl;
$R_1$ is selected from halo, alkoxy, $C_{1-10}$alkyl, aryl, heteroaryl, and heterocyclyl;
$R_2$ is 0-1 member selected from halo, $C_{1-10}$alkyl, and aryl;
Z is —CH($R_{10}$)— wherein $R_{10}$ is H or $C_{1-6}$alkyl;
Y is selected from O, S(O)$_2$, —N(R$_6$)SO$_2$—, and —N(SO$_2$R$_8$)—, wherein $R_6$ is H or $C_{1-10}$alkyl, and $R_8$ is $C_{1-10}$alkyl
W is selected from a covalent bond, O, —O—(CH$_2$)—, $C_{1-3}$alkylene, and $C_{2-3}$alkynylene; and
m is 0 or 1.
18. The compound of claim 1 wherein
Ring a is selected from

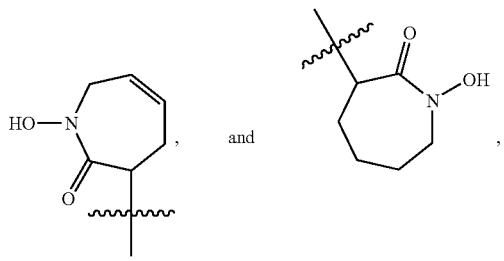

Ring b is phenyl or

$R_1$ is selected from Br, Cl, F, $C_{1-4}$alkoxy, $C_{1-4}$alkyl, phenyl,

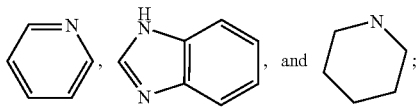

$R_2$ is selected from 0-1 member selected from Br, $C_{1-4}$alkyl, and phenyl;
Z is —CH($R_{10}$)— wherein $R_{10}$ is H or $C_{1-4}$alkyl;
Y is selected from O, S(O)$_2$, —N(R$_6$)SO$_2$—, and —N(SO$_2$R$_8$)—, wherein $R_6$ is H or $C_{1-4}$alkyl, and $R_8$ is $C_{1-4}$alkyl;
W is selected from a covalent bond, O, —O—(CH$_2$)—, $C_{1-3}$alkylene, and —C≡C—; and
m is 0 or 1.
19. The compound of claim 18 wherein n is 1.
20. The compound of claim 18 wherein n is 0.
21. The compound of claim 18 wherein m is 0.
22. The compound of claim 18 wherein W is O or a covalent bond.
23. The compound of claim 18 wherein ring b is phenyl.
24. The compound of claim 18 wherein $R_1$ is phenyl.
25. The compound of claim 18 wherein n is 1 and Z is —CH$_2$—.
26. The compound of claim 18 wherein Y is S(O)$_2$, —N(S(O)$_2$CH$_3$)— or —N(R$_6$) SO$_2$—, wherein $R_6$ is H or $C_{1-4}$alkyl.
27. The compound of claim 26 wherein n is 0.
28. The compound of claim 18 wherein
Ring a is selected from

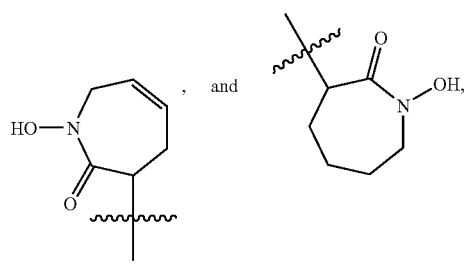

$R_1$ is selected from Ph, -Ph-Br, -Ph-Cl, -Ph-CH$_3$, -Ph-OCH$_3$, -Ph-OCF$_3$, -Ph-CF$_3$, and

$R_2$ is selected from 0-1 member selected from $C_{1-4}$alkyl optionally substituted with

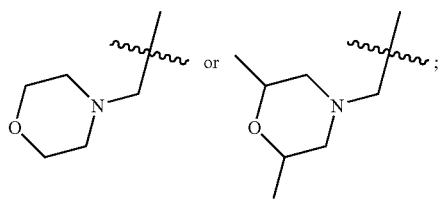

Z is —$CH_2$—;
Y is selected from $S(O)_2$, —$N(R_6)SO_2$—, and —$N(SO_2R_8)$—, wherein $R_6$ is H or $C_{1-4}$alkyl optionally substituted with oxo,

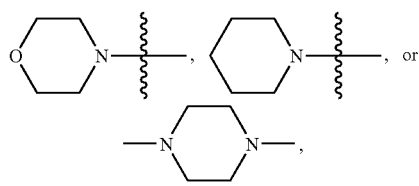

and $R_8$ is $C_{1-4}$alkyl;
W is selected from a covalent bond, O, and —C≡C—; and m is 0.

29. The compound of claim 28 wherein Y is selected from $S(O)_2$, —$N(CH_3)SO_2$—, —NH—$SO_2$—, and

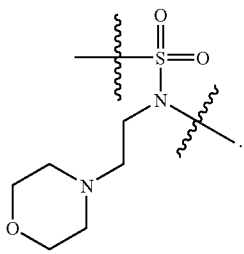

30. The compound of claim 1 selected from

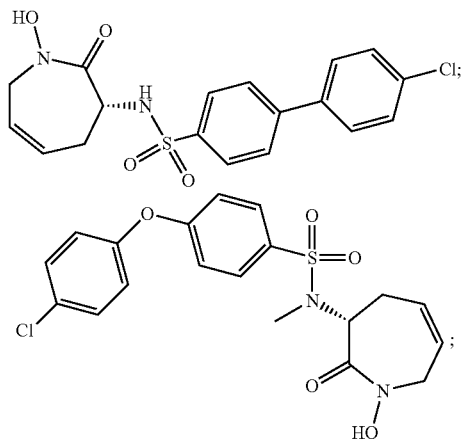

-continued

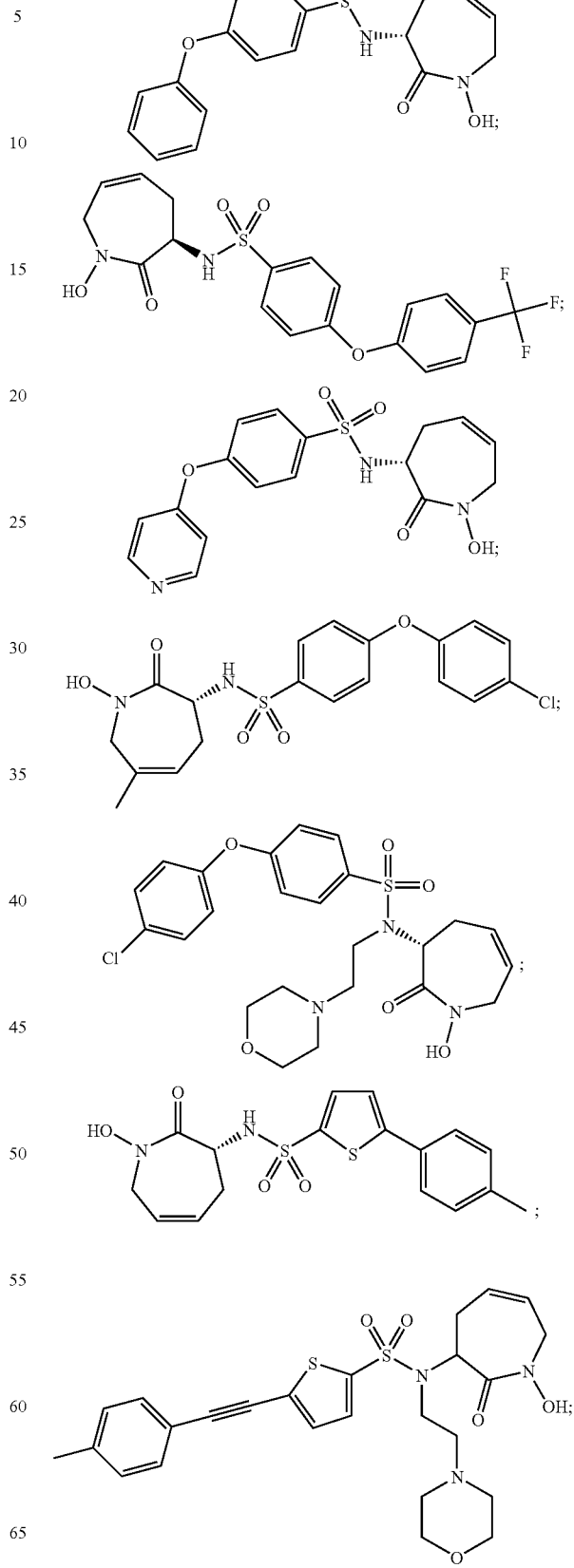

-continued
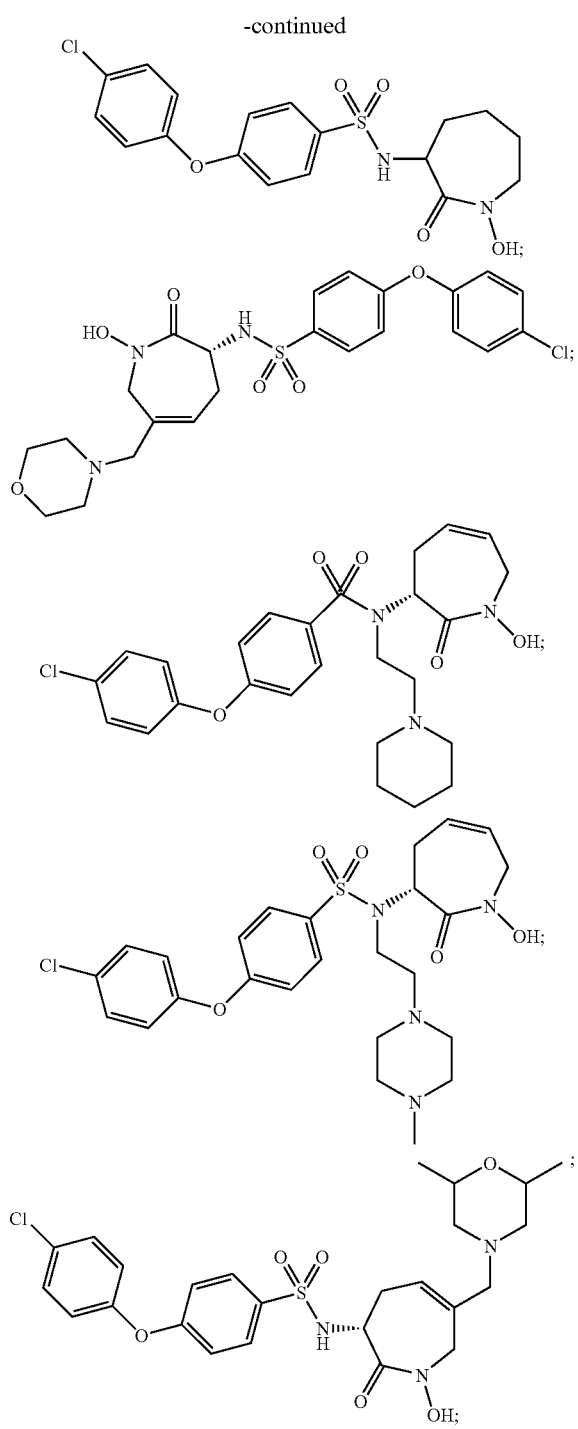
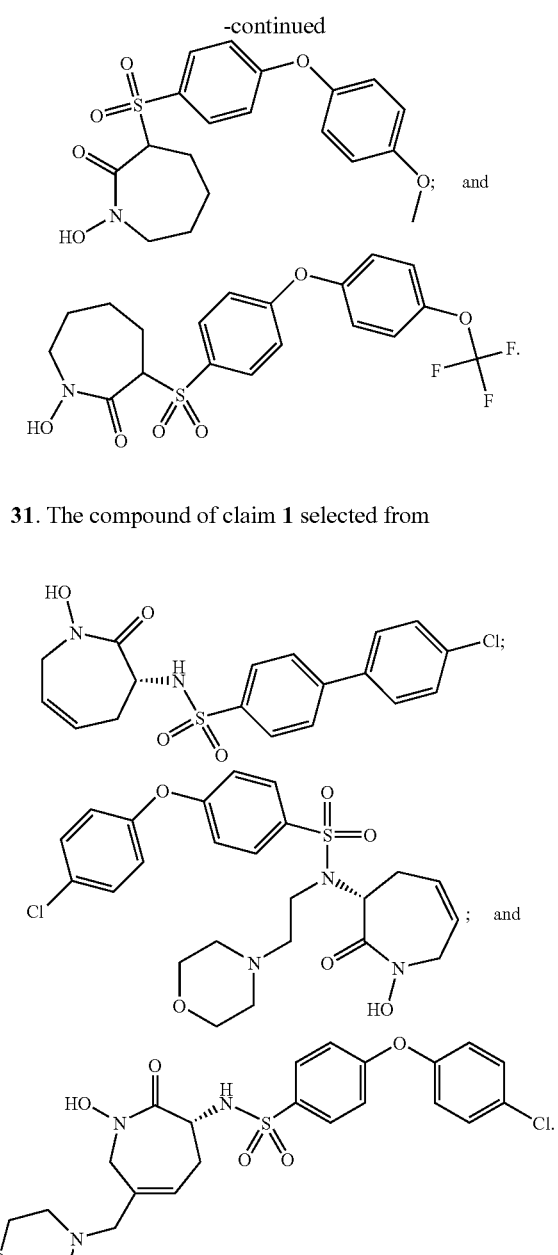
31. The compound of claim 1 selected from
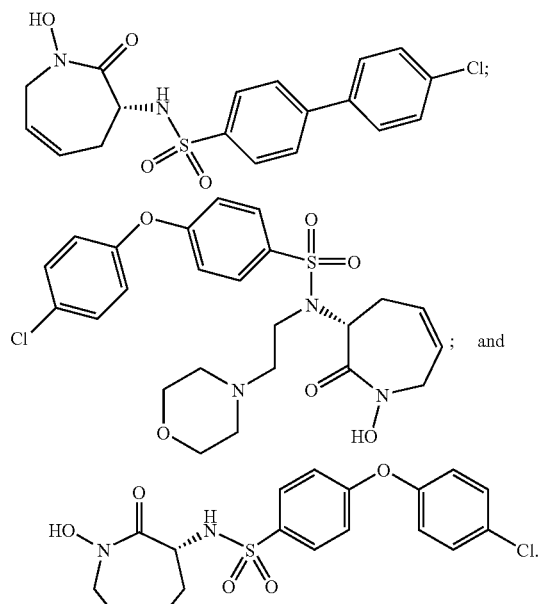
32. A pharmaceutical composition comprising a compound of claim 1 and a pharmaceutically acceptable carrier.
* * * * *